United States Patent
Brodsky

(10) Patent No.: US 7,291,699 B2
(45) Date of Patent: Nov. 6, 2007

(54) PRODUCT AND METHODS FOR DIAGNOSIS AND THERAPY FOR CARDIAC AND SKELETAL MUSCLE DISORDERS

(75) Inventor: Gary Brodsky, Denver, CO (US)

(73) Assignee: The Regents of the University of Colorado, Boulder, CO (US)

( * ) Notice: Subject to any disclaimer, the term of this patent is extended or adjusted under 35 U.S.C. 154(b) by 0 days.

(21) Appl. No.: 10/803,541

(22) Filed: Mar. 17, 2004

(65) Prior Publication Data

US 2005/0090438 A1   Apr. 28, 2005

Related U.S. Application Data

(60) Provisional application No. 60/456,642, filed on Mar. 18, 2003.

(51) Int. Cl.
*C07K 14/00* (2006.01)
*A61K 38/00* (2006.01)
*C12N 5/06* (2006.01)

(52) U.S. Cl. .......................... 530/300; 530/350; 514/2; 435/325

(58) Field of Classification Search .................. None
See application file for complete search history.

(56) References Cited

U.S. PATENT DOCUMENTS

2005/0059071 A1 *  3/2005  Eriksson et al. ............... 435/6

OTHER PUBLICATIONS

Park, H-W. et al. Science 275: 1800-1804 (1997).*
Kilic, F. et al. Journal of Biological Chemistry 272(8): 5298-5304 (1997).*
Barton and Worman, "Prenylated prelamin A interacts with Narf, a novel nuclear protein", Journal of Biological Chemistry 274(42): 30008-30018 (1999).*
Ostlund et al., "Properties of lamin A mutants found in Emery-Dreifuss muscular dystrophy, cardiomyopathy and Dunnigan-type partial lipodystrophy", Journal of Cell Science 114(24): 4435-4445 (2001).*
Favreau et al., "Expression of Lamin A mutated in the carboxy-terminal tail generates an aberrant nuclear phenotype similar to that observed in cells from patients with Dunnigan-type partial lipodystrophy and Emery-Dreifuss muscular dystrophy", Experimental Cell Research 282: 14-23 (2003; Published online Nov. 11, 2002).*
Kilic et al., "Regulation of prelamin A endoprotease activity by prelamin A", FEBS Letters 414: 65-68 (1997).*
Bergo et al., (2002) *Proc Natl Acad Sci U S A* 99:13049-54.
Boyartchuk & Rine (1998) *Genetics* 150:95-101.
Brodsky et al., (2000) *Circulation* 101:473-6.
Chaly et al., (1996) *J Cell Biochem* 62:76-89.
Dalton et al., *Cancer Res.* 55:3295-3304 (1995).
Fatkin et al., (1999) *N Engl J Med* 341:1715-24.
Lloyd et al., (2002) *Human Molecular Genetics* (2002) 11(7):769-777.
Lutz et al., (1992) *Proc Natl Acad Sci U S A* 89:3000-4; Izumi et al., (2000) *Mol Biol Cell* 11:4323-37.
Marcus et al., (1990) *Biochem Biophys Res Commun* 172:1310-6.
Muralikrishna et al., (2001) *J Cell Sci* 114:4001-11.
Ostlund et al., (2001) *J Cell Sci* 114:4435-45.
Pendas et al., *Nat Genet* 31:94-99 (2002).
Raharjo et al., (2001) *J Cell Sci* 114:4447-57.
Sinensky et al., *J Cell Sci* 107:2215-2218 (1994).
Sullivan et al., (1999) *J Cell Biol* 147:913-20.
Taylor et al., (2003) *Journal of the American College of Cardiology*, 41:771-780.
Trueblood et al., (2000) *Molecular and Cellular Biology* 20(12):4381-4392.

* cited by examiner

*Primary Examiner*—Robert A. Wax
*Assistant Examiner*—Anand Desai
(74) *Attorney, Agent, or Firm*—Sheridan Ross P.C.

(57) ABSTRACT

Disclosed are products and methods to promote myoblast activation and cardiac and skeletal muscle growth or regeneration, and to treat heart and skeletal muscle diseases, based on the identification of cellular processes affected by prelamin A processing.

15 Claims, 2 Drawing Sheets

FIG. 2

Alignment of pre sequences

|  | 1 | 2 | 3 | 4 | 5 | 6 | 7 | 8 | 9 | 10 | 11 | 12 | 13 | 14 | 15 | 16 | 17 | 18 | |
|---|---|---|---|---|---|---|---|---|---|---|---|---|---|---|---|---|---|---|---|
| Human | L | L | G | N | S | S | P | R | T | Q | S | P | Q | N | C | S | I | M | (SEQ ID NO:20) |
| Mouse | L | L | G | N | S | S | P | R | S | Q | S | S | Q | N | C | S | I | M | (SEQ ID NO:21) |
| Chicken | V | L | G | G | A | G | P | R | R | Q | A | PAPQ | | G | C | S | I | M | (SEQ ID NO:22) |
| Xenopus | I | V | G | N | G | Q | R | A | Q | V | A | P | Q | N | C | S | I | M | (SEQ ID NO:23) |
| Zebrafish | I | V | S | N | D | K | P | R | Q | A | G | P | KVDN | | C | S | I | M | (SEQ ID NO:24) |

PRODUCT AND METHODS FOR DIAGNOSIS AND THERAPY FOR CARDIAC AND SKELETAL MUSCLE DISORDERS

CROSS-REFERENCE TO RELATED APPLICATIONS

This application Claims the benefit of priority under 35 U.S.C. § 119(e) from U.S. Provisional Application No. 60/456,642, filed Mar. 18, 2003, entitled "Product and Methods for Diagnosis and Therapy for Cardiac and Skeletal Muscle Disorders". The entire disclosure of U.S. Provisional Application No. 60/456,642 is incorporated herein by reference.

FIELD OF THE INVENTION

This invention generally relates to products and methods to promote myoblast activation and cardiac and skeletal muscle growth or regeneration based on the identification of cellular processes affected by prelamin A processing.

BACKGROUND OF THE INVENTION

Mutations in the human lamin A/C gene cause dilated cardiomyopathy (DCM) (Brodsky et al., (2000) *Circulation* 101:473-6; Fatkin et al., (1999) *N Engl J Med* 341:1715-24; Taylor et al., (2003) *Journal of the American College of Cardiology,* 41:771-780), Emery-Dreifuss muscular dystrophy (Bonne et al., (1999) *Nature Genet.* 21:285-288), limb-girdle muscular dystrophy (Muchir et al., (2000) *Hum Mol Genet* 9:1453-9), partial lipodystrophy (Shackleton et al., (2000) *Nat Genet* 24:153-6), axonal neuropathy (De Sandre-Giovannoli et al., (2002) *Am J Hum Genet* 70:726-36) and mandibuloacral dysplasia (Novelli et al., (2002) *Am J Hum Genet* 71:426-31). Along with lamin B, lamins A and C are the major constituents of the nuclear lamina, a meshwork of protein filaments that underlies the nucleoplasmic face of the inner nuclear membrane. The nuclear lamina provides structural support for the nucleus (Newport et al., (1990) *J Cell Biol* 111:2247-59; Spann et al., (1997) *J Cell Biol* 136:1201-12), and plays a role in the regulation of gene transcription through direct and indirect interactions with transcription factors (Ozaki et al., (1994) *Oncogene* 9:2649-53; Markiewicz et al., (2002) *Mol Biol Cell* 13:4401-13; Spann et al., (2002) *J Cell Biol* 156:603-8), and by organizing intranuclear RNA splicing factor compartments (Kumaran et al., (2002) *J Cell Biol* 159:783-93). Lamins bind directly to DNA, and are involved in chromatin organization via direct interactions with histones and other chromatin binding proteins (Gotzmann & Foisner (1999) *Crit Rev Eukaryot Gene Expr* 9:257-65). Site-specific phosphorylation of lamin A results in the reversible disassembly of the lamina during mitosis (Haas & Jost (1993) *Eur J Cell Biol* 62:237-47), and lamin A is a target of endoproteolytic cleavage during apoptosis (Slee et al., (2001) *J Biol Chem* 276:7320-6).

Lamins A and C are differentially transcribed from the lamin A/C gene. Lamin A is expressed as a pre-protein (Gerace et al., (1984) *J Cell Sci Suppl* 1:137-60) that undergoes a sequential series of post-translational modifications (Sinensky et al., (1994) *J Cell Sci* 107:61-7) shared by the *S. cerevisiae* a-type mating pheromone (Marcus et al., (1990) *Biochem Biophys Res Commun* 172:1310-6), culminating in the endoproteolytic removal of the modified 15 amino acid residue C-terminal peptide. While proper processing of the prelamin A tail has been shown to affect the rate of mature lamin A incorporation into the nuclear lamina (Lutz et al., (1992) *Proc Natl Acad Sci USA* 89:3000-4; Izumi et al., (2000) *Mol Biol Cell* 11:4323-37), the physiological function of prelamin A processing has not been determined.

Lamins A and C are expressed in nearly all cell types concomitant with differentiation (Rober et al., (1989) *Development* 105:365-78). The reason why mutations in the lamin A/C gene result in tissue-specific abnormalities and the molecular mechanisms by which lamin A/C mutations exert their effects on these tissues has yet to be elucidated.

The initial cloning of lamin A/C indicated that the protein was processed. In the early 1990's, investigators began elucidating the processing pathway of prelamin A, and the localization and characteristics of enzymes involved in its processing (Lutz et al., (1992), supra; Dalton et al., *Cancer Res.* 55:3295-3304 (1995); Sinensky et al., *J Cell Sci* 107: 2215-2218 (1994)). These researchers also investigated the biological function of the "pre" sequence by preventing its cleavage from the prelamin A protein, and inhibiting its processing in mononucleate cell lines. These studies demonstrated that the presence of the "pre" sequence prevented incorporation into the lamina, and also showed that mature lamin A lacking the pre-sequence could substitute for the native prelamin A without any biological consequences. In one of these studies, the authors comment that "nucleoplasmic localization of prelamin A or the peptide released during processing may have some regulatory significance" (Lutz et al., (1992), supra).

Investigators have reported the construction of a lamin A/C knock-out mouse that has cardiac and skeletal muscle phenotypes similar to those seen in patients with DCM and EDMD (Sullivan et al., (1999) *J Cell Biol* 147:913-20). Over the last two years, investigators have generated mice which lack the mouse homologues of the enzymes in the yeast Mat A processing pathways (Pendas et al., *Nat Genet* 31:94-99 (2002); Bergo et al., (2002) *Proc Natl Acad Sci USA* 99:13049-54). These animals appear to be phenocopies of the lamin A/C knock-out mice. These investigators have demonstrated that prelamin A is not properly processed in these animals.

Consequently, the published literature demonstrates that lamin A expression, and proper prelamin A processing are essential for normal post-natal cardiac and skeletal muscle biology in mice. The published data also shows that prelamin A must be processed to mature lamin A prior to incorporation into the nuclear lamina. However, there is no published data identifying the cellular function of prelamin A processing, or the mechanism by which mutations in the lamin A/C gene, or the deletion of the lamin A/C gene and enzymes that process prelamin A, lead to cardiac and skeletal muscle abnormalities. Such information would be invaluable for in the understanding of cardiac and skeletal muscle disease processes affected by lamin A/C disease mutations, as well as the ability to design therapies to prevent these and other cardiac and skeletal muscle diseases.

SUMMARY OF THE INVENTION

One embodiment of the present invention relates to an isolated prelamin A pre peptide selected from: (a) a peptide consisting essentially of SEQ ID NO:2; (b) a biologically active fragment of SEQ ID NO:2; (c) a peptide consisting essentially of an amino acid sequence that is at least about 70% identical to SEQ ID NO:2, wherein the peptide has the biological activity of SEQ ID NO:2; and (d) a peptide consisting essentially of an amino acid sequence that differs from SEQ ID NO:2 by at least one substitution, deletion or insertion of an amino acid residue at a position of SEQ ID NO:2 selected from the group consisting of: 1, 2, 5, 6, 9, 10, 11, 12, 13 and 14, wherein the peptide has the biological activity of SEQ ID NO:2. In one aspect, the peptide consists essentially of an amino acid sequence that is at least about 80% identical to SEQ ID NO:2, or in another aspect, is at least about 90% identical to SEQ ID NO:2. In one aspect, the peptide consists essentially of an amino acid sequence that differs from SEQ ID NO:2 by at least one substitution, deletion or insertion of an amino acid residue at a position of SEQ ID NO:2 selected from: 1, 2, 5, 6, 9, 10, 11 and 12. In another aspect, the peptide consists essentially of an amino acid sequence that differs from SEQ ID NO:2 by at least one substitution, deletion or insertion of an amino acid residue at a position of SEQ ID NO:2 selected from: 1, 2, 5, 6, 9, 10 and 11. In one aspect, the peptide consists essentially of SEQ ID NO:2. In another aspect, the peptide comprises a modification selected from the group consisting of farnesylation, carboxymethylation, geranyl-geranylation, and complexing with a lipid carrier.

Another embodiment of the present invention relates to a therapeutic composition comprising any of the above-described peptides and a pharmaceutically acceptable carrier.

Yet another embodiment of the present invention relates to an isolated nucleic acid sequence encoding any of the above-described peptides. In one aspect, the nucleic acid sequence is SEQ ID NO:1.

Another embodiment of the present invention relates to a recombinant nucleic acid molecule comprising any of the above-described nucleic acid sequences operatively linked to a recombinant vector. In one aspect, the nucleic acid sequence is operatively linked to a promoter selected from: a cardiac-specific promoter, a muscle-specific promoter, and a prelamin A promoter. In a preferred aspect, the nucleic acid sequence is operatively linked to a myosin heavy chain promoter. In one aspect, the recombinant vector is a viral vector.

Yet another embodiment of the present invention relates to a recombinant nucleic acid molecule comprising a nucleic acid sequence operatively linked to a recombinant expression vector for gene delivery, the nucleic acid sequence being selected from: (a) a nucleic acid sequence encoding SEQ ID NO:4; (b) a nucleic acid sequence encoding a biologically active fragment of SEQ ID NO:4; and (c) a nucleic acid sequence encoding an amino acid sequence that is at least about 70% identical to SEQ ID NO:4, wherein the amino acid sequence has prelamin A or lamin A biological activity.

Another embodiment of the present invention relates to a therapeutic protein comprising a protein selected from: (a) a protein comprising an amino acid sequence represented by SEQ ID NO:4; (b) a protein comprising biologically active fragment of SEQ ID NO:4; and (c) a protein comprising an amino acid sequence that is at least about 70% identical to SEQ ID NO:4, wherein the protein has prelamin A or lamin A biological activity. In this embodiment, the protein is chemically or recombinantly attached to a therapeutic agent that increases the half-life of the protein in cardiac or skeletal muscle tissue.

Yet another embodiment of the present invention relates to a carrier for therapeutic agents for the treatment of cardiac or skeletal muscle disorders. The carrier consists essentially of an isolated fragment of SEQ ID NO:4 with inter-nuclear transport domain biological activity, or a biologically active homologue thereof.

Another embodiment of the present invention relates to a therapeutic composition for promoting myoblast activation and growth or regeneration of cardiac or skeletal muscle. The composition comprises an isolated peptide consisting essentially an isolated fragment of SEQ ID NO:4 with inter-nuclear transport domain biological activity or a biologically active homologue thereof, operatively linked to a therapeutic agent for promoting myoblast activation and growth or regeneration of cardiac or skeletal muscle.

Yet another embodiment of the present invention relates to a recombinant nucleic acid molecule comprising: (a) a nucleic acid sequence encoding an isolated fragment of SEQ ID NO:4 with inter-nuclear transport domain biological activity or a biologically active homologue thereof, operatively linked to (b) a nucleic acid sequence encoding a protein for the promotion of myoblast activation and growth or regeneration of cardiac or skeletal muscle.

Another embodiment of the present invention relates to a method to promote myoblast activation and regeneration of damaged, degenerated or atrophied cardiac and skeletal myocytes. The method includes the step of administering to a patient that has damaged, degenerated or atrophied cardiac or skeletal myocytes an agent selected from: (a) any of the above-described peptides; (b) any of the above-described compositions; (c) any of the above-described recombinant nucleic acid molecules; and (d) any of the above-described therapeutic proteins.

Yet another embodiment of the present invention relates to a method to stimulate cardiac or skeletal muscle growth in a mammal. The method includes the step of administering to a mammal an agent selected from: (a) any of the above-described peptides; (b) any of the above-described compositions; (c) any of the above-described recombinant nucleic acid molecules; and (d) any of the above-described therapeutic proteins.

Another embodiment of the present invention relates to a method to treat cardiac and skeletal muscle disorders. The method includes the step of administering to a patient that has a cardiac or skeletal muscle disorder, an agent selected from: (a) any of the above-described peptides; (b) any of the above-described compositions; (c) any of the above-described recombinant nucleic acid molecules; and (d) any of the above-described therapeutic proteins. Cardiac and skeletal muscle disorders to treat using the method of the present invention include, but are not limited to, dilated cardiomyopathy, Emery-Dreifuss muscular dystrophy, limb-girdle muscular dystrophy, partial lipodystrophy, axonal neuropathy, and mandibuloacral dysplasia.

Yet another embodiment of the present invention relates to a method to identify compounds that regulate myoblast activation and differentiation. The method includes the steps of: (a) contacting a cell that expresses a prelamin A protein or a prelamin A pre peptide with a test compound under conditions suitable for modulation of the activity of the prelamin A protein or prelamin A pre peptide by the test compound; and (b) detecting modulation of the activity of the prelamin A protein or prelamin A pre peptide by the test compound. The step of detecting can include, but is not limited to, detecting whether the test protein regulates prelamin A pre peptide transport in a cell; detecting whether the test protein regulates the processing of prelamin A in a cell; detecting whether the test protein regulates myoblast differentiation; detecting binding between the prelamin A protein or prelamin A pre peptide and the test compound (e.g., by a yeast two hybrid assay). In one aspect, the test compound is a protein encoded by a gene that is a candidate for regulation of prelamin A processing or prelamin A pre peptide transport in the cell. For example, the gene can be a human homologue of a gene in the yeast a-type mating pheromone signaling pathway, or the gene can be a gene encoding a candidate receptor for the prelamin A pre peptide. In another aspect, the test compound is a pharmaceutical compound. In one aspect, the cell expressing the prelamin A protein or prelamin A pre peptide is a differentiating cardiac myocyte or a differentiating skeletal myocyte. In another aspect, the cell expressing the prelamin A protein or prelamin A pre peptide has been transfected with a nucleic acid molecule encoding the prelamin A protein or prelamin A pre peptide. In yet another aspect, the prelamin A is processing deficient. In yet another aspect, the cell is a prelamin A processing deficient cell.

Yet another embodiment of the present invention relates to a method to identify compounds that regulate myoblast activation and differentiation. The method includes the steps of: (a) contacting a prelamin A protein or a prelamin A pre peptide with a test compound under conditions suitable for binding of the prelamin A protein or prelamin A pre peptide by the test compound; and (b) detecting binding of the prelamin A protein or prelamin A pre peptide by the test compound. Binding can be detected by any suitable technique including, but not limited to, a yeast two hybrid assay or immunoprecipitation assay.

Another embodiment of the present invention relates to a method to identify compounds that regulate myoblast activation and differentiation in a cell. The method includes the steps of: (a) contacting an isolated prelamin A processing-deficient cell with a test compound for regulation of myoblast activation and differentiation; and (b) detecting whether the test compound regulates an activity in the cell selected from the group consisting of: prelamin A processing, prelamin A pre peptide transport, and myoblast activation or differentiation, as compared to in the absence of the test compound. In one aspect, the isolated prelamin A processing-deficient cell is selected from: a cell transfected with a nucleic acid sequence encoding a processing deficient prelamin A protein and a prelamin A processing deficient cell that has been isolated from a patient. In one aspect, the cell is transfected with a nucleic acid sequence encoding a prelamin A protein. In another aspect, the cell is transfected with a nucleic acid sequence encoding a processing-deficient prelamin A protein. In another aspect, the processing-deficient prelamin A is a naturally occurring processing-deficient prelamin A protein. In yet another aspect, the processing-deficient prelamin A is a synthetically created processing-deficient prelamin A protein. In another aspect, the cell endogenously expresses a processing-deficient prelamin A protein. In one aspect, the cell is selected from a cardiac myocyte and a skeletal myocyte. In another aspect, the cell is a prelamin A processing deficient cell that has been isolated from a patient, wherein the cell expresses a prelamin A protein comprising a mutation (with respect to SEQ ID NO:4) selected from: Arg60Gly, Leu85Arg, Glu203Gly, Arg89Leu, Asn195Lys, and Arg377His.

In this embodiment of the invention, the step of detecting can include, but is not limited to, detecting whether the test compound increases prelamin A processing in the cell as compared to in the absence of the compound; detecting whether the test compound increases prelamin A pre peptide transport in the cell as compared to in the absence of the compound; detecting whether the test compound increases myoblast activation or differentiation in the cell as compared to in the absence of the compound; or detecting an increase in myoblast activation and differentiation in the absence of correcting the prelamin A processing deficiency.

In one aspect of this embodiment of the invention, the test compound is a homologue of prelamin A pre peptide with putative prelamin A pre peptide biological activity. In another aspect, the test compound is a pharmaceutical compound with putative prelamin A pre peptide biological activity. In another aspect, the test compound is a homologue of prelamin A with putative prelamin A biological activity. In another aspect, the test compound is a candidate protein for a prelamin A processing enzyme, or a gene encoding the candidate protein. In yet another aspect, the test compound is a candidate protein for a downstream prelamin A pre peptide signal transduction protein, or a gene encoding the candidate protein. In another aspect, the test compound is a putative pharmaceutical compound for use in the treatment of cardiac and skeletal muscle disorders, wherein an increase in the processing of prelamin A in the cell or an increase in myoblast activation and differentiation in the presence of the compound as compared to in the absence of the compound indicates that the compound is a therapeutic compound for use in the treatment of cardiac and skeletal muscle disorders.

Yet another embodiment of the present invention relates to a method to identify human genes that regulate myoblast activation and differentiation. The method includes the steps of: (a) contacting a probe with a source of human DNA from heart or skeletal muscle tissue under moderate stringency conditions, wherein the probe is a nucleic acid sequence from a gene in the yeast a-type mating pheromone signal transduction pathway; (b) identifying genes in the source of human DNA that hybridize to the probe; and (c) detecting whether genes that hybridize to the probe encode a protein that corrects a prelamin A processing deficiency or that increases myoblast activation and differentiation. In one aspect, the gene in the yeast a-type mating pheromone signal transduction pathway is a gene that is associated with a biological function selected from: transcriptional activation of pheromone responsive genes, post-transcriptional blockade of the cell cycle, and cell fusion pathway activation.

Another embodiment of the present invention relates to a method to identify an inhibitor of prelamin A farnesylation. The method includes the steps of: (a) contacting an isolated cell that expresses prelamin A with a putative regulator of prelamin A farnesylation; and (b) detecting whether farnesylation of prelamin A is inhibited by the putative regulator. In one aspect, cell is selected from the group consisting of a differentiating cardiac myocyte and a differentiating skeletal myocyte, and in another aspect, the cell has been transfected with a nucleic acid molecule encoding prelamin A. The step of detecting can include, but is not limited to, detecting whether prelamin A farnesylation is reduced as compared to in the absence of the putative inhibitor compound. In one aspect, the method further comprises a step (c) of detecting whether inhibitors of prelamin A farnesylation detected in step (b) regulate prelamin A processing in the cell, wherein detection of reduced prelamin A processing in the presence of the regulator indicates that the regulator may be useful for treatment of muscle cell cancers. In another aspect, the method further includes step (c) of detecting whether inhibitors of prelamin A farnesylation detected in step (b) cause myoblast dissociation or myoblast cell death, wherein detection of increased myoblast dissociation or myoblast cell death in the presence of the regulator indicates that the regulator may be useful for treatment of muscle cell cancers.

Yet another embodiment of the present invention relates to a method to treat a muscle cell cancer, comprising administering to a patient with a muscle cell cancer or metastatic cancer thereof a compound that inhibits prelamin A processing and myoblast differentiation and is toxic to myocytes. The muscle cell cancer can include, but is not limited to, myosarcoma, myeloma, myoma, rhabdomyosarcoma, and malignant uterine fibroids. In one aspect, the compound inhibits farnesylation of prelamin A. In another aspect, the compound is a statin that is toxic to myocytes. The compound can be identified by the methods described above.

Another embodiment of the invention relates to a processing deficient prelamin A peptide. The processing deficient prelamin A peptide consists essentially of an amino acid sequence that differs from SEQ ID NO:4 by at least one substitution, deletion or insertion that results in a decrease in a prelamin A or prelamin A pre peptide biological activity selected from: (a) prelamin A processing to release a prelamin A pre peptide consisting of SEQ ID NO:2 or a biologically active homologue thereof; (b) prelamin A pre peptide signal transduction; (c) synchronization of intercellular signaling with changes in lamin A localization and nuclear lamina morphology that occur early in myoblast differentiation; (d) synchronization of transcriptional regulation of muscle-specific genes or cell cycle arrest that occurs concomitant with myoblast differentiation; (e) formation of normal nuclear lamina structure; and/or (f) induction of myoblast activation and differentiation. In one aspect, the processing deficient prelamin A peptide consists essentially of an amino acid sequence that differs from SEQ ID NO:4 by a substitution of an amino acid residue in SEQ ID NO:4 selected from: Arg60, Leu85, Glu203, Arg89, Asn195, Arg377, Tyr646, G649, N650, P653, R654, P658, Q659, N660, Cys661, S662, I663 and M664. In another aspect, the substitution is selected from: Arg60Gly, Leu85Arg, Glu203Gly, Arg89Leu, Asn195Lys, and Arg377His.

Another embodiment of the invention relates to an isolated cell transfected with a processing deficient prelamin A peptide as described above.

BRIEF DESCRIPTION OF THE FIGURES OF THE INVENTION

FIG. 2 is an alignment of the amino acid sequence of the pre peptide portion of prelamin A from 5 different animal species.

DETAILED DESCRIPTION OF THE INVENTION

Figure 1:
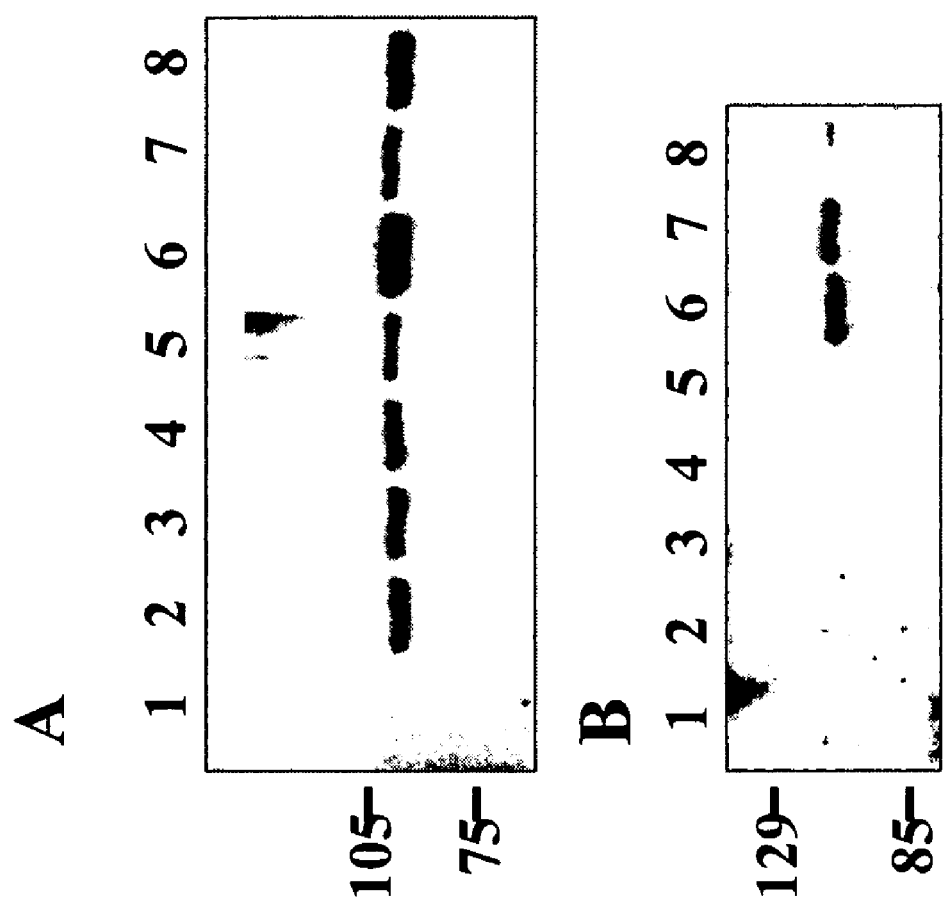
FIGS. 1A and 1B are digitized images of a Western blot for prelamin A GFP-fusion proteins identified using anti-GFP antibody (FIG. 1A) and anti-prelamin A antibody (FIG. 1B).

The present invention relates to the discovery by the present inventor of the mechanisms by which a class of genetic mutations results in heart disease and muscular dystrophies. The present invention also relates to the identification of therapeutic agents useful for treating such diseases, as well as for generally promoting myoblast activation and the growth or regeneration of cardiac and skeletal muscle. Such agents will also be useful, for example, in cases where heart and skeletal muscle have been damaged by non-disease pathways and aging. The present invention also relates to use of mutant protein and cell lines for the further identification of the genes and proteins that are relevant for proper heart and skeletal muscle function, as well as cancer development. The present invention also relates to the use of various genes, proteins, and cell lines described herein to identify additional gene and protein targets for the treatment of heart and skeletal muscle diseases.

More specifically, the present inventor has discovered that various mutations in the lamin A/C gene that are associated with certain cardiac and skeletal muscle disorders affect prelamin A processing, sub-cellular prelamin A/lamin A localization, and nuclear lamina formation in the cell types affected by these diseases. The inventor has shown that expression of prelamin A proteins containing such mutations results in aberrant cardiac and skeletal myocyte differentiation, morphology and organization, reflecting what is seen in patients with these diseases. This is believed to be the first demonstration of any biologically significant effect of any lamin A/C disease mutations.

The inventor's discovery demonstrates that improper prelamin A processing results in severely aberrant cardiac and skeletal myocyte differentiation. This is believed to be the first identification of a cellular process that is affected by preventing prelamin A processing. These results indicate that the "pre" peptide of prelamin A serves an analogous function to that of the *S. cerevisiae* a-type mating factor or a-type mating pheromone, which is the only known protein that is processed in a similar manner to prelamin A. The present inventor's data indicate that the "pre" sequence of prelamin A functions as a signaling molecule when proteolytically released from the prelamin A protein. Based on the experimental results provided herein, and by the present inventor's analogy to the demonstrated function of the yeast a-type mating pheromone, the "pre" sequence of prelamin A indicates the proximity and direction of mononucleate myoblasts during differentiation and cell fusion to generate multinucleate myocytes. The removal of the "pre" sequence results in the synchronized incorporation of the mature lamin A protein into the nuclear lamina, altering the lamina structure and affecting gene transcription and/or cell cycle arrest. Consequently, lamin A/C mutations affecting prelamin A processing, "pre" signaling, or lamina formation will result in disease.

Mutations in the human lamin A/C gene cause cardiac and skeletal muscle disease, as well as diseases affecting adipocytes and neurons (see Background discussion). As lamin A/C is expressed in nearly all adult cell types, and is directly involved in many nuclear processes, the mechanisms by which mutations in this gene lead to tissue-specific phenotypes has led to considerable speculation regarding putative disease mechanisms. While evidence has been presented demonstrating that the lamin A/C mutations resulting in partial lipodystrophy affect interactions with an adipocyte-specific transcription factor (Lloyd et al., (2002) *Hum Mol Genet* 11:769-77), no specific functional effects of lamin A/C disease mutations on cardiac or skeletal muscle cell biology have been demonstrated. The present inventor has directly demonstrated herein that mutations in the lamin A/C gene associated with dilated cardiomyopathy affect nuclear lamina structure and prelamin A processing resulting in aberrant myoblast differentiation.

Prelamin A processing proceeds through a sequential series of post-translational protein modifications (Sinensky et al., (1994), supra). While a number of studies have demonstrated that the proper processing and subsequent removal of the prelamin A tail is necessary for the efficient incorporation of mature lamin A into the nuclear lamina, the biological significance of prelamin A processing has remained elusive.

The only protein known to be post-translationally processed in the same manner as prelamin A is the yeast a-type mating pheromone (yeast a-factor) (Boyartchuk & Rine (1998) *Genetics* 150:95-101). This mating factor is expressed as pre-pro-protein, and the farnesylated, carboxymethylated C-terminal peptide that is released by endoproteolytic cleavage is the biologically active species. Yeast a-factor is a peptide pheromone that indicates the proximity and distance of adjacent yeast haploid cells during the process of yeast mating, which results in cell fusion and the production of diploid yeast cells. The yeast a-factor peptide binds to a trimeric G-protein coupled receptor, which activates a mitogen-activated protein (MAP) kinase. The MAP kinase then activates three distinct pathways leading to transcriptional activation of pheromone response regulated genes, post-transcriptional blockade of the cell cycle, and polarized morphogenesis (for review, see Elion, E. A. (2000) Curr Opin Microbiol 3:573-81). As a result of the present inventor's discovery, it can now be seen that the fact that prelamin A processing is analogous to yeast a-factor processing is supported by the finding that knockout mice which do not express the murine homologue (Zmpste24) of one of the yeast endoproteases responsible for a-factor processing (Ste24) are defective in prelamin A processing, and display aberrant cardiac and skeletal muscle morphologies that are phenocopies of those seen in the lamin A/C knockout mouse (Bergo et al., (2002), supra).

The present inventor discloses herein that proper prelamin A processing is necessary for the release of the "pre" peptide of prelamin A, which functions in analogous fashion to yeast a-factor in intercellular signaling between mononucleated myoblasts during cell fusion and the formation of multinucleated myocytes. Furthermore, as the removal of the prelamin A tail is necessary for the incorporation of mature lamin A into the nuclear lamina (Lutz et al., (1992), supra; Izumi et al., (2000), supra), the present inventor proposes that prelamin A processing synchronizes intercellular signaling with the changes in lamin A localization and nuclear lamina morphology that occur early in myoblast differentiation (Chaly et al., (1996) J Cell Biochem 62:76-89; Muralikrishna et al., (2001) J Cell Sci 114:4001-11). These changes in lamina structure are likely to be involved in the transcriptional regulation of muscle-specific genes and/or the cell cycle arrest that occurs concomitant with myoblast differentiation.

The present inventor's model explains the cardiac and skeletal muscle-specific abnormalities observed in patients with DCM, Emery-Dreifuss muscular dystrophy and limb-girdle muscular dystrophy, as well as those seen in the lamin A/C and Zmpste24 knockout mice. In addition, the finding that prelamin A processing is necessary for the fusion of mononucleated cells into multinucleated myotubes explains why no biological function could be assigned by prior investigators to prelamin A processing in non-differentiating mononucleated cell lines. Finally, the model described herein indicates that lamin A/C mutations that affect prelamin A processing, "pre" signaling, or nuclear lamina formation will result in aberrant myoblast differentiation, and consequently explains why mutations spread throughout the lamin A/C gene cause cardiac and skeletal muscle disease.

Shortly after the discovery that mutations in the human lamin A/C gene cause EDMD (Bonne et al., (1999), supra), Brodsky and colleagues (Brodsky et al., (2000), supra) and others (Fatkin et al., (1999), supra), identified disease mutations in families with DCM. Additional unpublished studies carried out in the present inventor's lab have now demonstrated that GFP-prelamin A fusion proteins containing DCM and EDMD disease mutations resulted in aberrant lamina formation in mononucleate cell lines, as assessed by direct fluorescence microscopy. Similar studies were reported by others who used mutant lamin proteins tagged with peptide markers (Ostlund et al., (2001) J Cell Sci 114:4435-45; Raharjo et al., (2001) J Cell Sci 114:4447-57), and who demonstrated that a protein that interacts with lamin A, emerin, was mislocalized as a result of mutant lamin expression. These studies required the use of indirect immunofluorescence microscopy. Due to the use of this technique, the lamina morphology results reported were ambiguous as the authors could not demonstrate if the lamina morphologies observed were due to the actual structures the mutant proteins formed, or just reflected changes in antibody-protein interactions brought about by the mutations. Previous reports (Chaly et al., (1996), supra; Muralikrishna et al., (2001), supra) had shown that antibody access could be inhibited by changes in lamina structure. In addition, the present inventor has data (currently unpublished) that directly demonstrates that indirect immunofluorescence studies of these very same mutations result in misrepresentation of the true lamina structure.

Recent screening of additional families with DCM by the present inventor's research group identified two additional mutations (Taylor et al., 2002, supra) responsible for this disease. The present inventor recently demonstrated that one of these two mutations was not processed correctly, and that expression of 4 of the 6 DCM mutations being studied resulted in aberrant cardiac and skeletal myoblast differentiation, as evidenced by misshapen and disorganized multinucleate myocytes. The mutation which prevents prelamin A processing produces the most severe phenotype. As discussed above, the present inventor's discovery is believed to be the first identification of a cellular process affected by any lamin A/C disease mutation. This is also believed to be the first demonstration of a specific biological process affected by preventing prelamin A processing.

Prior to the present invention, there were no published data identifying the cellular function of prelamin A processing, or the mechanism by which mutations in the lamin A/C gene, or the deletion of the lamin A/C gene and enzymes that process prelamin A, lead to cardiac and skeletal muscle abnormalities. The present inventor's findings are completely unique, and show that prelamin A processing is necessary for the biological process whereby mononucleate myoblasts differentiate and fuse to form multinucleate myocytes. The present inventor's data is also the first to demonstrate that lamin A/C disease mutations can interfere with this same process. This is the first demonstration of a functional cell defect arising from any lamin A/C disease mutations. The finding by the present inventor that a prelamin A processing mutant causes aberrant myocyte differentiation was the key factor in elucidating that the "pre" sequence of prelamin A functions in an analogous manner to yeast a-type mating pheromone, which signals and synchronizes haploid yeast cells prior to fusion to become a diploid cell.

While many disease mutations have been identified and shown to produce disease phenotypes in transgenic and/or knock-out mouse models, the mechanism by which these mutations exert their effects have rarely been identified. Without an understanding of how the mutations exert their effects, it is not possible to efficiently design therapeutic strategies to treat the disease. The identification of the cellular process effected by lamin A/C disease mutations and prevention of prelamin A processing by the present inventor represents an exponential leap in the understanding of these disease processes, as well as in the ability to design therapies to prevent these and other cardiac and skeletal muscle diseases.

Prior to the present invention, investigators had failed to discover the link between prevention of prelamin A processing and myoblast activation, including differentiation and cell fusion, which may be explained by a variety of reasons. First, the lamins have multiple activities. Lamin A provides structural support for the nucleus, binds transcription factors, interacts with RNA processing factors, is dynamically involved in cell cycle regulation, binds chromatin and histone proteins, and is involved in apoptosis. Consequently, many different models have been proposed to explain why lamin A/C mutations cause heart and muscle disease. The most generally accepted model suggested that structural perturbations to the lamina are exacerbated by cardiac and skeletal muscle contraction, causing the nuclei in these tissues to be damaged.

Second, the farnesylation of all other human proteins serves to anchor these proteins to membranes. Consequently, the finding by prior investigators that removal of the farnesylated pre-peptide of prelamin A was necessary for the incorporation of the mature lamin A protein into the lamina led most to believe that the "pre" sequence functions to regulate the production and activity of mature lamin A, and has no activity of its own. This concept was likely reinforced by the fact that the peptide from which yeast a-type mating pheromone is released has no biological activity. As a result, the fact that lamin A had clear biological activities apparently led most investigators to believe that, in contrast to yeast a-type mating pheromone, the "pre" sequence was not a biologically active part of the prelamin A protein.

While the processing of prelamin A does allow the mature lamin A protein to incorporate into the nuclear lamina, thereby synchronizing changes in lamina structure associated with myocyte differentiation with the release of the "pre" peptide signal, the nearly ubiquitous expression pattern of the lamin A/C gene prevented the identification of the cell types in which this processing takes place. In other words, because researchers didn't know the function of prelamin A processing, they didn't know what cell types to use as models. Without using the correct cell types (e.g., differentiating cardiac and skeletal myocytes) there was no way to identify the biological function of prelamin A processing as the present inventor has now done.

Furthermore, the fact that other disease-causing mutations in the lamin A/C gene, as well as a knock-out of the mouse lamin A/C gene, were shown to also cause adipocyte and neuronal abnormalities complicated the elucidation of the function of prelamin A by demonstrating that muscle was not the only tissue type affected by mutations in lamin A/C. Furthermore, muscle tissue has many other unique characteristics in addition to containing multinucleated cells derived from the fusion of mononucleated myoblasts.

Finally, extensive studies of prelamin A processing have been performed for more than ten years, using both chemical agents and laboratory induced mutations, without identifying the biological function of this post-translational modification. These studies failed to identify the function of prelamin A processing primarily because they utilized mononucleated cell lines in which prelamin A processing has no biological function. One key factor in elucidating the function of prelamin A processing by the present inventor was the determination in the present inventor's laboratory that a DCM mutation prevented proper processing and resulted in aberrant cardiac and skeletal myocyte differentiation. Furthermore, it was the identification of the function of prelamin A processing combined with the findings that all of the disease mutations studied affected lamina structure, and 4 of the 6 mutations caused aberrant myocyte differentiation, that lead to the discovery that all of the disease mutations were affecting the same cellular process. Once this realization was made, the present inventor was able to re-evaluate an extensive amount of data produced in his laboratory and published in the literature, and discovered that mutations that caused aberrant lamina formation and which prevented prelamin A processing were effecting two halves of a single signaling pathway which mediates myocyte differentiation and fusion. The concomitant identification in the present inventor's laboratory of changes in the lamina architecture, altered prelamin A processing, and aberrant cardiac and skeletal myocyte differentiation resulting from lamin A/C disease mutations, identification of the mechanism by which lamin A/C mutations lead to cardiac and skeletal muscle disease, and the function of prelamin A processing, led to the present invention and the products and methods described herein.

The discovery by the present inventor has led to various aspects of the present invention, including, but not limited to, the provision of: isolated peptides encoding the prelamin pre peptide, the prelamin A protein, homologues, mimetics, and fragments thereof, and nucleic acid molecules encoding the same, as therapeutic molecules or compositions for the promotion of myoblast activation and differentiation and for the treatment of cardiac and skeletal muscle disorders; methods to identify compounds useful for the regulation of prelamin A processing and myoblast activation and differentiation; methods to identify genes and proteins in the prelamin A processing pathway and prelamin A pre peptide signal transduction pathway; methods to promote myoblast activation and differentiation and to treat cardiac and skeletal muscle disorders; methods to identify compounds for the treatment of muscle cell cancers and the use of such compounds in therapeutic methods; and prelamin A processing-deficient proteins and cell lines.

According to the present invention, prelamin A is a pre-protein expression product of the lamin A/C gene that is post-translationally processed to yield (1) lamin A and (2) the "pre" peptide. The nucleotide sequence of the cDNA encoding human prelamin C (Database Accession No. NM_005572) is represented herein by SEQ ID NO:7. The cDNA nucleic acid sequence encoding human prelamin A (Database Accession No. NM_170707) is represented here by SEQ ID NO:3. SEQ ID NO:3 encodes the human prelamin A protein that has an amino acid sequence represented herein by SEQ ID NO:4. The nucleic acid and amino acid sequence of prelamin A is also known for a variety of other animal species, including, but not limited to: mouse, chicken, *Xenopus laevis* (African clawed frog), and *Danio rerio* (zebra fish). The nucleic acid sequence of mouse prelamin A (Database Accession No. BC015302) is represented herein by SEQ ID NO:8. SEQ ID NO:8 encodes the mouse prelamin A protein that has an amino acid sequence represented by SEQ ID NO:9. The nucleic acid sequence of chicken prelamin A (Database Accession No. X16879) is represented herein by SEQ ID NO:10. SEQ ID NO:10 encodes the chicken prelamin A protein that has an amino acid sequence represented by SEQ ID NO:11. The nucleic acid sequence of *Xenopus laevis* prelamin A (Database Accession No. X06345) is represented herein by SEQ ID NO:12. SEQ ID NO:12 encodes the *Xenopus laevis* prelamin A protein that has an amino acid sequence represented by SEQ ID NO:13. The nucleic acid sequence of *Danio rerio* prelamin A (Database Accession No. AF397016) is represented herein by SEQ ID NO:14. SEQ ID NO:14 encodes the *Danio rerio* prelamin A protein that has an amino acid sequence represented by SEQ ID NO:15.

Prelamin A processing proceeds through a sequential series of post-translational protein modifications (Sinensky et al., (1994), supra). The cysteine residue in the prelamin A C-terminal CAAX motif (C=Cysteine, A=aliphatic amino acid, X=any amino acid) (e.g., positions 661-664 of SEQ ID NO:4) is farnesylated, followed by the endoproteolytic removal of the C-terminal tripeptide (-AAX). The now C-terminal cysteine residue is carboxymethylated, and finally the C-terminal 15 amino acid peptide (in humans) (i.e., the "pre" peptide) containing the modified cysteine residue (e.g., positions 647-661 of SEQ ID NO:4) is removed by an additional endoproteolytic processing step. The nucleic acid sequence of human lamin A is represented herein by SEQ ID NO:5. SEQ ID NO:5 encodes the lamin A protein having the amino acid sequence represented by SEQ ID NO:6.

The nucleic acid sequence of the processed "pre" peptide from human prelamin A is represented herein by SEQ ID NO:1. SEQ ID NO:1 encodes a 15 amino acid peptide (referred to herein as "pre", "pre peptide", or "prelamin A pre peptide") having an amino acid sequence represented herein by SEQ ID NO:2. One of skill in the art will know, based on the sequence of the prelamin A proteins from other animal species and the knowledge of how the protein is processed, the sequence of the processed lamin A and "pre" peptides corresponding to these other prelamin A proteins. For example, the mouse pre peptide is, by homology to the human pre peptide: LLGNSSPRSQSSQNC (SEQ ID NO:16). The chicken pre peptide has been shown to be: VLGGAGPRRQAPAPQGC (SEQ ID NO:17). The pre peptide for *Xenopus laevis* is, by homology to the human pre peptide: IVGNGQRAQVAPQNC (SEQ ID NO:18). The pre peptide for *Danio rerio* is, by homology to the human pre peptide: IVSNDKPRQAGPKVDNC (SEQ ID NO:19). The sequences of the lamin A and "pre" peptides for any known prelamin A protein or nucleic acid sequence encoding the same are explicitly encompassed by the present invention. The complete sequences represented by each of the sequence database accession numbers recited herein are incorporated herein by reference. An alignment of the prelamin A "pre" peptide amino acid sequences (including the entire CAAX motif that is ultimately processed to reveal a modified cysteine C terminus), is shown in FIG. 2.

Although the embodiments of the invention are discussed below with regard to the human prelamin A and prelamin A pre peptide sequences (e.g., SEQ ID NO:4 and SEQ ID NO:2, respectively), it is to be understood that the present invention expressly encompasses the substitution of sequences of prelamin A or prelamin A pre peptide from any other animal species (including from mouse, chicken, *Xenopus laevis* or *Danio rerio* discussed above) in any of the embodiments described below.

One embodiment of the present invention relates to an isolated peptide selected from: (a) a peptide consisting essentially of SEQ ID NO:2; (b) a biologically active fragment of SEQ ID NO:2; (c) a peptide consisting essentially of an amino acid sequence that is at least about 70% identical to SEQ ID NO:2 with the biological activity of SEQ ID NO:2; and/or (d) a peptide consisting essentially of an amino acid sequence that differs from SEQ ID NO:2 by at least one substitution, deletion or insertion of an amino acid residue at a position of SEQ ID NO:2 selected from the group consisting of: 1, 2, 5, 6, 9, 10, 11, 12, 13 and/or 14, wherein the peptide has the biological activity of SEQ ID NO:2. As discussed above, SEQ ID NO:2 represents the amino acid sequence of a prelamin A pre peptide.

Another embodiment of the present invention relates to an isolated peptide selected from: (a) a protein comprising an amino acid sequence represented by SEQ ID NO:4; (b) a protein comprising biologically active fragment of SEQ ID NO:4; and (c) a protein comprising an amino acid sequence that is at least about 70% identical to SEQ ID NO:4, wherein the protein has prelamin A or lamin A biological activity. In one aspect, this protein is chemically or recombinantly attached to a therapeutic agent that increases the half-life of the protein in cardiac or skeletal muscle tissue. SEQ ID NO:4 represents the amino acid sequence of a prelamin A protein of the invention.

Yet another embodiment of the present invention relates to an isolated peptide that consists essentially of an isolated fragment of SEQ ID NO:4 with inter-nuclear transport domain biological activity, or a biologically active homologue thereof. This fragment would be particularly useful as a carrier (e.g., as a fusion partner or carrier to be linked to a compound) for therapeutic agents for the treatment of cardiac or skeletal muscle disorders. A "carrier" refers to any substance or vehicle suitable for delivering a therapeutic composition useful in a therapeutic method (described below) to a suitable in vivo or ex vivo site. Methods of conjugating or operatively linking the above-described protein or fragment to another protein or to a non-protein compound are well known in the art.

The "pre" peptide of prelamin A is a small, 15 amino acid, naturally occurring, easily synthesized, signaling peptide that specifically promotes proper cardiac and skeletal myoblast fusion, myocyte differentiation, and myocyte organization in adults. Consequently, this peptide is an excellent drug candidate as it will specifically promote cell fusion and regeneration of cardiac and skeletal myocytes damaged by disease or other factors. The peptide could be given in its protein form, or introduced as a cDNA by gene therapy. The prelamin A cDNA is also an excellent candidate for gene therapy of cardiac and skeletal muscle disorders and degeneration (or the protein encoded thereby could be delivered). The present inventor's data shows that this protein is rapidly transferred between the multiple nuclei within a myocyte, and affects the morphology and organization of the transfected myocytes as well as that of adjacent untransfected myocytes. Consequently, the prelamin A cDNA would be a highly potent and efficacious gene therapy treatment.

According to the present invention, an isolated protein or peptide, such as a prelamin A protein or pre peptide, is a protein (including a polypeptide or peptide) that has been removed from its natural milieu (i.e., that has been subject to human manipulation) and can include purified proteins, partially purified proteins, recombinantly produced proteins, and synthetically produced proteins, for example. As such, "isolated" does not reflect the extent to which the protein has been purified. Preferably, an isolated protein such as a prelamin A protein of the present invention is produced recombinantly. An isolated peptide, such as the pre peptide, can be produced synthetically (e.g., chemically, such as by peptide synthesis) or recombinantly. In addition, and by way of example, a "human prelamin A protein" refers to a prelamin A protein (generally including a homologue of a naturally occurring prelamin A protein) from a human (*Homo sapiens*), or to a prelamin A protein that has been otherwise produced from the knowledge of the structure (e.g., sequence), and perhaps the function, of a naturally occurring prelamin A protein from *Homo sapiens*. In other words, general reference to a human prelamin A protein includes any prelamin A protein that has substantially similar structure and function of a naturally occurring prelamin A protein from *Homo sapiens* or that is a biologically active (i.e., has biological activity) homologue of a naturally occurring prelamin A protein from *Homo sapiens* as described in detail herein. As such, a human prelamin A protein can include purified, partially purified, recombinant, mutated/modified and synthetic proteins. The same description applies to reference to other proteins or peptides described herein, such as the pre peptide of prelamin A.

According to the present invention, the terms "modification" and "mutation" can be used interchangeably, particularly with regard to the modifications/mutations to the primary amino acid sequences of prelamin A or pre (or nucleic acid sequences) described herein. The term "modification" can also be used to describe post-translational modifications to a protein or peptide including, but not limited to, methylation, farnesylation, carboxymethylation, geranyl geranylation, glycosylation, phosphorylation, acetylation, myristoylation, prenylation, palmitation, and/or amidation. Modifications can also include, for example, complexing a protein or peptide with a lipid carrier. Such modifications can be considered to be mutations if the modification is different than the post-translational modification that occurs in the natural, wild-type protein or peptide.

As used herein, the term "homologue" is used to refer to a protein or peptide which differs from a naturally occurring protein or peptide (i.e., the "prototype" or "wild-type" protein) by one or more minor modifications or mutations to the naturally occurring protein or peptide, but which maintains the overall basic protein and side chain structure of the naturally occurring form (i.e., such that the homologue is identifiable as being related to the wild-type protein). Such changes include, but are not limited to: changes in one or a few amino acid side chains; changes one or a few amino acids, including deletions (e.g., a truncated version of the protein or peptide) insertions and/or substitutions; changes in stereochemistry of one or a few atoms; and/or minor derivatizations, including but not limited to: methylation, farnesylation, geranyl geranylation, glycosylation, carboxymethylation, phosphorylation, acetylation, myristoylation, prenylation, palmitation, and/or amidation. A homologue can have either enhanced, decreased, or substantially similar properties as compared to the naturally occurring protein or peptide. A homologue can include an agonist of a protein or peptide or an antagonist of a protein or peptide.

Homologues can be the result of natural allelic variation or natural mutation. A naturally occurring allelic variant of a nucleic acid encoding a protein is a gene that occurs at essentially the same locus (or loci) in the genome as the gene which encodes such protein, but which, due to natural variations caused by, for example, mutation or recombination, has a similar but not identical sequence. Allelic variants typically encode proteins having similar activity to that of the protein encoded by the gene to which they are being compared. One class of allelic variants can encode the same protein but have different nucleic acid sequences due to the degeneracy of the genetic code. Allelic variants can also comprise alterations in the 5' or 3' untranslated regions of the gene (e.g., in regulatory control regions). Allelic variants are well known to those skilled in the art.

Homologues can be produced using techniques known in the art for the production of proteins including, but not limited to, direct modifications to the isolated, naturally occurring protein, direct protein synthesis, or modifications to the nucleic acid sequence encoding the protein using, for example, classic or recombinant DNA techniques to effect random or targeted mutagenesis.

Modifications in protein homologues, as compared to the wild-type protein, either agonize, antagonize, or do not substantially change, the basic biological activity of the homologue as compared to the naturally occurring (wild-type) protein. In general, the biological activity or biological action of a protein refers to any function(s) exhibited or performed by the protein that is ascribed to the naturally occurring form of the protein as measured or observed in vivo (i.e., in the natural physiological environment of the protein) or in vitro (i.e., under laboratory conditions). Modifications of a protein, such as in a homologue or mimetic (discussed below), may result in proteins having the same biological activity as the naturally occurring protein, or in proteins having decreased or increased biological activity as compared to the naturally occurring protein. Modifications which result in a decrease in protein expression or a decrease in the activity of the protein, can be referred to as inactivation (complete or partial), down-regulation, or decreased action (or activity) of a protein. Similarly, modifications which result in an increase in protein expression or an increase in the activity of the protein, can be referred to as amplification, overproduction, activation, enhancement, up-regulation or increased action (or activity) of a protein. It is noted that general reference to a homologue having the biological activity of the wild-type protein does not necessarily mean that the homologue has identical biological activity as the wild-type protein, particularly with regard to the level of biological activity. Rather, a homologue can perform the same biological activity as the wild-type protein, but at a reduced or increased level of activity as compared to the wild-type protein.

According to the present invention, an isolated prelamin A protein or an isolated pre peptide (or other isolated protein described herein), including a biologically active homologue or fragment thereof, has at least one characteristic of biological activity of activity the wild-type, or naturally occurring protein (which can vary depending on whether the homologue or fragment is an agonist, antagonist, or mimic of the wild-type protein). The biological activity of prelamin A can include any activity of the pre peptide or of the lamin peptide, including, but not limited to: expression of prelamin A or pre peptide; processing of prelamin A to release the pre peptide and lamin; pre peptide signal transduction, synchronization of intercellular signaling with changes in lamin A localization and nuclear lamina morphology that occur early in myoblast differentiation, synchronization of transcriptional regulation of muscle-specific genes or cell cycle arrest that occurs concomitant with myoblast differentiation, induction of myoblast activation and differentiation, and incorporation of lamin A into the nuclear lamina structure.

Methods of detecting and measuring prelamin A or pre peptide biological activity (which can be applied appropriately to measure agonist or antagonist activity) include, but are not limited to, measurement of transcription of prelamin A, measurement of translation of prelamin A, measurement of posttranslational modification of prelamin A, measurement of processing of the pre peptide, measurement of pre peptide signal transduction, measurement of lamin A incorporation into the nuclear lamina structure, measurement of transcriptional regulation of muscle-specific genes and/or cell cycle arrest, measurement of nuclear lamina morphology, measurement of pre peptide transport, measurement of lamin A localization, measurement of myocyte cell fusion, and/or measurement of myoblast activation and differentiation. It is noted that an isolated protein of the present invention (including homologues) is not necessarily required to have the biological activity of the wild-type protein. For example, a prelamin A protein can be a truncated, mutated or inactive protein, for example. Such proteins are useful in diagnostic assays or some screening assays, for example, or for other purposes such as antibody production. In a preferred embodiment, the isolated proteins of the present invention (e.g., prelamin A or pre peptide) have biological activity that is similar to that of the wild-type protein (although not necessarily equivalent, as discussed above).

Methods to measure protein expression levels of this invention include, but are not limited to: Western blot, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, fluorescence activated cell sorting (FACS), and flow cytometry, as well as assays based on a property of the protein including but not limited to DNA binding, ligand binding, or interaction with other protein partners. Binding assays are also well known in the art. For example, a BIAcore machine can be used to determine the binding constant of a complex between two proteins. The dissociation constant for the complex can be determined by monitoring changes in the refractive index with respect to time as buffer is passed over the chip (O'Shannessy et al. Anal. Biochem. 212:457-468 (1993); Schuster et al., Nature 365:343-347 (1993)). Other suitable assays for measuring the binding of one protein to another include, for example, immunoassays such as enzyme linked immunoabsorbent assays (ELISA) and radioimmunoassays (RIA); or determination of binding by monitoring the change in the spectroscopic or optical properties of the proteins through fluorescence, UV absorption, circular dichrosim, or nuclear magnetic resonance (NMR). To evaluate whether two proteins interact, two hybrid assays (e.g., yeast two hybrid assays) are useful and are particularly useful for identifying proteins (gene products) that interact with prelamin A or pre peptide.

As used herein, an "agonist" of a protein or peptide of the invention refers to any compound that is characterized by the ability to agonize (e.g., stimulate, induce, increase, enhance, or mimic) the biological activity of the naturally occurring (wild-type) protein as described herein. More particularly, an agonist can include, but is not limited to, a protein, peptide, or nucleic acid that stimulates, induces, mimics or enhances the activity of the natural ligand, (e.g., prelamin A or pre peptide), and includes homologue of the wild-type protein, a binding protein (e.g., an antibody), or any suitable product of drug/compound/peptide design or selection which is characterized by its ability to agonize (e.g., stimulate, induce, increase, enhance) the biological activity of a naturally occurring protein. Agonists can be useful in methods for regulating myoblast activation and/or the growth or regeneration of cardiac or skeletal muscle.

The phrase, "antagonist" refers to any compound which inhibits (e.g., antagonizes, reduces, decreases, blocks, reverses, or alters) the effect of a naturally occurring or wild-type protein of the invention or of an agonist thereof, as described above. More particularly, an antagonist is capable of associating with proteins or other compounds in a manner similar to the wild-type protein, or otherwise acts in a manner relative to the activity of the wild-type protein, such that the biological activity of the wild-type protein is decreased or blocked in a manner that is antagonistic (e.g., against, a reversal of, contrary to) to the natural action of wild-type protein. Such antagonists can include, but are not limited to, a protein, peptide, or nucleic acid (including ribozymes and antisense) or product of drug/compound/peptide design or selection that provides the antagonistic effect. Antagonists can be useful, for example, in methods for treatment of muscle cell cancers and metastatic cancers thereof.

According to the present invention, a ribozyme typically contains stretches of complementary RNA bases that can base-pair with a target RNA ligand, including the RNA molecule itself, giving rise to an active site of defined structure that can cleave the bound RNA molecule (See Maulik et al., 1997, supra). Therefore, a ribozyme can serve as a targeting delivery vehicle for a nucleic acid molecule, or alternatively, the ribozyme can target and bind to RNA encoding prelamin A, for example, and thereby effectively inhibit the translation of prelamin A.

As used herein, an anti-sense nucleic acid molecule is defined as an isolated nucleic acid molecule that reduces expression of a protein by hybridizing under high stringency conditions to a gene encoding the protein (including to regulatory regions of the gene encoding the protein). Such a nucleic acid molecule is sufficiently similar to the nucleic acid sequence encoding the protein that the molecule is capable of hybridizing under high stringency conditions to the coding strand of the gene or RNA encoding the natural protein. In a particularly preferred embodiment, an anti-sense nucleic acid molecule of the present invention is the exact complement of the regulatory region or the coding region of the protein. It is noted that the anti-sense of the coding region does not necessarily include the anti-sense of the stop codon.

Homologues of prelamin A or pre peptide, including peptide and non-peptide agonists and antagonists of prelamin A or pre peptide, can be products of drug design or selection and can be produced using various methods known in the art. Such homologues can be referred to as mimetics. A mimetic refers to any peptide or non-peptide compound that is able to mimic the biological action of a naturally occurring peptide, often because the mimetic has a basic structure that mimics the basic structure of the naturally occurring peptide and/or has the salient biological properties of the naturally occurring peptide. Mimetics can include, but are not limited to: peptides that have substantial modifications from the prototype such as no side chain similarity with the naturally occurring peptide (such modifications, for example, may decrease its susceptibility to degradation); anti-idiotypic and/or catalytic antibodies, or fragments thereof; non-proteinaceous portions of an isolated protein (e.g., carbohydrate structures); or synthetic or natural organic molecules, including nucleic acids and drugs identified through combinatorial chemistry, for example. Such mimetics can be designed, selected and/or otherwise identified using a variety of methods known in the art. Various methods of drug design, useful to design or select mimetics or other therapeutic compounds useful in the present invention are disclosed in Maulik et al., 1997, *Molecular Biotechnology: Therapeutic Applications and Strategies*, Wiley-Liss, Inc., which is incorporated herein by reference in its entirety.

A mimetic can be obtained, for example, from molecular diversity strategies (a combination of related strategies allowing the rapid construction of large, chemically diverse molecule libraries), libraries of natural or synthetic compounds, in particular from chemical or combinatorial libraries (i.e., libraries of compounds that differ in sequence or size but that have the similar building blocks) or by rational, directed or random drug design. See for example, Maulik et al., supra.

In a molecular diversity strategy, large compound libraries are synthesized, for example, from peptides, oligonucleotides, carbohydrates and/or synthetic organic molecules, using biological, enzymatic and/or chemical approaches. The critical parameters in developing a molecular diversity strategy include subunit diversity, molecular size, and library diversity. The general goal of screening such libraries is to utilize sequential application of combinatorial selection to obtain high-affinity ligands for a desired target, and then to optimize the lead molecules by either random or directed design strategies. Methods of molecular diversity are described in detail in Maulik, et al., ibid.

Maulik et al. also disclose, for example, methods of directed design, in which the user directs the process of creating novel molecules from a fragment library of appropriately selected fragments; random design, in which the user uses a genetic or other algorithm to randomly mutate fragments and their combinations while simultaneously applying a selection criterion to evaluate the fitness of candidate ligands; and a grid-based approach in which the user calculates the interaction energy between three dimensional receptor structures and small fragment probes, followed by linking together of favorable probe sites.

In one embodiment of the present invention, a prelamin A protein has an amino acid sequence that comprises, consists essentially of, or consists of, SEQ ID NO:4. SEQ ID NO:4 represents a human prelamin A protein (encoded by nucleic acid sequence SEQ ID NO:3). The present invention also includes homologues of SEQ ID NO:4, or fragments of SEQ ID NO:4, wherein the homologue or fragment has prelamin A biological activity (including agonist or antagonist activity), as described previously herein.

In one embodiment of the present invention, a pre peptide of prelamin A has an amino acid sequence that comprises, consists essentially of, or consists of, SEQ ID NO:2. SEQ ID NO:2 represents a human pre peptide (encoded by SEQ ID NO:1). The present invention also includes homologues of SEQ ID NO:2 or fragments of SEQ ID NO:2, wherein the homologue or fragment has pre peptide biological activity (including agonist or antagonist activity), as described previously herein and as described in more detail below.

In one embodiment, a pre peptide or a prelamin A protein of the present invention, including a homologue thereof, has an amino acid sequence that is at least about 50% identical to an amino acid sequence of SEQ ID NO:2 or SEQ ID NO:4, respectively, over the full length of any of such sequences, wherein the protein has pre peptide or prelamin A biological activity (which can include agonist or antagonist activity), respectively. In another embodiment, a pre peptide or a prelamin A protein useful in the present invention has an amino acid sequence that is at least about 55% identical, or at least about 60% identical, or at least about 65% identical, or at least about 70% identical, or at least about 75% identical, or at least about 80% identical, or at least about 85% identical, or at least about 90% identical, or at least about 95% identical, or at least about 96% identical, or at least about 97% identical, or at least about 98% identical, or at least about 99% identical to SEQ ID NO:2 or SEQ ID NO:4, respectively, over the full length of any of such sequences.

In one embodiment of the present invention, a homologue of a protein, such as a prelamin A protein or a prelamin A pre peptide according to the present invention has an amino acid sequence that is less than about 100% identical to the wild-type sequence (e.g., SEQ ID NO:4 or SEQ ID NO:2). In another aspect of the invention, a homologue according to the present invention has an amino acid sequence that is less than about 99% identical to the wild-type amino acid sequence, and in another embodiment, is less than is less than 98% identical to the wild-type amino acid sequence, and in another embodiment, is less than 97% identical to the wild-type amino acid sequence, and in another embodiment, is less than 96% identical to the wild-type amino acid sequence, and in another embodiment, is less than 95% identical to the wild-type amino acid sequence, and in another embodiment, is less than 94% identical to the wild-type amino acid sequence, and in another embodiment, is less than 93% identical to the wild-type amino acid sequence, and in another embodiment, is less than 92% identical to the wild-type amino acid sequence, and in another embodiment, is less than 91% identical to the wild-type amino acid sequence, and in another embodiment, is less than 90% identical to the wild-type amino acid sequence, and so on, in increments of whole integers.

As used herein, unless otherwise specified, reference to a percent (%) identity refers to an evaluation of homology which is performed using: (1) a BLAST 2.0 Basic BLAST homology search using blastp for amino acid searches, blastn for nucleic acid searches, and blastX for nucleic acid searches and searches of translated amino acids in all 6 open reading frames, all with standard default parameters, wherein the query sequence is filtered for low complexity regions by default (described in Altschul, S. F., Madden, T. L., Schääffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402, incorporated herein by reference in its entirety); (2) a BLAST 2 alignment (using the parameters described below); (3) and/or PSI-BLAST with the standard default parameters (Position-Specific Iterated BLAST). It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second sequence in the top matches. In addition, PSI-BLAST provides an automated, easy-to-use version of a "profile" search, which is a sensitive way to look for sequence homologues. The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using any one of these programs.

Two specific sequences can be aligned to one another using BLAST 2 sequence as described in Tatusova and Madden, (1999), "Blast 2 sequences—a new tool for comparing protein and nucleotide sequences", *FEMS Microbiol Lett.* 174:247-250, incorporated herein by reference in its entirety. BLAST 2 sequence alignment is performed in blastp or blastn using the BLAST 2.0 algorithm to perform a Gapped BLAST search (BLAST 2.0) between the two sequences allowing for the introduction of gaps (deletions and insertions) in the resulting alignment. For purposes of clarity herein, a BLAST 2 sequence alignment is performed using the standard default parameters as follows.

For blastn, using 0 BLOSUM62 matrix:
  Reward for match=1
  Penalty for mismatch=−2
  Open gap (5) and extension gap (2) penalties
  gap x_dropoff (50) expect (10) word size (11) filter (on)
For blastp, using 0 BLOSUM62 matrix:
  Open gap (11) and extension gap (1) penalties
  gap x_dropoff (50) expect (10) word size (3) filter (on).

According to the present invention, the term "contiguous" or "consecutive", with regard to nucleic acid or amino acid sequences described herein, means to be connected in an unbroken sequence. For example, for a first sequence to comprise 30 contiguous (or consecutive) amino acids of a second sequence, means that the first sequence includes an unbroken sequence of 30 amino acid residues that is 100% identical to an unbroken sequence of 30 amino acid residues in the second sequence. Similarly, for a first sequence to have "100% identity" with a second sequence means that the first sequence exactly matches the second sequence with no gaps between nucleotides or amino acids.

In another embodiment, a pre peptide homologue or a prelamin A homologue includes a protein having an amino acid sequence that is sufficiently similar to a naturally occurring pre peptide or prelamin A amino acid sequence, respectively, that a nucleic acid sequence encoding the homologue is capable of hybridizing under moderate, high, or very high stringency conditions (described below) to (i.e., with) a nucleic acid molecule encoding the naturally occurring protein (i.e., to the complement of the nucleic acid strand encoding the naturally occurring amino acid sequence). Preferably, a protein useful in the invention, including a homologue, is encoded by a nucleic acid sequence that hybridizes under moderate, high or very high stringency conditions to the complement of a nucleic acid sequence that encodes a protein comprising an amino acid sequence represented by SEQ ID NO:2 or SEQ ID NO:4. Even more preferably, a protein useful in the present invention, including a homologue, is encoded by a nucleic acid sequence that hybridizes under moderate, high or very high stringency conditions to the complement of the coding region of a nucleic acid sequence selected from SEQ ID NO:1 or SEQ ID NO:3, or fragments thereof. Such hybridization conditions are described in detail below. A nucleic acid sequence complement of nucleic acid sequence encoding a protein useful in the present invention refers to the nucleic acid sequence of the nucleic acid strand that is complementary to the strand which encodes the protein. It will be appreciated that a double stranded DNA which encodes a given amino acid sequence comprises a single strand DNA and its complementary strand having a sequence that is a complement to the single strand DNA. As such, nucleic acid molecules of the present invention can be either double-stranded or single-stranded, and include those nucleic acid molecules that form stable hybrids under stringent hybridization conditions with a nucleic acid sequence that encodes an amino acid sequence of pre peptide or prelamin A, for example, and/or with the complement of the nucleic acid sequence that encodes any of such amino acid sequences. Methods to deduce a complementary sequence are known to those skilled in the art. It should be noted that since amino acid sequencing and nucleic acid sequencing technologies are not entirely error-free, the sequences presented herein, at best, represent apparent sequences of pre peptide and prelamin A of the present invention.

As used herein, reference to hybridization conditions refers to standard hybridization conditions under which nucleic acid molecules are used to identify similar nucleic acid molecules. Such standard conditions are disclosed, for example, in Sambrook et al., *Molecular Cloning: A Laboratory Manual*, Cold Spring Harbor Labs Press, 1989. Sambrook et al., ibid., is incorporated by reference herein in its entirety (see specifically, pages 9.31-9.62). In addition, formulae to calculate the appropriate hybridization and wash conditions to achieve hybridization permitting varying degrees of mismatch of nucleotides are disclosed, for example, in Meinkoth et al., 1984, *Anal. Biochem.* 138, 267-284; Meinkoth et al., ibid., is incorporated by reference herein in its entirety.

More particularly, moderate stringency hybridization and washing conditions, as referred to herein, refer to conditions which permit isolation of nucleic acid molecules having at least about 70% nucleic acid sequence identity with the nucleic acid molecule being used to probe in the hybridization reaction (i.e., conditions permitting about 30% or less mismatch of nucleotides). High stringency hybridization and washing conditions, as referred to herein, refer to conditions which permit isolation of nucleic acid molecules having at least about 80% nucleic acid sequence identity with the nucleic acid molecule being used to probe in the hybridization reaction (i.e., conditions permitting about 20% or less mismatch of nucleotides). Very high stringency hybridization and washing conditions, as referred to herein, refer to conditions which permit isolation of nucleic acid molecules having at least about 90% nucleic acid sequence identity with the nucleic acid molecule being used to probe in the hybridization reaction (i.e., conditions permitting about 10% or less mismatch of nucleotides). As discussed above, one of skill in the art can use the formulae in Meinkoth et al., ibid. to calculate the appropriate hybridization and wash conditions to achieve these particular levels of nucleotide mismatch. Such conditions will vary, depending on whether DNA:RNA or DNA:DNA hybrids are being formed. Calculated melting temperatures for DNA:DNA hybrids are 10° C. less than for DNA:RNA hybrids. In particular embodiments, stringent hybridization conditions for DNA:DNA hybrids include hybridization at an ionic strength of 6×SSC (0.9 M Na$^+$) at a temperature of between about 20° C. and about 35° C. (lower stringency), more preferably, between about 28° C. and about 40° C. (more stringent), and even more preferably, between about 35° C. and about 45° C. (even more stringent), with appropriate wash conditions. In particular embodiments, stringent hybridization conditions for DNA:RNA hybrids include hybridization at an ionic strength of 6×SSC (0.9 M Na$^+$) at a temperature of between about 30° C. and about 45° C., more preferably, between about 38° C. and about 50° C., and even more preferably, between about 45° C. and about 55° C., with similarly stringent wash conditions. These values are based on calculations of a melting temperature for molecules larger than about 100 nucleotides, 0% formamide and a G+C content of about 40%. Alternatively, $T_m$ can be calculated empirically as set forth in Sambrook et al., supra, pages 9.31 to 9.62. In general, the wash conditions should be as stringent as possible, and should be appropriate for the chosen hybridization conditions. For example, hybridization conditions can include a combination of salt and temperature conditions that are approximately 20-25° C. below the calculated $T_m$ of a particular hybrid, and wash conditions typically include a combination of salt and temperature conditions that are approximately 12-20° C. below the calculated $T_m$ of the particular hybrid. One example of hybridization conditions suitable for use with DNA:DNA hybrids includes a 2-24 hour hybridization in 6×SSC (50% formamide) at about 42° C., followed by washing steps that include one or more washes at room temperature in about 2×SSC, followed by additional washes at higher temperatures and lower ionic strength (e.g., at least one wash as about 37° C. in about 0.1×-0.5×SSC, followed by at least one wash at about 68° C. in about 0.1×-0.5×SSC).

In another embodiment of the invention, a homologue of a prelamin A protein or a pre peptide can include at least one modification to a specific amino acid residue of the wild-type sequence, wherein the resulting homologue preferably retains a biological activity of the wild-type protein or peptide. Particularly preferred modifications include at least one substitution, deletion, or insertion of an amino acid residue for an amino acid residue that does not, or is predicted not to, substantially affect the biological activity of the protein. Referring to FIG. 2, the present inventor has aligned the prelamin A pre peptide (including the ultimately cleaved -AAX motif from prelamin A, described above) to show the conserved amino acid positions relative to the human sequence. Based on such an alignment, one of skill in the art can readily predict which amino acid positions are most likely to tolerate substitution, modification, insertion or deletion, and whether substitutions or additions should be conservative or less conservative.

For example, from the alignment provided in FIG. 2, it is clear that the human sequence (positions 647-664 of SEQ ID NO:4; represented by SEQ ID NO:20) is most closely related to the mouse (positions 648-665 of SEQ ID NO:9; represented by SEQ ID NO:21) and chicken sequence (positions 638-657 of SEQ ID NO:11; represented by SEQ ID NO:22), and less so to frog (positions 648-665 of SEQ ID NO:13; represented by SEQ ID NO:23) and fish (positions 640-659 of SEQ ID NO:15; represented by SEQ ID NO:24), as would be expected based on taxonomy. With reference to the human sequence shown in FIG. 2, since the amino acid position of relative to human T9 (threonine at position 9 of SEQ ID NO:20) is not conserved in any species, the substitutions of serine, arginine®) and glutamic acid (Q) for this amino acid sequence of other species are unlikely to have an effect and therefore, this position is likely to tolerate a variety of substitutions or other modifications. The substitutions seen in chicken, frog and fish for human S5, S6, Q10 and S11 are more intermediate in terms of the type of substitution at this position between species, and so one could make more conservative, but not necessarily very conservative, substitutions or modifications at these positions with a reasonable expectation of avoiding significantly altering protein activity or processing. The alignment indicates that modifications could also be made at positions relative to human L1 and L2. However, since the differences among species at these positions are very conservative (e.g., a valine or isoleucine for a leucine), one would preferably limit modifications at this position to the most conservative possibilities (e.g., one would typically avoid substitution of a polar or charged amino acid at these aliphatic positions, but favor substitutions of other aliphatic amino acids such as valine or isoleucine for the leucine residue). The positions relative to human G3, N4, P7, R8, P12, Q13, N14, C15, S16, I17 and M18 are conserved in 4 of the 5 species, or in all 5 species. Substitutions in these amino acids would be the most likely to affect protein activity and/or processing, although as discussed below, substitutions or modifications at these positions are not excluded in the present invention.

In general, one could use the following guidelines with reference to the human sequence (SEQ ID NO:20). L1 and L2 are conservatively substituted among other species and so good choices for substitution would be other aliphatic amino acids. G3 is only non-conservatively substituted in zebrafish, and would be an unlikely choice for substitutions that would not affect activity. N4 is only nonconservatively substituted in chicken and would be a weak choice. S5 is conservatively substituted in chicken, zebrafish and frog, and the S6 is nonconservatively substituted in these three species. Therefore, both serines (S5 and S6) would be intermediate sites for substitutions. P7 and R8 are only non-conservatively substituted in *Xenopus* and would be weak targets, while the following T9 is nonconservatively substituted in all 4 species, making it the strongest target for substitutions that are not predicted to affect activity. Q10 has nonconservative substitutions in zebrafish and frog, making it an intermediate candidate, while S11 is nonconservatively substituted in chick, fish and frog, making it an intermediate candidate as well. P12 has a conservative substitution to an S in mouse only, indicating this particular amino acid change may not affect activity, but other changes at this residue would be predicted to affect activity. Q13 has a conservative substitution in zebrafish only, making it a poor choice, and the following N14 has a nonconservative substitution in chicken only, indicating it is not a preferred position for substitutions. The final CSIM (positions 15-18 of SEQ ID NO:20 in FIG. 2, corresponding to positions 661-664 of SEQ ID NO:4) is the CAAX motif, and is conserved through all species, indicating it is not normally modified. However, because the -AAX motif is known to be degenerate regarding the ability to direct farnesylation, the present inventor envisions the possibility of making substitutions in these amino acids, particularly with regard to embodiments directed to modifying the farnesylation processing steps of prelamin A.

Finally, it is to be understood that while positions that contain the most variability across species are the most likely to be mutated without effect, any substitution which occurs between species may be conservative functionally. Therefore, even though there are only single substitutions in each of the P12, Q13 and N14 amino acids at the end of the human sequence (SEQ ID NO:20), one might want to introduce these single amino acid substitutions in the human sequence because they have low probabilities of affecting activity.

Preferred amino acid residues of the human prelamin A pre peptide sequence for modification include, but are not limited to: 1, 2, 5, 6, 9, 10, 11, 12, 13 and/or 14, with modifications at positions 1, 2, 5, 6, 9, 10, 11 and/or 12 being more preferred, and modifications at positions 1, 2, 5, 6, 9, 10 and/or 11 being particularly preferred.

Conservative substitutions typically include substitutions within the following groups: glycine and alanine; valine, isoleucine and leucine; aspartic acid, glutamic acid, asparagine, and glutamine; serine and threonine; lysine and arginine; and phenylalanine and tyrosine. Substitutions may also be made on the basis of conserved hydrophobicity or hydrophilicity (Kyte and Doolittle, *J. Mol. Biol.* (1982) 157: 105-132), or on the basis of the ability to assume similar polypeptide secondary structure (Chou and Fasman, *Adv. Enzymol.* (1978) 47: 45-148, 1978).

In another aspect of the invention, it is desirable to produce a homologue of prelamin A that is processing deficient. In this aspect, preferred amino acid residues for) modification include, but are not limited to (with reference to SEQ ID NO:4), any residues that are rarely substituted across species, Arg60, Leu85, Glu203, Arg89, Asn195, Arg377, Tyr646, G649, N650, P653, R654, P658, Q659, N660, Cys661, S662, I663 and/or M664. It is to be understood that modifications are not limited to these positions of SEQ ID NO:4, as one of skill in the art will readily be able to select other positions that are likely to tolerate at least a conservative amino acid substitution, if not moderate to any amino acid substitution. In one aspect, the amino acids are substituted for different amino acid residues as follows: Arg60Gly, Leu85Arg, Glu203Gly, Arg89Leu, Asn195Lys, and Arg377His.

The minimum size of a protein and/or homologue of the present invention is, in one aspect, a size sufficient to have the requisite biological activity, including agonist or antagonist activity, or sufficient to serve as an antigen for the generation of an antibody or as a target or detectable reagent in an in vitro assay. In one embodiment, a pre peptide of the present invention is at least about 8 amino acids in length, or at least about 9 amino acids in length, or at least about 10 amino acids in length, or at least about 11 amino acids in length, or at least about 12 amino acids in length, or at least about 13 amino acids in length, or at least about 14 amino acids in length, or at least about 15 amino acids in length. There is no limit, other than a practical limit, on the maximum size of such a protein in that the protein can include a portion of a pre peptide or a full-length pre peptide, plus additional sequence (e.g., a fusion protein sequence), if desired.

In one embodiment, a prelamin A protein of the present invention is at least about 8 amino acids in length (e.g., suitable for an antibody epitope or as a detectable reagent in an assay), or at least about 25 amino acids in length, or at least about 50 amino acids in length, or at least about 100 amino acids in length, or at least about 150 amino acids in length, or at least about 200 amino acids in length, or at least about 250 amino acids in length, or at least about 300 amino acids in length, or at least about 350 amino acids in length, or at least about 400 amino acids in length, or at least about 450 amino acids in length, or at least about 500 amino acids in length, or at least about 550 amino acids in length, or at least about 600 amino acids in length. Again, there is no limit, other than a practical limit, on the maximum size of such a protein in that the protein can include a portion of a prelamin A protein or a full-length prelamin A protein, plus additional sequence (e.g., a fusion protein sequence), if desired.

Another embodiment of the invention relates to a fragment of prelamin A consisting essentially of a domain of prelamin A that has inter-nuclear transport domain biological activity, or a biologically active homologue thereof. The present inventor has shown that prelamin A is rapidly transferred between nuclei within the myocyte, increasing its efficacy. The use of the inter-nuclear transport domain as a targeting moiety for other pharmaceuticals would increase their efficacy without introducing toxicity. To identify the exact sequence of the transport domain will be straightforward. Briefly, in order to identify the lamin A protein sequences responsible for internuclear transport, deletion-mapping experiments will be performed on the wild type prelamin A GFP-fusion protein construct. Initially, restriction enzymes will be used to create large, overlapping deletions in the prelamin A cDNA sequence. For example, C2C12 myoblasts will be transfected with the deletion constructs and induced to differentiate. Protein regions responsible for internuclear transport will be identified as those which prevent internuclear transport of the GFP fusion protein when deleted. Once the region encoding the transport domain is identified, site-directed mutagenesis will be used to delineate the minimal protein sequence necessary for internuclear protein transport.

Complementary experiments will be performed in which the regions deleted from the prelamin A cDNA in the experiments described above will be cloned downstream of GFP coding sequences in a plasmid which does not contain any other prelamin A coding sequences. The ability of the cloned prelamin A subsequences to direct internuclear transport when fused directly to GFP will be assessed by transfecting C2C12 myoblasts with the plasmid expression constructs and examining the expression of GFP within the nuclei of myotubes. These experiments will confirm the functional role of protein transport sequences identified by deletion mapping, and allow for the analysis of peptide sequences that may result in protein degradation when deleted from the full-length prelamin A protein.

The present invention also includes a fusion protein that includes a pre peptide-, prelamin A-, or prelamin A inter-nuclear transport domain-containing segment (i.e., an amino acid sequence for a pre peptide, a prelamin A protein, or a prelamin A inter-nuclear transport domain according to the present invention, including homologues and fragments thereof) attached to one or more fusion segments. Suitable fusion segments for use with the present invention include, but are not limited to, segments that can: enhance a protein's stability; provide other desirable biological activity (e.g., a therapeutic protein/peptide to be delivered to a site); and/or assist with the purification of the protein (e.g., by affinity chromatography). A suitable fusion segment can be a domain of any size that has the desired function (e.g., imparts increased stability, solubility, biological activity; and/or simplifies purification of a protein). Fusion segments can be joined to amino and/or carboxyl termini of the pre peptide-, prelamin A-, or prelamin A inter-nuclear transport domain-containing segment of the protein and can be susceptible to cleavage in order to enable straight-forward recovery of the desired protein. Fusion proteins are preferably produced by culturing a recombinant cell transfected with a fusion nucleic acid molecule that encodes a protein including the fusion segment attached to either the carboxyl and/or amino terminal end of a pre peptide-, prelamin A-, or prelamin A inter-nuclear transport domain-containing segment.

In one aspect, a prelamin A inter-nuclear transport domain is a therapeutic composition for promoting myoblast activation and growth or regeneration of cardiac or skeletal muscle, comprising an isolated peptide consisting essentially of an isolated fragment of SEQ ID NO:4 with inter-nuclear transport domain activity or a biologically active homologue thereof. The peptide is fused to a therapeutic protein for promoting myoblast activation and growth or regeneration of cardiac or skeletal muscle, or to a drug for use in the treatment of heart and skeletal muscle diseases. Fusion to the transport domain will likely increase the efficacy of drugs with nuclear functions, and may also increase the distribution of drugs that do not have specifically nuclear functions. There are currently no treatments for muscular dystrophies, although gene therapy has been proposed using emerin, dystrophin and other genes known to be mutated in these diseases. Therefore, fusion of the prelamin A transport domain to such genes could enhance these putative therapies. For cardiomyopathies, one treatment currently includes the use of "beta blockers" to block the beta adrenergic response pathway. However, the exact mechanism of action is not known, as there is some evidence that certain beta-blockers (carvedilol) may be efficacious due to their antioxidant activity. As beta-blockers are the primary therapy for cardiomyopathies, the present invention includes the fusion of the prelamin A transport domain to such drugs. The invention intends to encompass the use of any drugs that are used to treat other heart diseases, which could benefit from the transport domain.

In one embodiment of the present invention, any of the amino acid sequences described herein can be produced with from at least one, and up to about 20, additional heterologous amino acids flanking each of the C- and/or N-terminal ends of the specified amino acid sequence (the specified amino acid sequence being, for example, SEQ ID NO:2, SEQ ID NO:4, a biologically active fragment thereof or a biologically active homologue thereof). The resulting protein or polypeptide can be referred to as "consisting essentially of" the specified amino acid sequence. According to the present invention, the heterologous amino acids are a sequence of amino acids that are not naturally found (i.e., not found in nature, in vivo) flanking the specified amino acid sequence, or that are not related to the function of the specified amino acid sequence, or that would not be encoded by the nucleotides that flank the naturally occurring nucleic acid sequence encoding the specified amino acid sequence as it occurs in the gene, if such nucleotides in the naturally occurring sequence were translated using standard codon usage for the organism from which the given amino acid sequence is derived. Similarly, the phrase "consisting essentially of", when used with reference to a nucleic acid sequence herein, refers to a nucleic acid sequence encoding a specified amino acid sequence that can be flanked by from at least one, and up to as many as about 60, additional heterologous nucleotides at each of the 5' and/or the 3' end of the nucleic acid sequence encoding the specified amino acid sequence. The heterologous nucleotides are not naturally found (i.e., not found in nature, in vivo) flanking the nucleic acid sequence encoding the specified amino acid sequence as it occurs in the natural gene or do not encode a protein that imparts an additional function to the protein or changes the function of the protein having the specified amino acid sequence.

Another embodiment of the present invention relates to a composition comprising at least about 500 ng, and preferably at least about 1 µg, and more preferably at least about 5 µg, and more preferably at least about 10 µg, and more preferably at least about 25 µg, and more preferably at least about 50 µg, and more preferably at least about 75 µg, and more preferably at least about 100 µg, and more preferably at least about 250 µg, and more preferably at least about 500 µg, and more preferably at least about 750 µg, and more preferably at least about 1 mg, and more preferably at least about 5 mg, of an isolated pre peptide or a prelamin A protein comprising any of the proteins, fragments thereof or homologues thereof discussed herein (including, for example, a fragment having the prelamin A inter-nuclear transport domain biological activity). Such a composition of the present invention can include any carrier with which the protein is associated by virtue of the protein preparation method, a protein purification method, or a preparation of the protein for use in an in vitro, ex vivo, or in vivo method according to the present invention. For example, such a carrier can include any suitable excipient, buffer and/or delivery vehicle, such as a pharmaceutically acceptable carrier (discussed below), which is suitable for combining with the protein so that the protein can be used in vitro, ex vivo or in vivo according to the present invention. Compositions of the invention, including therapeutic compositions, are discussed in detail below.

Another embodiment of the invention relates to a processing deficient prelamin A peptide, wherein the processing deficient prelamin A peptide consists essentially of an amino acid sequence that differs from SEQ ID NO:4 (or a functional allelic variant thereof) by at least one substitution, deletion or insertion that results in a decrease in a prelamin A or prelamin A pre peptide biological activity. Such activity can include, but is not limited to: (a) prelamin A processing to release a prelamin A pre peptide (e.g., SEQ ID NO:2 or a biologically active homologue thereof); (b) prelamin A pre peptide signal transduction; (c) synchronization of intercellular signaling with changes in lamin A localization and nuclear lamina morphology that occur early in myoblast differentiation; (d) synchronization of transcriptional regulation of muscle-specific genes or cell cycle arrest that occurs concomitant with myoblast differentiation; (e) formation of normal nuclear lamina structure; and (f) induction of myoblast activation and differentiation. In one embodiment, the processing deficient prelamin A peptide consists essentially of an amino acid sequence that differs from SEQ ID NO:4 by a substitution of an amino acid residue in SEQ ID NO:4 selected from the group of: any amino acid that is rarely (e.g., less than 20% of the time) substituted across species, or Arg60, Leu85, Glu203, Arg89, Asn195, Arg377, Tyr646, G649, N650, P653, R654, P658, Q659, N660, Cys661, S662, I663 and/or M664. In another embodiment, the substitution is selected from the group of: Arg60Gly, Leu85Arg, Glu203Gly, Arg89Leu, Asn195Lys, and Arg377His. Also encompassed by the invention are isolated cells transfected with any of the processing deficient prelamin A proteins described herein.

Further embodiments of the present invention include nucleic acid molecules that encode any of the above-identified proteins, including a homologue or fragment thereof. In one embodiment, a nucleic acid molecule encoding pre peptide includes the nucleic acid sequence represented by SEQ ID NO:1, fragments thereof, or nucleic acid molecules encoding homologues of SEQ ID NO:2 as described herein. Nucleic acid molecules encoding prelamin A include the nucleic acid sequence represented by SEQ ID NO:3, fragments thereof, or nucleic acid molecules encoding homologues of SEQ ID NO:4 as described herein. In accordance with the present invention, an isolated polynucleotide, or an isolated nucleic acid molecule, is a nucleic acid molecule that has been removed from its natural milieu (i.e., that has been subject to human manipulation), its natural milieu being the genome or chromosome in which the nucleic acid molecule is found in nature. As such, "isolated" does not necessarily reflect the extent to which the nucleic acid molecule has been purified, but indicates that the molecule does not include an entire genome or an entire chromosome in which the nucleic acid molecule is found in nature. An isolated nucleic acid molecule can include a gene or a portion of a gene (e.g., the regulatory region or promoter). An isolated nucleic acid molecule that includes a gene is not a fragment of a chromosome that includes such gene, but rather includes the coding region and regulatory regions associated with the gene, but no additional genes naturally found on the same chromosome. An isolated nucleic acid molecule can also include a specified nucleic acid sequence flanked by (i.e., at the 5' and/or the 3' end of the sequence) additional nucleic acids that do not normally flank the specified nucleic acid sequence in nature (i.e., heterologous sequences). Isolated nucleic acid molecule can include DNA, RNA (e.g., mRNA), or derivatives of either DNA or RNA (e.g., cDNA). Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein. Preferably, an isolated nucleic acid molecule of the present invention is produced using recombinant DNA technology (e.g., polymerase chain reaction (PCR) amplification, cloning) or chemical synthesis.

Isolated nucleic acid molecules include natural nucleic acid molecules and homologues thereof, including, but not limited to modified (mutated) nucleic acid molecules in which, as compared to the natural or wild-type sequence, nucleotides have been inserted, deleted, substituted, and/or inverted in such a manner that such modifications (mutations) result in a nucleic acid sequence that encodes a desired homologue of a protein as described herein. A nucleic acid molecule homologue (e.g., a nucleic acid molecule encoding a protein homologue of the present invention) can be produced using a number of methods known to those skilled in the art (see, for example, Sambrook et al., *Molecular Cloning: A Laboratory Manual*, Cold Spring Harbor Labs Press, 1989). For example, wild-type nucleic acid molecules can be modified or nucleic acid molecules encoding modified proteins can be created using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, PCR amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids, for example, by screening for the function of the protein encoded by the nucleic acid and/or by hybridization with a wild-type gene.

The minimum size of a nucleic acid molecule of the present invention is a size sufficient to form a probe or oligonucleotide primer that is capable of forming a stable hybrid (e.g., under moderate, high or very high stringency conditions, discussed in detail above) with the complementary sequence of a nucleic acid molecule useful in the present invention, or of a size sufficient to encode an amino acid sequence for a protein of the invention. The nucleic acid molecule may also include regulatory regions, linker sequences, vector sequence or other sequence as necessary to provide a nucleic acid molecule according to the present invention. The minimal size of a nucleic acid molecule that is used as an oligonucleotide primer or as a probe is typically at least about 12 to about 15 nucleotides in length if the nucleic acid molecules are GC-rich and at least about 15 to about 18 bases in length if they are AT-rich. An oligonucleotide preferably ranges from about 5 to about 50 or about 500 nucleotides, including any size between about 5 and about 500 in whole integers (i.e., 5, 6, 7, 8, 9, . . . 34, 35, 36, . . . 200, 201, 202, . . . 500), and more preferably from about 10 to about 40 nucleotides, and most preferably from about 15 to about 40 nucleotides in length. There is no limit, other than a practical limit, on the maximal size of a nucleic acid molecule of the present invention, in that the nucleic acid molecule can include a sequence sufficient to encode the proteins of the invention and since the size of the nucleic acid molecule encoding such proteins can be dependent on nucleic acid composition and whether regulatory regions and/or other sequence are included (e.g., linkers, vector sequence, etc.).

Particularly preferred nucleic acid molecules according to the present invention include nucleic acid molecules comprising, consisting essentially of, or consisting of, nucleic acid sequences encoding any of the above-described amino acid sequences, including homologues thereof. In one embodiment, such a nucleic acid sequence includes an a nucleic acid sequence that is at least about 55% identical, or at least about 60% identical, or at least about 65% identical, or at least about 70% identical, or at least about 75% identical, or at least about 80% identical, or at least about 85% identical, or at least about 90% identical, or at least about 95% identical, or at least about 96% identical, or at least about 97% identical, or at least about 98% identical, or at least about 99% identical to SEQ ID NO:1 or SEQ ID NO:3, or to any of the other nucleic acid sequences described herein, over the full length of any of such sequences. Particularly preferred nucleic acid sequences include, but are not limited to, SEQ ID NO:1, SEQ ID NO:3, or fragments of such sequences, including a nucleic acid sequence encoding an isolated fragment of SEQ ID NO:4 with inter-nuclear transport domain biological activity or a biologically active homologue thereof. Additionally, fragments and other homologues of such sequences corresponding to the encoded amino acid sequences described above are also included. In one embodiment, the nucleic acid molecule does not encode a protein with biological activity, but is an oligonucleotide probe or primer (described previously herein).

One embodiment of the present invention relates to a recombinant nucleic acid molecule which comprises any of the isolated nucleic acid molecules described above which is operatively linked to at least one transcription control sequence. More particularly, according to the present invention, a recombinant nucleic acid molecule typically comprises a recombinant vector and an isolated nucleic acid molecule as described herein. According to the present invention, a recombinant vector is an engineered (i.e., artificially produced) nucleic acid molecule that is used as a tool for manipulating a nucleic acid sequence of choice and/or for introducing such a nucleic acid sequence into a host cell. The recombinant vector is therefore suitable for use in cloning, sequencing, and/or otherwise manipulating the nucleic acid sequence of choice, such as by expressing and/or delivering the nucleic acid sequence of choice into a host cell to form a recombinant cell. Such a vector typically contains heterologous nucleic acid sequences, that is, nucleic acid sequences that are not naturally found adjacent to nucleic acid sequence to be cloned or delivered, although the vector can also contain regulatory nucleic acid sequences (e.g., promoters, untranslated regions) which are naturally found adjacent to nucleic acid sequences of the present invention or which are useful for expression of the nucleic acid molecules of the present invention (discussed in detail below). The vector can be either RNA or DNA, either prokaryotic or eukaryotic, and typically is a plasmid. The vector can be maintained as an extrachromosomal element (e.g., a plasmid) or it can be integrated into the chromosome of a recombinant host cell. The entire vector can remain in place within a host cell, or under certain conditions, the plasmid DNA can be deleted, leaving behind the nucleic acid molecule of the present invention. An integrated nucleic acid molecule can be under chromosomal promoter control, under native or plasmid promoter control, or under a combination of several promoter controls. Single or multiple copies of the nucleic acid molecule can be integrated into the chromosome. A recombinant vector of the present invention can contain at least one selectable marker.

In one embodiment, a recombinant vector used in a recombinant nucleic acid molecule of the present invention is an expression vector. As used herein, the phrase "expression vector" is used to refer to a vector that is suitable for production of an encoded product (e.g., a protein of interest). In this embodiment, a nucleic acid sequence encoding the product to be produced (e.g., a prelamin A pre peptide) is inserted into the recombinant vector to produce a recombinant nucleic acid molecule. The nucleic acid sequence encoding the protein to be produced is inserted into the vector in a manner that operatively links the nucleic acid sequence to regulatory sequences in the vector which enable the transcription and translation of the nucleic acid sequence within the recombinant host cell.

Typically, a recombinant nucleic acid molecule includes at least one nucleic acid molecule of the present invention operatively linked to one or more expression control sequences. As used herein, the phrase "recombinant molecule" or "recombinant nucleic acid molecule" primarily refers to a nucleic acid molecule or nucleic acid sequence operatively linked to an expression control sequence, but can be used interchangeably with the phrase "nucleic acid molecule", when such nucleic acid molecule is a recombinant molecule as discussed herein. According to the present invention, the phrase "operatively linked" refers to linking a nucleic acid molecule to an expression control sequence (e.g., a transcription control sequence and/or a translation control sequence) in a manner such that the molecule is able to be expressed when transfected (i.e., transformed, transduced, transfected, conjugated or conduced) into a host cell. Transcription control sequences are sequences which control the initiation, elongation, or termination of transcription. Particularly important transcription control sequences are those which control transcription initiation, such as promoter, enhancer, operator and repressor sequences. Suitable transcription control sequences include any transcription control sequence that can function in a host cell or organism into which the recombinant nucleic acid molecule is to be introduced.

Preferred promoters to use in a recombinant nucleic acid molecule according to the invention include any promoter which can function in the cardiac or skeletal muscle tissue. Such promoters include, but are not limited to, a cardiac-specific promoter, a muscle-specific promoter, and a prelamin A promoter. In one aspect, the promoter is a myosin heavy chain promoter.

Recombinant nucleic acid molecules of the present invention can also contain additional expression control and other regulatory sequences, such as translation regulatory sequences, origins of replication, and other regulatory sequences that are compatible with the recombinant cell. In one embodiment, a recombinant molecule of the present invention, including those which are integrated into the host cell chromosome, also contains secretory signals (i.e., signal segment nucleic acid sequences) to enable an expressed protein to be secreted from the cell that produces the protein. Suitable signal segments include a signal segment that is naturally associated with the protein to be expressed or any heterologous signal segment capable of directing the secretion of the protein according to the present invention. In another embodiment, a recombinant molecule of the present invention comprises a leader sequence to enable an expressed protein to be delivered to and inserted into a membrane of a host cell. Suitable leader sequences include a leader sequence that is naturally associated with the protein, or any heterologous leader sequence capable of directing the delivery and insertion of the protein to a membrane of a cell.

According to the present invention, the term "transfection" is used to refer to any method by which an exogenous nucleic acid molecule (i.e., a recombinant nucleic acid molecule) can be inserted into a cell. The term "transformation" can be used interchangeably with the term "transfection" when such term is used to refer to the introduction of nucleic acid molecules into microbial cells. In microbial systems, the term "transformation" is used to describe an inherited change due to the acquisition of exogenous nucleic acids by the microorganism and is essentially synonymous with the term "transfection." However, in animal cells, transformation has acquired a second meaning which can refer to changes in the growth properties of cells in culture (described above) after they become cancerous, for example. Therefore, to avoid confusion, the term "transfection" is preferably used with regard to the introduction of exogenous nucleic acids into animal cells, and is used herein to generally encompass transfection of animal cells and transformation of microbial cells, to the extent that the terms pertain to the introduction of exogenous nucleic acids into a cell. Therefore, transfection techniques include, but are not limited to, transformation, particle bombardment, diffusion, active transport, bath sonication, electroporation, microinjection, lipofection, adsorption, infection and protoplast fusion.

One or more recombinant molecules of the present invention can be used to produce an encoded product (e.g., a prelamin A protein or a prelamin A pre peptide) of the present invention. In one embodiment, an encoded product is produced by expressing a nucleic acid molecule as described herein under conditions effective to produce the protein. A preferred method to produce an encoded protein is by transfecting a host cell with one or more recombinant molecules to form a recombinant cell. Suitable host cells to transfect include, but are not limited to, any bacterial, fungal (e.g., yeast), insect, plant or animal cell that can be transfected. Host cells can be either untransfected cells or cells that are already transfected with at least one other recombinant nucleic acid molecule.

In one embodiment, one or more protein(s) expressed by an isolated nucleic acid molecule of the present invention are produced by culturing a cell that expresses the protein (i.e., a recombinant cell or recombinant host cell) under conditions effective to produce the protein. In some instances, the protein may be recovered, and in others, the cell may be harvested in whole (e.g., for ex vivo administration), either of which can be used in a composition. In some instances, the protein may be expressed in a host cell in vivo (e.g., via gene therapy). A preferred cell to culture is any suitable host cell as described above. Effective in vitro or ex vivo culture conditions include, but are not limited to, effective media, bioreactor, temperature, pH and oxygen conditions that permit protein production and/or recombination. An effective medium refers to any medium in which a given host cell is typically cultured. Such medium typically comprises an aqueous medium having assimilable carbon, nitrogen and phosphate sources, and appropriate salts, minerals, metals and other nutrients, such as vitamins. Cells can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

Depending on the vector and host system used for production, resultant proteins of the present invention may either remain within the recombinant cell; be secreted into the culture medium; be secreted into a space between two cellular membranes; or be retained on the outer surface of a cell membrane. The phrase "recovering the protein" refers to collecting the whole culture medium containing the protein and need not imply additional steps of separation or purification. Proteins produced according to the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

Proteins produced according to the present invention are preferably retrieved in "substantially pure" form. As used herein, "substantially pure" refers to a purity that allows for the effective use of the protein in vitro, ex vivo or in vivo according to the present invention. For a protein to be useful in an in vitro, ex vivo or in vivo method according to the present invention, it is typically substantially free of contaminants, other proteins and/or chemicals that might interfere or that would interfere with its use in a method disclosed by the present invention, or that at least would be undesirable for inclusion with the protein (including homologues) when it is used in a method disclosed by the present invention. assays, preparation of therapeutic compositions, administration in a therapeutic composition, and all other methods disclosed herein. Preferably, a "substantially pure" protein, as referenced herein, is a protein that can be produced by any method (i.e., by direct purification from a natural source, recombinantly, or synthetically), and that has been purified from other protein components such that the protein comprises at least about 80% weight/weight of the total protein in a given composition (e.g., a prelamin A protein is about 80% of the total protein in a solution/composition/buffer), and more preferably, at least about 85%, and more preferably at least about 90%, and more preferably at least about 91%, and more preferably at least about 92%, and more preferably at least about 93%, and more preferably at least about 94%, and more preferably at least about 95%, and more preferably at least about 96%, and more preferably at least about 97%, and more preferably at least about 98%, and more preferably at least about 99%, weight/weight of the total protein in a given composition.

It will be appreciated by one skilled in the art that use of recombinant DNA technologies can improve control of expression of transfected nucleic acid molecules by manipulating, for example, the number of copies of the nucleic acid molecules within the host cell, the efficiency with which those nucleic acid molecules are transcribed, the efficiency with which the resultant transcripts are translated, and the efficiency of post-translational modifications. Additionally, the promoter sequence might be genetically engineered to improve the level of expression as compared to the native promoter. Recombinant techniques useful for controlling the expression of nucleic acid molecules include, but are not limited to, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules to correspond to the codon usage of the host cell, and deletion of sequences that destabilize transcripts.

In one embodiment of the invention, the recombinant nucleic acid molecule comprises a viral vector. A viral vector includes an isolated nucleic acid molecule of the present invention integrated into a viral genome or portion thereof, in which the nucleic acid molecule is packaged in a viral coat that allows entrance of DNA into a cell. A number of viral vectors can be used, including, but not limited to, those based on alphaviruses, poxviruses, adenoviruses, herpesviruses, lentiviruses, adeno-associated viruses and retroviruses.

The isolated nucleic acid molecules of the present invention, as well as the proteins produced by such molecules are all useful in various compositions of the invention. For example, in one embodiment, the isolated nucleic acid molecule (preferably as part of a recombinant nucleic acid molecule) is useful as for gene therapy, wherein administration of the nucleic acid molecule to an animal results in transfection of host cells of the animal with the molecule and expression of the protein(s) expressed by the molecule. As discussed above, nucleic acids encoding the prelamin A pre peptide or prelamin A are excellent candidates for gene therapy of cardiac and skeletal muscle disorders and degeneration. The present inventor's data shows that prelamin A is rapidly transferred between the multiple nuclei within a myocyte, and affects the morphology and organization of the transfected myocytes as well as that of adjacent untransfected myocytes. In another embodiment, the isolated nucleic acid molecule is used to produce the encoded protein(s) in vitro, which can then be used in a therapeutic composition. In yet another embodiment, the isolated nucleic acid molecule can be used to transfect cells ex vivo and then the cells are returned to the patient from which they were removed.

In one embodiment of the present invention, a therapeutic composition (comprising a nucleic acid or a protein) comprises a pharmaceutically acceptable carrier, which includes pharmaceutically acceptable excipients and/or delivery vehicles, for delivering the recombinant nucleic acid molecule or the proteins to a patient. As used herein, a pharmaceutically acceptable carrier refers to any substance or vehicle suitable for delivering a therapeutic composition useful in a therapeutic method of the present invention (described below) to a suitable in vivo or ex vivo site. When a nucleic acid molecule is in the composition, preferred pharmaceutically acceptable carriers are capable of maintaining the nucleic acid molecule in a form that, upon arrival of the nucleic acid molecule to a target cell or tissue, the nucleic acid molecule is capable of entering the cell and being expressed by the cell, whereby the expressed protein can perform one or more biological activities of the protein as described previously herein. When the composition comprises a protein, preferred pharmaceutically acceptable carriers are capable of maintaining the protein composition in a form that, upon arrival of the protein composition to a target cell or tissue, the proteins are capable of performing one or more biological functions of the protein as discussed above at the cell or tissue site.

A pharmaceutically acceptable carrier can include a pharmaceutically acceptable excipient. Suitable excipients of the present invention include excipients or formularies useful in a therapeutic composition. Examples of pharmaceutically acceptable excipients include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity.

Suitable pharmaceutically acceptable carriers for nucleic acids include, but are not limited to liposomes or other lipid-containing vehicles, viral vectors, ribozymes, gold particles, poly-L-lysine/DNA-molecular conjugates, and artificial chromosomes. Natural lipid-containing delivery vehicles include cells and cellular membranes. Artificial lipid-containing delivery vehicles include liposomes and micelles. A delivery vehicle can be modified to target to a particular site in a patient, thereby targeting and making use of a nucleic acid molecule at that site. Suitable modifications include manipulating the chemical formula of the lipid portion of the delivery vehicle and/or introducing into the vehicle a targeting agent (e.g., an antibody or peptide) capable of specifically targeting a delivery vehicle to a preferred site, for example, a preferred cell type. It is noted, however, that prelamin A and the prelamin A pre peptide are specific for cardiac and skeletal muscle tissue and therefore inherently will "target" the appropriate tissue and cell types. Therefore, the present invention is particularly advantageous in that while targeting moieties can be used, they are likely not necessary to administer these proteins or peptides (or nucleic acids encoding them) in vivo.

A liposome delivery vehicle comprises a lipid composition that is capable of delivering a nucleic acid molecule of the present invention, including naked DNA, plasmids and viral vectors, to a suitable cell and/or tissue in a patient. A liposome delivery vehicle comprises a lipid composition that is capable of fusing with the plasma membrane of the target cell to deliver the recombinant nucleic acid molecule into a cell. As discussed above, liposome delivery vehicles can be modified to target a particular site in a patient (i.e., a targeting liposome), thereby targeting and making use of a nucleic acid molecule of the present invention at that site. Suitable modifications include manipulating the chemical formula of the lipid portion of the delivery vehicle. Manipulating the chemical formula of the lipid portion of the delivery vehicle can elicit the extracellular or intracellular targeting of the delivery vehicle. For example, a chemical can be added to the lipid formula of a liposome that alters the charge of the lipid bilayer of the liposome so that the liposome fuses with particular cells having particular charge characteristics. Other targeting mechanisms include targeting a site by addition of exogenous targeting molecules (i.e., targeting agents) to a liposome (e.g., antibodies, soluble receptors or ligands). Targeting liposomes are described, for example, in Ho et al., 1986, *Biochemistry* 25: 5500-6; Ho et al., 1987a, *J Biol Chem* 262: 13979-84; Ho et al., 1987b, *J Biol Chem* 262: 13973-8; and U.S. Pat. No. 4,957,735 to Huang et al., each of which is incorporated herein by reference in its entirety).

Suitable pharmaceutically acceptable carriers for protein compositions include, but are not limited to, liquid injectables or solids which can be taken up in a suitable liquid as a suspension or solution for injection, liquids that can be aerosolized, capsules, tablets, or liposomes. In a non-liquid formulation, the excipient can comprise, for example, dextrose, human serum albumin, and/or preservatives to which sterile water or saline can be added prior to administration.

One type of pharmaceutically acceptable carrier includes a controlled release formulation that is capable of slowly releasing a composition of the present invention into an animal. As used herein, a controlled release formulation comprises recombinant nucleic acid molecule or protein composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, liposheres, and transdermal delivery systems.

Proteins, nucleic acids and compositions of the invention are useful in a variety of methods, including assays for the identification of compounds (including genes and proteins), as well as a variety of therapeutic methods. In one embodiment, the present invention includes methods which use nucleic acid sequences encoding prelamin A protein, prelamin A pre peptide, homologues and fragments thereof, and/or isolated cells that express such proteins, peptides and homologues (including recombinant cells and naturally occurring cells) as therapeutic reagents, screening tools and/or diagnostic tools.

Accordingly, embodiments of the present invention relate to: (1) a method to promote myoblast activation and regeneration of damaged, degenerated or atrophied cardiac and skeletal myocytes; (2) a method to stimulate cardiac or skeletal muscle growth in a mammal; and (3) a method to treat cardiac and skeletal muscle disorders. Each of these methods includes the step of administering to a patient that has a cardiac or skeletal muscle disorder, an agent selected from: (a) a prelamin A protein, prelamin A pre peptide, prelamin A internuclear transport fragment (e.g., fused to a therapeutic agent), or a fragment or homologue thereof as described previously herein; (b) a nucleic acid molecule encoding any of such proteins, peptides, fragments, or homologues as in (a); (c) a composition comprising any of such proteins, peptides, fragments, or nucleic acids of (a) or (b). The first method is useful for generally promoting myoblast activation and/or regeneration of damaged, degenerated or atrophied cardiac or skeletal myocytes, whether or not the patient is suffering from a disorder that involves these cells. The second method is useful to promote the growth of cardiac or skeletal muscle tissue, for example in the absence of any damage, disorder or atrophy, as may be desirable in athletes or astronauts. The third method is useful for treating cardiac and skeletal muscle disorders, including, but not limited to: dilated cardiomyopathy, Emery-Dreifuss muscular dystrophy, limb-girdle muscular dystrophy, partial lipodystrophy, axonal neuropathy, and mandibuloacral dysplasia. Another embodiment of the invention (discussed in detail below), comprises inhibiting prelamin A processing and particularly, prelamin A farnesylation, for the treatment of muscle cell cancers or metastatic cancers thereof.

Unique features of the prelamin A "pre" peptide described in detail herein are that it is a naturally occurring, small, biologically active signaling peptide. It would be easy to synthesize in a host cell, and particularly, in yeast, since yeast contain all of the necessary processing enzymes. In addition, the peptide would inherently be cardiac- and skeletal muscle-specific in its effects, and it would have no toxicity. The peptide would affect myocyte fusion in adults, as all human and mouse phenotypes are adult onset. Furthermore, the peptide exerts its effect on C2C12 and H9C2 cells, which share features with the satellite cells involved in adult skeletal muscle repair. By analogy to yeast a-type mating pheromone, the pre sequence of pre-lamin A is an early signaling molecule in myocyte differentiation, indicating that it would be a highly potent and efficacious treatment. Moreover, the use of prelamin A as a gene therapy shares these advantages and additionally, the present inventor has shown that this protein is rapidly transferred between nuclei within the myocyte, increasing its efficacy. Finally, the use of the inter-nuclear transport domain as a targeting moiety for other pharmaceuticals would increase their efficacy without introducing toxicity.

According to the present invention, the phrase "protected from a disease" refers to reducing the symptoms of the disease; reducing the occurrence of the disease, and/or reducing the severity of the disease. Protecting a patient can refer to the ability of a therapeutic composition of the present invention, when administered to a patient, to prevent a disease from occurring and/or to cure or to alleviate disease symptoms, signs or causes. As such, to protect a patient from a disease includes both preventing disease occurrence (prophylactic treatment) and treating a patient that has a disease or that is experiencing initial symptoms or later stage symptoms of a disease (therapeutic treatment). In particular, protecting a patient from a cardiac or skeletal muscle disease is accomplished according to the present invention by increasing: prelamin A processing, myoblast activation (including myoblast cell fusion and differentiation), prelamin A pre peptide signal transduction, and/or proper lamina formation. Protecting a patient from a muscle cell cancer or metastatic cancer thereof is accomplished by: reducing or preventing the prelamin A processing or at least the farnesylation of muscle cell tumors, and/or causing muscle cell tumor degeneration or cell death. The term, "disease" refers to any deviation from the normal health of a patient and includes a state when disease symptoms are present, as well as conditions in which a deviation (e.g., infection, gene mutation, genetic defect, etc.) has occurred, but symptoms are not yet manifested.

According to the present invention, an effective administration protocol (i.e., administering a therapeutic composition in an effective manner) comprises suitable dose parameters and modes of administration that result in an increase in any one or more of the biological activities associated with prelamin A or the prelamin A pre peptide as described above. Preferably, the patient is protected from the disease (e.g., by disease prevention or by alleviating one or more symptoms of ongoing disease). Effective dose parameters can be determined using methods standard in the art for a particular disease or condition. As mentioned above, in some circumstances, the patient may not have disease, but rather muscle atrophy, some muscle cell damage, or perhaps no disease or condition at all (e.g., in the case of an athlete). Effective dose parameters can be determined by those of skill in the art depending on the desired effect (e.g., stimulation of growth of healthy cardiac or skeletal muscle tissue, repair or regeneration of damaged tissue, etc.). Such parameters include, for example, determination of survival rates, side effects (i.e., toxicity), progression or regression of disease, or progress in tissue growth. In particular, the effectiveness of dose parameters of a therapeutic composition of the present invention when treating cancer can be determined by assessing response rates. Such response rates refer to the percentage of treated patients in a population of patients that respond with either partial or complete remission. Remission can be determined by, for example, measuring tumor size or microscopic examination for the presence of cancer cells in a tissue sample.

In accordance with the present invention, a suitable single dose size is a dose that results in regulation of the prelamin A processing pathway and associated biological activities and effects in a patient when administered one or more times over a suitable time period. Doses can vary depending upon the disease being treated. For example, in the treatment of cancer, a suitable single dose can be dependent upon whether the cancer being treated is a primary tumor or a metastatic form of cancer. One of skill in the art can readily determine appropriate single dose sizes for a given patient based on the size of a patient and the route of administration.

One of skill in the art can monitor the effectiveness of a treatment to repair damaged cardiac or skeletal muscle tissue by measuring, for example, cell morphology, physiological indicators of healthy cardiac and skeletal muscle tissue, physiological indicators of damaged cardiac and skeletal muscle tissue (e.g., creatine kinase), and include tests such as EKG, echocardiography, catheterization, heart biopsy, MRI, motion and strength tests, and muscle biopsies.

In one aspect of the invention, a suitable single dose of a therapeutic composition of the present invention is an amount that, when administered by any route of administration, increases at least one aspect of the prelamin A processing pathway or downstream effects (described previously), as compared to a patient which has not been administered with the therapeutic composition of the present invention (i.e., a control patient), as compared to the patient prior to administration of the composition, or as compared to a standard established for the particular disease, patient type and composition. In the case of cancer, a suitable single dose is an amount that decreases at least one symptom of the cancer, as compared to the same controls. Preferably, a suitable single dose of a therapeutic composition against a tumor is an amount that is sufficient to reduce, stop the growth of, and preferably eliminate, the tumor following administration of the composition into the tissue of the patient that has cancer.

It will be obvious to one of skill in the art that the number of doses administered to a patient is dependent upon the extent of the disease or condition or the desired result, as well as the response of an individual patient to the treatment. For example, a large tumor may require more doses than a smaller tumor. A patient with diseased cardiac or skeletal muscle tissue may require more doses than a healthy athlete who desires increased muscle cell growth. In some cases, however, one patient may require fewer doses than another patient having the same condition, if first patient responds more favorably to the therapeutic composition than the other patient. Thus, it is within the scope of the present invention that a suitable number of doses includes any number required to treat a given disease or to achieve a desired effect.

As discussed above, a therapeutic composition of the present invention is administered to a patient in a manner effective to deliver the composition to a cell, a tissue, and/or systemically to the patient, whereby regulation of the prelamin A processing pathway and downstream biological activities is achieved as a result of the administration of the composition. Suitable administration protocols include any in vivo or ex vivo administration protocol. The preferred routes of administration will be apparent to those of skill in the art, depending on the type of condition to be prevented or treated; whether the composition is nucleic acid based, protein based, or cell based; and/or the target cell/tissue. For proteins or nucleic acid molecules, preferred methods of in vivo administration include, but are not limited to, intravenous administration, intraperitoneal administration, intramuscular administration, intranodal administration, intracoronary administration, intraarterial administration (e.g., into a carotid artery), subcutaneous administration, transdermal delivery, intratracheal administration, subcutaneous administration, intraarticular administration, intraventricular administration, inhalation (e.g., aerosol), intracranial, intraspinal, intraocular, intranasal, oral, bronchial, rectal, topical, vaginal, urethral, pulmonary administration, impregnation of a catheter, and direct injection into a tissue.

Combinations of routes of delivery can be used and in some instances, may enhance the therapeutic effects of the composition.

Ex vivo administration refers to performing part of the regulatory step outside of the patient, such as administering a composition (nucleic acid or protein) of the present invention to a population of cells removed from a patient under conditions such that the composition contacts and/or enters the cell, and returning the cells to the patient. Ex vivo methods are particularly suitable when the target cell can easily be removed from and returned to the patient.

Many of the above-described routes of in vivo administration, including intravenous, intraperitoneal, intradermal, and intramuscular administrations can be performed using methods standard in the art. Aerosol (inhalation) delivery can also be performed using methods standard in the art (see, for example, Stribling et al., *Proc. Natl. Acad. Sci. USA* 189:11277-11281, 1992, which is incorporated herein by reference in its entirety). Oral delivery can be performed by complexing a therapeutic composition of the present invention to a carrier capable of withstanding degradation by digestive enzymes in the gut of an animal. Examples of such carriers, include plastic capsules or tablets, such as those known in the art.

One method of local administration is by direct injection. Direct injection techniques are particularly useful for administering a composition to a cell or tissue that is accessible by surgery, and particularly, on or near the surface of the body. Administration of a composition locally within the area of a target cell refers to injecting the composition centimeters and preferably, millimeters from the target cell or tissue.

Various methods of administration and delivery vehicles disclosed herein have been shown to be effective for delivery of a nucleic acid molecule to a target cell, whereby the nucleic acid molecule transfected the cell and was expressed. In many studies, successful delivery and expression of a heterologous gene was achieved in preferred cell types and/or using preferred delivery vehicles and routes of administration of the present invention. All of the publications discussed below and elsewhere herein with regard to gene delivery and delivery vehicles are incorporated herein by reference in their entirety.

For example, using liposome delivery, U.S. Pat. No. 5,705,15 1, issued Jan. 6, 1998, to Dow et al. demonstrated the successful in vivo intravenous delivery of a nucleic acid molecule encoding a superantigen and a nucleic acid molecule encoding a cytokine in a cationic liposome delivery vehicle, whereby the encoded proteins were expressed in tissues of the animal, and particularly in pulmonary tissues. In addition, Liu et al., *Nature Biotechnology* 15:167, 1997, demonstrated that intravenous delivery of cholesterol-containing cationic liposomes containing genes preferentially targets pulmonary tissues and effectively mediates transfer and expression of the genes in vivo.

Several publications by Dzau and collaborators demonstrate the successful in vivo delivery and expression of a gene into cells of the heart, including cardiac myocytes and fibroblasts and vascular smooth muscle cells using both naked DNA and Hemagglutinating virus of Japan-liposome delivery, administered by both incubation within the pericardium and infusion into a coronary artery (intracoronary delivery) (See, for example, Aoki et al., 1997, *J. Mol. Cell, Cardiol.* 29:949-959; Kaneda et al., 1997, *Ann N.Y. Acad. Sci.* 811:299-308; and von der Leyen et al., 1995, *Proc Natl Acad Sci USA* 92:1137-1141).

Delivery of numerous nucleic acid sequences has been accomplished by administration of viral vectors encoding the nucleic acid sequences. Using such vectors, successful delivery and expression has been achieved using ex vivo delivery (See, of many examples, retroviral vector; Blaese et al., 1995, *Science* 270:475-480; Bordignon et al., 1995, *Science* 270:470-475), nasal administration (CFTR-adenovirus-associated vector), intracoronary administration (adenoviral vector and Hemagglutinating virus of Japan, see above), intravenous administration (adeno-associated viral vector; Koeberl et al., 1997, *Proc Natl Acad Sci USA* 94:1426-1431). A publication by Maurice et al. (1999, *J. Clin. Invest.* 104:21-29) demonstrated that an adenoviral vector encoding a β2-adrenergic receptor, administered by intracoronary delivery, resulted in diffuse multichamber myocardial expression of the gene in vivo, and subsequent significant increases in hemodynamic function and other improved physiological parameters. Taken together, all of the above studies in gene therapy indicate that delivery and expression of a recombinant nucleic acid molecule according to the present invention is feasible.

Another method of delivery of recombinant molecules is in a non-targeting carrier (e.g., as "naked" DNA molecules, such as is taught, for example in Wolff et al., 1990, *Science* 247, 1465-1468). Such recombinant nucleic acid molecules are typically injected by direct or intramuscular administration. Recombinant nucleic acid molecules to be administered by naked DNA administration include an isolated nucleic acid molecule of the present invention, and preferably includes a recombinant molecule of the present invention that preferably is replication, or otherwise amplification, competent. A naked nucleic acid reagent of the present invention can comprise one or more nucleic acid molecules of the present invention including a bicistronic recombinant molecule. Naked nucleic acid delivery can include intramuscular, subcutaneous, intradermal, transdermal, intranasal and oral routes of administration, with direct injection into the target tissue (e.g., skeletal muscle or cardiac muscle) being most preferred. A preferred single dose of a naked nucleic acid vaccine ranges from about 1 nanogram (ng) to about 100 µg, depending on the route of administration and/or method of delivery, as can be determined by those skilled in the art. Suitable delivery methods include, for example, by injection, as drops, aerosolized and/or topically. In one embodiment, pure DNA constructs cover the surface of gold particles (1 to 3 µm in diameter) and are propelled into skin cells or muscle with a "gene gun."

In the method of the present invention, therapeutic compositions can be administered to any member of the Vertebrate class, Mammalia, including, without limitation, primates, rodents, livestock and domestic pets. Livestock include mammals to be consumed or that produce useful products (e.g., sheep for wool production). Preferred mammals to treat using a composition of the invention include humans, dogs, cats, mice, rats, sheep, cattle, horses and pigs, with humans being most preferred.

The discovery by the present inventor has also led the inventor to propose using this information to identify compounds that regulate myoblast activation and differentiation through a variety of different assays. Such methods are useful for identifying therapeutic reagents for treating cardiac and skeletal muscle disorders and diseases and/or for promoting myoblast activation and cardiac and skeletal muscle growth; for identifying proteins and cell lines containing specific mutations that will permit the elucidation of protein processing pathways relevant to normal heart and skeletal muscle development, disease development in heart and skeletal muscle, and cancer development and progression; and for identifying additional therapeutic targets for heart disease, muscular dystrophy, and cancer prevention. For example, it is an aspect of the invention to identify genes to screen for mutations leading to heart and skeletal muscle diseases, to use the gene products of genes identified as targets for therapeutic intervention in diseases of the cardiac and skeletal muscle.

One embodiment of the invention relates to a method to identify compounds that regulate myoblast activation and differentiation, comprising: (a) contacting a cell that expresses a prelamin A protein or a prelamin A pre peptide with a test compound under conditions suitable for modulation (regulation, increase or decrease, change, modification) of the activity of the prelamin A protein or prelamin A pre peptide by the test compound; and (b) detecting modulation of the activity of the prelamin A protein or prelamin A pre peptide by the test compound.

In this embodiment, the step of detecting can include, but is not limited to: detecting whether the test protein regulates prelamin A pre peptide transport in a cell; detecting whether the test protein regulates the processing of prelamin A in a cell; detecting whether the test protein regulates myoblast activation or differentiation; and/or detecting comprises detecting binding between the prelamin A protein or prelamin A pre peptide and the test compound. In one embodiment, the step of detecting comprises detecting an increase in myoblast activation and differentiation in the absence of correcting the prelamin A processing deficiency. Each of these steps of detecting can be compared to the various activity or parameter in the absence of the test compound. The steps of detecting are described in more detail below.

In one embodiment, the step of detecting comprises detecting binding between the prelamin A protein or prelamin A pre peptide and the test compound. Such an assay need not be a cell based assay (e.g., immunoprecipitation assay), although cells can be particularly useful for this type of assay (e.g. a yeast two hybrid system). Accordingly, one embodiment of the invention relates to a method to identify compounds that regulate myoblast activation and differentiation, comprising: (a) contacting a prelamin A protein or a prelamin A pre peptide with a test compound under conditions suitable for binding of the prelamin A protein or prelamin A pre peptide by the test compound; and (b) detecting binding of the prelamin A protein or prelamin A pre peptide by the test compound.

The test compound can include a variety of different types of compounds. In one aspect, the test compound is a protein encoded by a gene that is a candidate for regulation of prelamin A processing or prelamin A pre peptide transport in the cell. For example, suitable candidates include human homologues of a gene in the yeast a-type mating pheromone signaling pathway, or a gene encoding a candidate receptor for the prelamin A pre peptide. In another aspect, the test compound is a pharmaceutical compound. In one embodiment, the test compound is a putative pharmaceutical compound for use in the treatment of cardiac and skeletal muscle disorders, wherein an increase in the processing of prelamin A in the cell or an increase in myoblast activation and differentiation in the presence of the compound as compared to in the absence of the compound indicates that the compound is a therapeutic compound for use in the treatment of cardiac and skeletal muscle disorders. In yet another aspect, the test compound is a homologue of a prelamin A protein, a prelamin A pre peptide, or a prelamin A processing enzyme or downstream signal transduction molecule, or a gene encoding any of these test compounds.

Cells useful in the present assay include any cell expressing the prelamin A protein or prelamin A pre peptide, including, but not limited to, a differentiating cardiac myocyte or a differentiating skeletal myocyte, or a cell that has been transfected with a nucleic acid molecule encoding the prelamin A protein or prelamin A pre peptide. The prelamin A can be processing deficient (e.g., either a naturally occurring mutant or a synthetically created mutant), or the cell expressing the prelamin A protein or prelamin A pre peptide can be a prelamin A processing deficient cell (e.g., an isolate from a patient or a laboratory created cell). The cells can include cardiac myocytes or skeletal myocytes.

For example, one embodiment of the invention relates to a method to identify compounds that regulate myoblast activation and differentiation in a cell, comprising: (a) contacting an isolated prelamin A processing-deficient cell with a test compound for regulation of myoblast activation and differentiation; (b) contacting the isolated cell with test compound for regulation of myoblast activation and differentiation; and (c) detecting whether the test compound regulates an activity in the cell selected from the group consisting of: prelamin A processing, prelamin A pre peptide transport, and myoblast activation or differentiation, as compared to in the absence of the test compound. The present inventor has identified disease mutations that inhibit proper prelamin A processing in myocyte cell lines. This protein, and these transfected cell lines, will permit the elucidation of the enzymes and steps in the prelamin A processing pathway by complementation experiments. These cell lines will also serve as a reagent to test therapeutic agents to rectify the prelamin A processing deficiencies. Cell lines generated from a patient identified as carrying this lamin A/C mutation can be used for similar purposes.

Having generally described various methods of identification of the invention, more particular details of the assays that apply to one or more of the methods above will now be described. For example, it will be apparent that the methods described above are typically cell-based assays, but may include cell-free assays, such as when one wishes to assess binding of one protein to another.

In one aspect of these methods, the methods can include a step of contacting a cell that expresses a prelamin A protein or prelamin A pre peptide (including a prelamin A processing deficient cell), or contacting a prelamin A protein or a prelamin A pre peptide directly, with a putative regulatory compound (a test compound, including a gene, protein or candidate drug), followed by a step of detecting an effect on the cell or protein, preferably as compared to in the absence of the putative regulatory compound.

In these embodiments, a change in the regulation of some aspect of the prelamin A processing pathway, including downstream events that result from activation of this pathway, in the presence of the test compound as compared to in the absence of the test compound indicates that the test compound is an regulator of the prelamin A processing pathway. If the initial assay is not a cell-based assay (e.g., detects only binding of the test compound to a protein such as prelamin A), then the compound can be further tested, if desired, in a cell-based assay to determine whether the compound inhibits or enhances a biological activity within the prelamin A processing pathway. Such further steps will help detect the mode of action of the compound and whether it might be an agonist or antagonist of the prelamin A processing pathway.

As used herein, the term "putative" or "test" or "candidate" refers to compounds having an unknown or previously unappreciated regulatory activity in a particular process. As such, the term "identify" is intended to include all compounds, the usefulness of which as a regulatory compound according to the invention determined by a method of the present invention.

The methods of the present invention include contacting test compounds and cells, proteins or genes with one another to detect binding of one component to another or to detect the effect of the contact on expression and/or biological activity of one or more of the components. The step of contacting can be performed by any suitable method, depending on how the test compound and the cell, proteins, or genes are provided. For example, cells expressing prelamin A or a prelamin A pre peptide can be grown in liquid culture medium or grown on solid medium in which the liquid medium or the solid medium contains the compound to be tested. In addition, as described above, the liquid or solid medium contains components necessary for cell growth, such as assimilable carbon, nitrogen and micronutrients. Cell lysates can be combined with other cell lysates and/or the compound to be tested in any suitable medium. In another embodiment, proteins and/or cell lysates containing such proteins can be immobilized on a substrate such as: artificial membranes, organic supports, biopolymer supports and inorganic supports. The protein can be immobilized on the solid support by a variety of methods including adsorption, cross-linking (including covalent bonding), and entrapment. Adsorption can be through van del Waal's forces, hydrogen bonding, ionic bonding, or hydrophobic binding. Exemplary solid supports for adsorption immobilization include polymeric adsorbents and ion-exchange resins. Solid supports can be in any suitable form, including in a bead form, plate form, or well form. The putative regulatory compound can be contacted with the immobilized protein by any suitable method, such as by flowing a liquid containing the compound over the immobilized protein.

The present methods involve contacting cells or proteins with the compound being tested for a sufficient time to allow for interaction with the cell or protein, and regulation of the cell by the compound. The period of contact with the compound being tested can be varied depending on the result being measured, and can be determined by one of skill in the art. For example, for binding assays, a shorter time of contact with the compound being tested is typically suitable, than when activation is assessed. As used herein, the term "contact period" refers to the time period during which the proteins are in contact with the compound being tested and/or the time period during which the proteins or cells and the test compounds are in contact (or in a condition where contact is possible) with each other. The term "incubation period" refers to the entire time during which, for example, cells are allowed to grow prior to evaluation, and can be inclusive of the contact period. Thus, the incubation period includes all of the contact period and may include a further time period during which the compound being tested is not present but during which growth is continuing (in the case of a cell based assay) prior to scoring. It will be recognized that shorter incubation times are preferable because compounds can be more rapidly screened.

The conditions under which a cell or cell lysate is contacted with a putative regulatory compound, such as by mixing, are any suitable culture or assay conditions and includes an effective medium in which the cell can be cultured or in which the cell lysate can be evaluated in the presence and absence of a putative regulatory compound. Similarly, the conditions under which proteins (e.g., prelamin A or pre peptide) are contacted with a putative regulatory compound are any suitable assay conditions, such as by immobilization of the protein or peptide on a substrate in conditions under which the protein or peptide can contact the putative regulatory compound.

Cells of the present invention can be cultured in a variety of containers including, but not limited to, tissue culture flasks, test tubes, microtiter dishes, and petri plates. Culturing is carried out at a temperature, pH and carbon dioxide content appropriate for the cell. Such culturing conditions are also within the skill in the art. Acceptable protocols to contact a cell with a putative regulatory compound in an effective manner include the number of cells per container contacted, the concentration of putative regulatory compound(s) administered to a cell, the incubation time of the putative regulatory compound with the cell, and the concentration of compound administered to a cell. Determination of such protocols can be accomplished by those skilled in the art based on variables such as the size of the container, the volume of liquid in the container, the type of cell being tested and the chemical composition of the putative regulatory compound (i.e., size, charge etc.) being tested. A preferred amount of putative regulatory compound(s) comprises between about 1 nM to about 10 mM of putative regulatory compound(s) per well of a 96-well plate.

Suitable cells for use with the present invention include any cell that endogenously expresses prelamin A or prelamin A pre peptide (wild-type or processing-deficient), or which has been transfected with and expresses a recombinant prelamin A or prelamin A pre peptide as disclosed herein. Such cells can include cells with normal prelamin A processing and prelamin A processing-deficient cells (which may contain normal prelamin A). In one embodiment, host cells genetically engineered to express a prelamin A or pre peptide can be used as an endpoint in the assay; e.g., as measured by a chemical, physiological, biological, or phenotypic change, induction of a host cell gene or a reporter gene, change in cAMP levels, adenylyl cyclase activity, host cell G protein activity, host cell kinase activity, proliferation, differentiation, etc. Cells for use with the present invention include mammalian, invertebrate, plant, insect, fungal, yeast and bacterial cells. Preferred cells include mammalian cells. Other preferred cells include cardiac or skeletal muscle myocytes and preferably, differentiating cardiac or skeletal muscle myocytes. Prelamin A processing-deficient cells useful in the present invention have been isolated by the present inventor are described in the Examples section.

As discussed above, the step of detecting whether a test compound binds to prelamin A or pre peptide (or another protein or gene in a cell) or regulates a parameter of prelamin A processing and/or its downstream biological effects, can be performed by any suitable method. Such methods include, but are not limited to: measurement of protein-protein binding or interaction, measurement of transcription of prelamin A, measurement of translation of prelamin A, measurement of posttranslational modification of prelamin A, measurement of proper processing of the pre peptide, measurement of pre peptide signal transduction, measurement of lamin A incorporation into the nuclear lamina structure, measurement of transcriptional regulation of muscle-specific genes and/or cell cycle arrest, measurement of nuclear lamina morphology, measurement of pre peptide transport, measurement of lamin A localization, measurement of myocyte cell fusion, and/or measurement of myoblast activation and differentiation. Techniques for performing such measurements are known in the art, and include a variety of binding assays, western blotting, immunocytochemistry, flow cytometry, other immunological based assays, phosphorylation assays, kinase assays, immunofluorescence microscopy, RNA assays, immunoprecipitation, cytokine assays, evaluation of cell morphology, in situ hybridization, and other biological assays. Binding assays include BIAcore machine assays, immunoassays such as enzyme linked immunoabsorbent assays (ELISA) and radioimmunoassays (RIA), or determination of binding by monitoring the change in the spectroscopic or optical properties of the proteins through fluorescence, UV absorption, circular dichroism, or nuclear magnetic resonance (NMR). Binding and/or interaction between two proteins can be determined using yeast two hybrid systems. Methods for evaluating prelamin A processing and its biological effects are described in the Examples section.

As discussed above, in vitro cell based assays may be designed to screen for compounds that regulate prelamin A processing and associated biological events at either the transcriptional or translational level. For example, one embodiment of the invention relates to a method to identify a genes or gene products that regulate the processing of prelamin A or activities downstream of the prelamin A processing and pre peptide signal transduction. In one aspect, a nucleic acid sequence encoding a reporter molecule can be linked to a regulatory element of prelamin A or an associated protein and used in appropriate intact cells, cell extracts or lysates to identify compounds that modulate prelamin A gene expression or expression of a gene involved in prelamin A processing or pre peptide signal transduction. Appropriate cells or cell extracts can be prepared, if desired, from any cell type that normally expresses a gene encoding prelamin A, thereby ensuring that the cell extracts contain the transcription factors required for in vitro or in vivo transcription. The screen can be used to identify compounds that modulate the expression of the reporter construct. In such screens, the level of reporter gene expression is determined in the presence of the test compound and compared to the level of expression in the absence of the test compound.

The method can also include the step of detecting the expression of at least one, and preferably more than one, of the downstream genes that are regulated by prelamin A processing and the release of the pre peptide, or of the genes that are involved in the processing of prelamin A. As used herein, the term "expression", when used in connection with detecting the expression of a downstream gene of the present invention, can refer to detecting transcription of the gene and/or to detecting translation of the gene. To detect expression of a gene refers to the act of actively determining whether a gene is expressed or not. This can include determining whether the gene expression is upregulated as compared to a control, downregulated as compared to a control, or unchanged as compared to a control. Therefore, the step of detecting expression does not require that expression of the gene actually is upregulated or downregulated, but rather, can also include detecting that the expression of the gene has not changed (i.e., detecting no expression of the gene or no change in expression of the gene). Expression of transcripts and/or proteins is measured by any of a variety of known methods in the art. For RNA expression, methods include but are not limited to: extraction of cellular mRNA and northern blotting using labeled probes that hybridize to transcripts encoding all or part of one or more of the genes of this invention; amplification of mRNA expressed from one or more genes using gene-specific primers, if available and reverse transcriptase—polymerase chain reaction, followed by quantitative detection of the product by any of a variety of means; extraction of total RNA from the cells, which is then labeled and used to probe cDNAs or oligonucleotides encoding all or part of the genes of this invention, arrayed on any of a variety of surfaces. The term "quantifying" or "quantitating" when used in the context of quantifying transcription levels of a gene can refer to absolute or to relative quantification. Absolute quantification may be accomplished by inclusion of known concentration(s) of one or more target nucleic acids and referencing the hybridization intensity of unknowns with the known target nucleic acids (e.g. through generation of a standard curve). Alternatively, relative quantification can be accomplished by comparison of hybridization signals between two or more genes, or between two or more treatments to quantify the changes in hybridization intensity and, by implication, transcription level.

Another embodiment of the methods described above includes identifying whether a candidate gene is a gene that encodes a product that is involved in either prelamin A processing, or downstream activities resulting from prelamin A processing and the release of the pre peptide. Such methods are typically performed by protein-protein interaction assays to identify gene products that interact with a given protein (e.g., prelamin A or pre peptide), or by complementation assays using cell lines expressing various proteins in the pathway.

In one embodiment, the invention includes a method to identify human genes that regulate myoblast activation and differentiation, comprising: (a) contacting a probe with a source of human DNA from heart or skeletal muscle tissue under low stringency conditions, wherein the probe is a nucleic acid sequence from a gene in the yeast a-type mating pheromone signal transduction pathway; (b) identifying genes in the source of human DNA that hybridize to the probe; and (c) detecting whether genes that hybridize to the probe encode a protein that corrects a prelamin A processing deficiency or that increases myoblast activation and differentiation. For example, the gene in the yeast a-type mating pheromone signal transduction pathway can include a gene that is associated with a biological function selected from: transcriptional activation of pheromone responsive genes, post-transcriptional blockade of the cell cycle, and cell fusion pathway activation. As discussed above, the only protein known to be post-translationally processed in the same manner as prelamin A is the yeast a-type mating pheromone. Yeast a-factor (Mat a) peptide activates a receptor-coupled G protein which, in turn activates a mitogen-activated protein (MAP) kinase. This splits the signal into three branches: transcriptional activation of pheromone responsive genes, post-transcriptional blockade of the cell cycle, and cell fusion pathway activation. Therefore, human homologues of genes in the yeast a-type mating pheromone pathway are good candidates for other genes relevant to the prelamin A processing and pre peptide signal transduction, including candidates for genes that contain mutations that cause heart and skeletal muscle diseases. These genes and their protein products are putative targets for therapies to prevent cardiac and skeletal muscle diseases.

Methods of creating probes suitable for use in a homologue screen are known in the art and include the preparation of degenerate primers. Methods for identifying genes using hybridization are well known in the art. It is generally recognized that nucleic acids are denatured by increasing the temperature or decreasing the salt concentration of the buffer containing the nucleic acids. Under low stringency conditions (e.g., low temperature and/or high salt) hybrid duplexes (e.g., DNA:DNA, RNA:RNA, or RNA:DNA) will form even where the annealed sequences are not perfectly complementary. Thus specificity of hybridization is reduced at lower stringency. Conversely, at higher stringency (e.g., higher temperature or lower salt) successful hybridization requires fewer mismatches. Hybridization conditions are described in detail above.

Yet another embodiment of the invention relates to a method to identify an inhibitor of prelamin A farnesylation, comprising the steps of: (a) contacting an isolated cell that expresses prelamin A with a putative regulator of prelamin A farnesylation; and (b) detecting whether farnesylation of prelamin A is inhibited by the putative regulator. The farnesylation and subsequent processing of pre-lamin A is essential for its proper function in cardiac and skeletal myocyte formation. Activation of the Ras oncogene is responsible for greater than 70% of colorectal cancer cases. Farnesylation of Ras is the initial step in Ras activation. Currently, farnesylation inhibitors are being used in clinical trials to prevent Ras activation and cancer progression. Therefore, identification of the enzymatic steps in the prelamin A farnesylation pathway will identify putative targets for additional therapies to prevent Ras activation and colorectal cancer. In addition, the present inventor has found that inhibition of farnesylation using known inhibitors in differentiating muscle cells causes muscle cell degeneration and muscle cell death. Based on the present inventor's discovery, one can now see that inhibition of proper prelamin A processing is most likely the cause of this result. Therefore, the present inventor proposes using inhibitors of prelamin A processing, and particularly, farnesylation inhibitors, to inhibit or treat muscle cell cancers via inhibition of the prelamin A processing pathway.

In the method of identification of farnesylation inhibitors, the cell can be any suitable cell expressing prelamin A as discussed previously herein. In one embodiment, the cell is selected from the group consisting of a differentiating cardiac myocyte and a differentiating skeletal myocyte. In another embodiment, the cell has been transfected with a nucleic acid molecule encoding prelamin A. The step of detecting includes detecting whether prelamin A farnesylation is reduced as compared to in the absence of the putative inhibitor compound. In additional steps, one can detect whether inhibitors of prelamin A farnesylation detected in step (b) regulate prelamin A processing in the cell, wherein detection of reduced prelamin A processing in the presence of the regulator indicates that the regulator may be useful for treatment of muscle cell cancers. Alternatively, one can detect whether inhibitors of prelamin A farnesylation detected in step (b) cause myoblast dissociation or myoblast cell death, wherein detection of increased myoblast dissociation or myoblast cell death in the presence of the regulator indicates that the regulator may be useful for treatment of muscle cell cancers. Methods of contacting and detecting useful in this aspect of the invention have been described generally above for other cell-based assays and are additionally known in the art. Methods of detecting farnesylation of a protein are described, for example, in: *Proc Natl. Acad. Sci.* 89:3000-3004 (1992); or *Proc. Natl. Acad. Sci.* 97:11626-11631 (2000), incorporated herein by reference in their entireties. Methods of detecting myoblast dissociation or cell death are also well known in the art.

Accordingly, another embodiment of the invention is a method to treat a muscle cell cancer, comprising administering to a patient with a muscle cell cancer or metastatic cancer thereof a compound that inhibits prelamin A processing and myoblast differentiation. The compound can include any known or as yet unknown compound that will inhibit prelamin A processing and particularly, farnesylation of prelamin A. One particularly preferred compound can include a statin that is toxic to myocytes. Methods to identify such compounds have been described previously herein. Muscle cell cancers to treat using this method include, but are not limited to: myosarcoma, myeloma, myoma, rhabdomyosarcoma, and malignant uterine fibroids.

Another embodiment of the present invention relates to a method to diagnose a disorder associated with prelamin A processing defects, or to screen for patients that carry mutations that may cause cardiac or skeletal muscle disorders. The method includes the steps of detecting expression or biological activity of prelamin A or the prelamin A pre peptide in a tissue of a patient suspected of having a disorder, and comparing the expression or biological activity to a control, wherein a difference in the expression or biological activity of prelamin A or the pre peptide (including a gene encoding such proteins) in a tissue of the patient as compared to the control indicates a positive diagnosis of a disorder associated with improper prelamin A processing. Once additional enzymes and proteins in the processing and signal transduction pathway have been elucidated, these proteins and genes encoding them can also be used to diagnose or screen patients for a cardiac or skeletal muscle disorder. The terms "diagnose", "diagnosis", "diagnosing" and variants thereof refer to the identification of a disease or condition on the basis of its signs and symptoms. As used herein, a "positive diagnosis" indicates that the disease or condition, or a potential for developing the disease or condition, has been identified. In contrast, a "negative diagnosis" indicates that the disease or condition, or a potential for developing the disease or condition, has not been identified.

According to the present invention, the term "cell sample" can be used generally to refer to a sample of any type which contains cells to be evaluated by the present method, including but not limited to, a sample of isolated cells, a tissue sample and/or a bodily fluid sample. According to the present invention, a sample of isolated cells is a specimen of cells, typically in suspension or separated from connective tissue which may have connected the cells within a tissue in vivo, which have been collected from an organ, tissue or fluid by any suitable method which results in the collection of a suitable number of cells for evaluation by the method of the present invention. The cells in the cell sample are not necessarily of the same type, although purification methods can be used to enrich for the type of cells which are preferably evaluated. Cells can be obtained, for example, by scraping of a tissue, processing of a tissue sample to release individual cells, or isolation from a bodily fluid. A tissue sample, although similar to a sample of isolated cells, is defined herein as a section of an organ or tissue of the body which typically includes several cell types and/or cytoskeletal structure which holds the cells together. One of skill in the art will appreciate that the term "tissue sample" may be used, in some instances, interchangeably with a "cell sample", although it is preferably used to designate a more complex structure than a cell sample. A tissue sample can be obtained by a biopsy, for example, including by cutting, slicing, or a punch. A bodily fluid sample, like the tissue sample, contains the cells to be evaluated, and is a fluid obtained by any method suitable for the particular bodily fluid to be sampled. Nucleic acids can be prepared from any of these samples for screening.

Methods suitable for detecting transcription or translation have been described elsewhere herein and include any suitable method for detecting and/or measuring mRNA levels or protein levels from a cell, cell extract or tissue.

Methods for detecting transcription include, but are not limited to: polymerase chain reaction (PCR), reverse transcriptase PCR (RT-PCR), in situ hybridization, Northern blot, sequence analysis, and detection of a reporter gene. Such methods for detection of transcription levels are well known in the art, and many of such methods are described in Sambrook et al., *Molecular Cloning: A Laboratory Manual*, Cold Spring Harbor Labs Press, 1989 and/or in Glick et al., *Molecular Biotechnology: Principles and Applications of Recombinant DNA*, ASM Press, 1998; Sambrook et al., ibid., and Glick et al., ibid. are incorporated by reference herein in their entireties. Methods suitable for the detection of protein include, but are not limited to, immunoblot (e.g., Western blot), enzyme-linked immunosorbant assay (ELISA), radioimmunoassay (RIA), immunoprecipitation, immunohistochemistry and immunofluorescence. Such methods are well known in the art.

Typically, in a diagnostic or screening assay, a test level of expression of a protein or nucleic acid is compared to a baseline level, or control. According to the present invention, a "baseline level" is a control level, and in some embodiments, a normal level of protein or gene expression or activity against which a test level of protein or gene expression or biological activity (i.e., in the patient sample) can be compared. The method for establishing a baseline level of protein or gene expression or activity is selected based on the sample type, the tissue or organ from which the sample is obtained, the status of the patient to be evaluated, and the focus or goal of the assay (e.g., diagnosis, staging, monitoring). Preferably, the method is the same method that will be used to evaluate the sample in the patient. Baseline levels can be established using an autologous control sample obtained from the patient, an autologous level in a previous sample from the same patient, or using control samples that were obtained from a population of matched individuals.

The following examples are provided for the purpose of illustration and are not intended to limit the scope of the present invention.

EXAMPLES

Materials and Methods.

Plasmids. The wild type prelamin A cDNA, a gift from M. Sinensky (Eastern Tennessee State University), was subcloned from pMMLA into pAlter-1 (Promega). Oligonucleotide primers were designed containing six different lamin A/C sequence mutations that cause DCM; C178G (Arg60Gly), T254G (Leu85Arg), C585G (Asn195Lys), A608G (Glu203Gly), G266T (Arg89Leu), and G1130A (Arg377His). Each primer contains 10-11 bp of flanking sequence homology on either side of the mutation. Site directed mutagenesis was performed on the wild type prelamin A cDNA/pAlter-1 construct using Altered Sites (Promega). DNA was isolated from individual transformants and sequenced to identify clones containing the induced mutations.

The wild type and six mutant prelamin A/pAlter-1 plasmid DNAs were used as templates in PCR reactions with primers designed to permit sub-cloning of the prelamin A cDNA PCR products in-frame with the N-terminal GFP coding sequence of pEGFP-C1 (Clonetech). The prelamin A cDNA inserts were sequenced in their entirety to confirm the presence of the desired mutation and the absence of any spurious Taq polymerase-induced mutations.

Cells and Transfections. C2C12 and H9C2 cells were incubated for 24 h in DMEM containing 10% (vol/vol) fetal bovine serum. Effectene (Qiagen) was used to transfect plasmid DNA into cells following the manufacturers instructions. Non-differentiating cells were allowed to continue growing for an additional 24 h before being processed for microscopy, or until near confluent (2 to 3 days) for protein isolation. For differentiation, H9C2 and C2C12 cells were allowed to continue growing 36 hours after transfection prior to incubation in DMEM containing 2% (vol/vol) horse serum. In the case of H9C2 cells, differentiation media also contained 10 nM retinoic acid. C2C12 cells were differentiated for 48 hours or 8 days, and H9C2 cells were differentiated 7 days prior to processing for microscopy.

Indirect immunofluorescence (IF). All slides were fixed by treating with cold 70% methanol/30% acetone solution for 10 min. Immunostaining was performed by treating fixed cells with anti-lamin A/C mouse monoclonal antibody (NCL-LAM-A/C)(1:50) (Novocastra Laboratories), or anti-desmin rabbit polyclonal antibody (1:50) (Sigma). The secondary antibody used with the anti-lamin A/C antibody was Texas red-conjugated horse anti-mouse (1:300) (Vector Laboratories), and the secondary antibody used with the anti-desmin antibody was Texas red-conjugated goat anti-rabbit (1:300) (Vector Laboratories). Cover slips were mounted with Vectashield containing DAPI (Vector Laboratories).

Western blots. Non-differentiated C2C12 cells were lysed in cell buffer (1% Triton X-100, 20 mM Tris-Cl, 7.5, 10 mM NaCl, 5 mM $MgCl_2$) containing 46 μg/ml Leupeptin (Sigma), 10 μg/ml Aprotinin (Sigma), and 250 μg/ml AEBSF (Sigma) for 10 min on ice. Total protein concentration was determined using BioRad Protein Assay reagent. One volume of 2× Laemli loading buffer was added and the samples were boiled for 2 min. Proteins were separated by polyacrylamide gel electrophoresis and transferred to Immobilon-P (Millipore). Western blots were probed with an anti-GFP rabbit polyclonal antibody (SC-8334) (1:1000) (Santa Cruz Biotechnology) and HRP-conjugated goat anti-rabbit secondary antibody (1:5000) (BioRad), or an anti-prelamin A goat polyclonal antibody (SC-6214) (1:100) (Santa Cruz Biotechnology) and HRP-conjugated mouse anti-goat secondary antibody (1:500) (Santa Cruz Biotechnology). Secondary antibody detection was performed using Super signal HRP (Pierce).

Example 1

The following example demonstrates that mutations that cause dilated cardiomyopathy result in aberrant lamin A localization and lamina formation.

Indirect IF microscopic studies of peptide-tagged lamin A proteins containing disease-causing mutations have demonstrated that these mutations can affect the structure of the nuclear lamina. However, changes in the structure of the nuclear lamina can mask antigenic sites and inhibit antibody access. Consequently, it is unclear if the changes in lamina structure revealed by indirect IF reflect the true localization of, and structures formed by, the mutant lamin A proteins, or alterations in the interactions between the antibodies used in these experiments and the mutant lamin A proteins. In order to directly visualize the effects of disease-causing mutations on lamina formation and lamin A localization, the present inventor created a prelamin A fusion protein expression construct in which the coding sequence for GFP was fused to the N-terminal end of the prelamin A cDNA. An N-terminal GFP-prelamin A fusion protein has been shown to be processed and function normally in mammalian cells.

Six different single nucleotide substitutions that cause DCM were independently introduced into the GFP prelamin A cDNA by site-directed mutagenesis. These mutations result in the amino acid substitutions (relative to SEQ ID NO:4) Arg60Gly, Leu85Arg, Asn195Lys, Glu203Gly, Arg89Leu and Arg377His. The wild type and mutant expression constructs were transfected into mouse C2C12 skeletal myoblasts. Expression of the mutant lamin proteins in C2C12 cells, which express endogenous wild type lamins A and C, approximates the heterozygous state of lamin expression in the tissues of patients affected by these autosomal dominant disease mutations. In order to compare the results obtained by direct fluorescence microscopy of the GFP signal with those produced by indirect IF microscopy, the cells were fixed and stained with a human-specific anti-lamin A/C antibody. As expected, the wild type prelamin A fusion protein incorporated into the nuclear lamina as evidenced by the more intense signal seen around the circumference of the nucleus (data not shown). In addition, a number of intranuclear lamin A filaments were observed as previously described.

The nuclear lamina formed in cells expressing the fusion proteins containing the mutations Arg60Gly, Leu85Arg and Arg377His (data not shown) are indistinguishable from those formed by the wild type construct. However, extra-nuclear GFP fusion protein aggregates are seen in the transfectants expressing the Arg60Gly and Leu85Arg mutations. While the fusion protein containing the Glu203Gly mutation incorporates efficiently into the nuclear lamina (data not shown), nuclei of transfectants expressing this mutant protein typically contain large areas of diffuse GFP signal that are devoid of the fine filamentous structures seen in the wild type control. These transfectants also contain cytoplasmic GFP fusion protein aggregates. The expression of fusion proteins containing the Asn195Lys (data not shown) and Arg89Leu (data not shown) mutations results in the formation of intranuclear lamin aggregates. All aggregates are located at the nuclear periphery as determined by three-dimensional volume projections of the digitally deconvolved images (data not shown). Increasing the gain of the GFP channel revealed nucleoplasmic GFP signal in the Arg89Leu transfectants, but not in the Asn195Lys transfectants (data not shown).

Indirect IF analysis of transfectants expressing the wild type prelamin A construct accurately represents the localization of the GFP fusion protein, and its incorporation into the nuclear lamina and intranuclear filaments. However, artifacts in the form of intranuclear antibody aggregates that do not co-localize with the GFP signal are observed in transfectants containing the wild type, and each of the mutant fusion protein constructs (data not shown). Indirect IF analysis of transfectants expressing the Arg60Gly, Leu85Arg and Arg377His protein constructs demonstrates that these mutations are affecting the lamina structure such that the antibody under represents the incorporation of the GFP fusion proteins into the lamina, and over represents the nucleoplasmic localization of these proteins. Indirect IF analysis of transfectants expressing fusion proteins containing the Asn195Lys, Glu203Gly and Arg89Leu mutations accurately depicts the localization of the mutant fusion proteins. However, antibody access to the interior of the intranuclear aggregates in cells expressing the Asn195Lys and Arg89Leu mutations is prevented, resulting in the false representation of these mutant proteins forming hollow, ring-like structures.

Example 2

The following example demonstrates that lamin A/C mutations affect different steps in prelamin A processing.

Prelamin A is processed in a sequential series of post-translation modifications shared by the *S. cerevisiae* a-type mating pheromone. To determine if the mutations associated with DCM affect prelamin A processing, equal amounts of total protein extracts from C2C12 myoblasts transfected with the wild type and mutant fusion protein constructs were analyzed by Western blot analysis with an anti-GFP antibody. Referring to FIG. 1, total protein was isolated from C2C12 cells that were untransfected (lane 1), or transfected with the wild type prelamin A fusion protein construct (lane 2), and with the prelamin A constructs containing the Arg60Gly (lane 3), Leu85Arg (lane 4), Asn195Lys (lane 5), Glu203Gly (lane 6), Arg89Leu (lane 7), and Arg377His (lane 8) mutations. Proteins were resolved by 10% SDS/PAGE, transferred to membranes, and probed with an anti-GFP antibody (A) or prelamin A-specific antibody (B). The migration of MW standards are indicated in kDa at left.

A protein band of the size expected for lamin A (74 kDa) fused to GFP (27 kDa) was detected in all transfectants (FIG. 1A, lanes 2-8), and was absent from the untransfected control (FIG. 1A, lane 1). The intensity of this band varies between samples, reflecting that the proteins were isolated from transient transfections that resulted in different transfection efficiencies.

The GFP fusion protein containing the Arg89Leu mutation (FIG. 1A, lane 7) has reduced mobility as compared with the other protein constructs. This protein also migrates slower on Western blots of total protein isolated from H9C2 rat cardiac myoblast transfectants probed with the anti-GFP antibody, and from HeLa cell transfectants probed with an anti-lamin A/C antibody (data not shown). In order to confirm the Arg89Leu mutation is affecting prelamin A processing, Western blot analysis of the C2C12 protein extracts was performed using an antibody which specifically recognizes the C-terminal "pre" peptide of prelamin A. Prelamin A was detected in the protein extracts from transfectants expressing the Arg89Leu mutation (FIG. 1B, lane 7), and in extracts from cells expressing the Glu203Gly and Arg377His mutations as well (FIG. 1B, lanes 7 and 8, respectively). Furthermore, the prelamin A protein containing the Glu203Gly mutation has a greater mobility than those containing the Arg89Leu and Arg377His mutations, demonstrating that the Glu203Gly mutation affects a different prelamin A processing step.

Example 3

The following example demonstrates that lamin A/C mutations affect myoblast differentiation.

The observations that DCM resulting from lamin A/C gene mutations is not a congenic disorder, and that lamin A/C knockout mice fail to show skeletal and cardiac pathologies until 3-4 weeks post natal, indicate that lamin A/C disease mutations affect tissue growth and repair, not organogenesis. In adult skeletal muscle, mononucleated stem cells referred to as "satellite cells" are responsible for the regeneration of muscle fibers in response to injury. To test the hypothesis that lamin A/C gene mutations responsible for DCM affect satellite cell function, mouse C2C12 cells transfected with the wild type and mutant prelamin A fusion protein constructs were induced to differentiate, and examined for defects in myocyte morphology and intercellular organization after two days of growth in differentiation media. Direct fluorescence microscopy was used to identify myocytes expressing the GFP fusion protein constructs. Indirect IF microscopy was performed using an anti-desmin antibody, as desmin is an early marker of myocyte differentiation expressed throughout the cytoplasm of the myotube.

Analysis of myocytes expressing the fusion protein constructs reveals that lamin A is not restricted to nuclear domains, and is present in either all or none of the C2C12 myotube nuclei (data not shown). The transfer of lamin A between nuclei occurs at an early stage of myoblast fusion, as it was not possible to detect any myocytes containing 2 or 3 nuclei in which only one or two of the nuclei contained GFP-lamin A. Myocyte morphology and intercellular organization are not affected by expression of the wild type construct, as the nuclei within the myotube are arranged in a normal, linear fashion (data not shown), and adjacent myotubes are organized in a parallel rows (data not shown).

Expression of fusion proteins containing the Asn195Lys, Glu203Gly, and Arg89Leu mutations results in aberrant myocyte morphology, both in myotubes expressing these mutant proteins, and in adjacent myotubes that do not express the fusion proteins. Myotubes expressing these mutant proteins are thick, and characterized by angular and branched protrusions. Myotubes expressing the Asn195Lys and Glu203Gly protein constructs often contain parallel rows of nuclei (data not shown). Similar aberrant morphologies can be observed in the adjacent myotubes, which do not express the mutant fusion proteins. The expression of these mutant proteins also affects intercellular organization as the myotubes are arranged at various angles of up to 90 degrees relative to adjacent myotubes, and frequently grow across each other. When myotubes expressing the Glu203Gly and Arg89Leu mutations were allowed to differentiate for 8 days prior to processing, these effects on morphology and cellular organization were even more pronounced.

Expression of the GFP fusion protein containing the Arg377His mutation had a different effect on myotube morphology. Myotubes expressing this construct have a very segmented appearance. Furthermore, while the nuclei are clearly defined by indirect IF with the anti-desmin antibody in myotubes expressing the wild type and other mutant proteins, the nuclei in myotubes expressing the Arg377His mutation are poorly defined, or not at all evident (data not shown). Again, these effects are seen not only in myotubes expressing the Arg377His mutation, but also in adjacent myotubes that do not express the mutant fusion protein. The changes in appearance that are observed suggest that the nuclei in these myotubes are not membrane associated as in normal skeletal muscle, but internalized like a subset of the nuclei in skeletal muscle fibers from some patients with DCM.

In order to assess the effects of mutant prelamin A expression on cardiac myoblast differentiation, H9C2 myoblasts derived from neonatal rat heart were transfected with the prelamin A GFP fusion protein constructs, and induced to differentiate in the presence of retinoic acid. Exposure to retinoic acid causes H9C2 cells to differentiate towards a cardiac phenotype, which is characterized by parallel rows of nuclei as opposed to the linear arrangement observed in skeletal myotubes. In contrast to the distribution of the GFP fusion proteins seen in skeletal myotubes, the fusion protein constructs are partially limited to nuclear domains in differentiating H9C2 myotubes (data not shown). The number of nuclei containing the GFP fusion proteins in these myocytes ranges from 1 to 4, with the greatest number of myotubes containing two nuclei labeled by GFP. As normal cardiac myocytes contain two nuclei, these results may indicate that only a subset of nuclei in the H9C2 myotubes are active.

Expression of the fusion proteins containing the Arg60Gly and Leu85Arg mutations results in the formation of myotubes with mixed cardiac and skeletal morphologies (data not shown). These myotubes contain globular areas with nuclei in parallel rows, as well as projections that appear similar to skeletal myotubes containing linearly arranged nuclei. Expression of the protein constructs containing the Asn195Lys and Arg89Leu mutations results in the formation of aberrant, large randomly shaped myotubes (data not shown). In contrast, the Glu203Gly mutation appears to hinder myotube formation (data not shown). The nuclei in myotubes expressing the Glu203Gly fusion protein are typically farther removed from one another than in myotubes containing the wild type prelamin A fusion protein and other mutant constructs. In addition, the individual myoblast cell bodies are still evident and appear to be trapped in the early stages of intercellular fusion.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following Claims.

What is claimed is:

1. An isolated peptide selected from the group consisting of:
   a) a peptide consisting of SEQ ID NO:2;
   b) a peptide consisting of an amino acid sequence that differs from SEQ ID NO:2 by at least one substitution of an amino acid residue at a position of SEQ ID NO:2 selected from the group consisting of: 1, 2, 5, 6, 9, 10, 11, 12, 13, and 14, wherein the peptide promotes myoblast differentiation; and
   c) a peptide consisting of an amino acid sequence that differs from SEQ ID NO:2 by substitutions at positions 1, 5, 6, 9, 11, and 14, wherein the peptide promotes myoblast differentiation;
   wherein the amino acid residues substituted into positions 1, 2, 5, 6, 9, 10, 11, 12, 13, and 14 of SEQ ID NO:2 are those residues found at positions 1, 2, 5, 6, 9, 10, 11, 12, 13, and 14 in any of SEQ ID NO: 21, SEQ ID NO: 22, SEQ ID NO: 23, and SEQ ID NO: 24, respectively.

2. The isolated peptide of claim 1, wherein the peptide consists of an amino acid sequence that differs from SEQ ID NO:2 by one substitution, deletion or insertion of an amino acid residue at a position of SEQ ID NO:2 selected from the group consisting of: 1, 2, 5, 6, 9, 10, 11 and 12.

3. The isolated peptide of claim 1, wherein the peptide consists of SEQ ID NO:2.

4. The isolated peptide of claim 1, wherein the peptide comprises a modification selected from the group consisting of farnesylation, carboxymethylation, geranyl-geranylation, and complexing with a lipid carrier.

5. A composition comprising the isolated peptide of claim 1 and a pharmaceutically acceptable carrier.

6. A protein comprising a protein that is chemically or recombinantly conjugated to a agent that increases the half-life of the protein in cardiac or skeletal muscle tissue, wherein the protein is selected from the group consisting of:
   a) a protein comprising an amino acid sequence represented by SEQ ID NO:4;
   b) a protein consisting of at least 600 consecutive amino acids of SEQ ID NO:4, wherein the protein promotes myoblast differentiation; and
   c) a protein comprising an amino acid sequence that is at least 95% identical to SEQ ID NO:4, wherein the protein promotes myoblast differentiation.

7. A method to identify compounds that regulate myoblast activation and differentiation, comprising:
   a) contacting a prelamin A protein (SEQ ID NO:4) or a prelamin A pre peptide (SEQ ID NO:2) with a test compound under conditions suitable for binding of the prelamin A protein or prelamin A pre peptide by the test compound;
   b) detecting binding of the prelamin A protein or prelamin A pre peptide by the test compound;
   c) contacting myoblast with test compound of step b) that bind SEQ ID NO:2 or SEQ ID NO:4; and
   d) detecting myoblast differentiation in the presence and absence of said test compound, thereby identifying said test compound that regulates myoblast differentiation.

8. The isolated peptide of claim 1, wherein the peptide consists of an amino acid sequence that differs from SEQ ID NO:2 by at least one substitution of an amino acid residue at a position of SEQ ID NO:2 selected from the group consisting of: 1, 2, 5, 6, 9, 10, 11, 12, 13, and 14, wherein the peptide promotes myoblast differentiation.

9. The isolated peptide of claim 1, wherein the peptide consists of an amino acid sequence that differs from SEQ ID NO:2 by at least one substitution of an amino acid residue at a position of SEQ ID NO:2 selected from the group consisting of: 1, 2, 5, 6, 9, 10, and 11, wherein the peptide promotes myoblast differentiation.

10. The protein of claim 6, wherein the protein comprises an amino acid sequence that is at least 97% identical to SEQ ID NO:4.

11. The protein of claim 6, wherein the protein comprises an amino acid sequence that is at least 99% identical to SEQ ID NO:4.

12. The protein of claim 6, wherein the protein comprises an amino acid sequence represented by SEQ ID NO:4.

13. The protein of claim 6, wherein the protein comprises an amino acid sequence that is at least 95% identical to SEQ ID NO:4.

14. A method to promote myoblast differentiation, comprising administering to a myoblast stem cell the isolated peptide of claim 1.

15. The method of claim 14, wherein the isolated peptide consists of SEQ ID NO:2.

* * * * *

SEQUENCE LISTING

<160> NUMBER OF SEQ ID NOS: 24

<210> SEQ ID NO 1
<211> LENGTH: 57
<212> TYPE: DNA
<213> ORGANISM: Homo sapiens

<400> SEQUENCE: 1
ctcctgggca actccagccc ccgaacccag agcccccaga actgcagcat catgtaa      57

<210> SEQ ID NO 2
<211> LENGTH: 15
<212> TYPE: PRT
<213> ORGANISM: Homo sapiens

<400> SEQUENCE: 2

Leu Leu Gly Asn Ser Ser Pro Arg Thr Gln Ser Pro Gln Asn Cys
1               5                   10                  15

<210> SEQ ID NO 3
<211> LENGTH: 3181
<212> TYPE: DNA
<213> ORGANISM: Homo sapiens

<400> SEQUENCE: 3

```
actcagtgtt cgcgggagcg ccgcacctac accagccaac ccagatcccg aggtccgaca      60
gcgcccggcc cagatcccca cgcctgccag gagcaagccg agagccagcc ggccggcgca     120
ctccgactcc gagcagtctc tgtccttcga cccgagcccc cgcgcctttc cgggacccct     180
gccccgcggg cagcgctgcc aacctgccgg ccatggagac cccgtcccag cggcgcgcca     240
cccgcagcgg ggcgcaggcc agctccactc cgctgtcgcc cacccgcatc acccggctgc     300
aggagaagga ggacctgcag gagctcaatg atcgcttggc ggtctacatc gaccgtgtgc     360
gctcgctgga aacggagaac gcagggctgc gccttcgcat caccgagtct gaagaggtgg     420
tcagccgcga ggtgtccggc atcaaggccg cctacgaggc cgagctcggg gatgcccgca     480
agacccttga ctcagtagcc aaggagcgcg cccgcctgca gctggagctg agcaaagtgc     540
gtgaggagtt taaggagctg aaagcgcgca ataccaagaa ggagggtgac ctgatagctg     600
ctcaggctcg gctgaaggac ctggaggctc tgctgaactc caaggaggcc gcactgagca     660
ctgctctcag tgagaagcgc acgctggagg gcgagctgca tgatctgcgg ggccaggtgg     720
ccaagcttga ggcagcccta ggtgaggcca agaagcaact tcaggatgag atgctgcggc     780
gggtggatgc tgaacaggg ctgcagacca tgaaggagga actggacttc cagaagaaca     840
tctacagtga ggagctgcgt gagaccaagc gccgtcatga cccgactg tggagattg     900
acaatgggaa gcagcgtgag tttgagagcc ggctggcgga tgcgctgcag gaactgcggg     960
cccagcatga ggaccaggtg gagcagtata agaaggagct ggagaagact tattctgcca    1020
agctggacaa tgccaggcag tctgctgaga ggaacagcaa cctggtgggg ctgccccacg    1080
aggagctgca gcagtcgcgc atccgcatcg acagcctctc tgcccagctc agccagctcc    1140
agaagcagct ggcagccaag gaggcgaagc ttcgagacct ggaggactca ctggcccgtg    1200
agcgggacac cagccggcgg ctgctggcgg aaaaggagcg ggagatggcc gagatgcggg    1260
caaggatgca gcagcagctg gacgagtacc aggagcttct ggacatcaag ctggcccctgg    1320
acatggagat ccacgcctac cgcaagctct tggagggcga ggaggagagg ctacgcctgt    1380
cccccagccc tacctcgcag cgcagccgtg gccgtgcttc ctctcactca tcccagacac    1440
agggtggggg cagcgtcacc aaaaagcgca aactggagtc cactgagagc cgcagcagct    1500
tctcacagca cgcacgcact agcggggcgc tggccgtgga ggaggtggat gaggagggca    1560
agtttgtccg gctgcgcaac aagtccaatg aggaccagtc catgggcaat tggcagatca    1620
agcgccagaa tggagatgat cccttgctga cttaccggtt cccaccaaag ttcaccctga    1680
aggctgggca ggtggtgacg atctgggctg caggagctgg gccacccac agccccccta    1740
ccgacctggt gtgaaggca cagaacacct ggggctgcgg aacagcctg cgtacggctc    1800
tcatcaactc cactggggaa gaagtggcca tgcgcaagct ggtgcgctca gtgactgtgg    1860
ttgaggacga cgaggatgag gatggagatg acctgctcca tcaccaccac ggctcccact    1920
gcagcagctc gggggacccc gctgagtaca acctgcgctc gcgcaccgtg ctgtgcggga    1980
```

-continued

```
cctgcgggca gcctgccgac aaggcatctg ccagcggctc aggagcccag gtgggcggac      2040
ccatctcctc tggctcttct gcctccagtg tcacggtcac tcgcagctac cgcagtgtgg      2100
ggggcagtgg gggtggcagc ttcggggaca atctggtcac ccgctcctac ctcctgggca      2160
actccagccc ccgaacccag agcccccaga actgcagcat catgtaatct gggacctgcc      2220 aggcagggt gggggtggag gcttcctgcg tcctcctcac ctcatgccca ccccctgccc       2280
tgcacgtcat gggagggggc ttgaagccaa agaaaaataa ccctttggtt ttttcttct       2340 gtattttttt ttctaagaga agttattttc tacagtggtt ttatactgaa ggaaaaacac      2400
aagcaaaaaa aaaaaaagc atctatctca tctatctcaa tcctaatttc tcctcccttc       2460
cttttccctg cttccaggaa actccacatc tgccttaaaa ccaagagggg cttcctctag      2520
aagccaaggg aaagggggtgc ttttatagag gctagcttct gcttttctgc cctggctgct    2580
gcccccaccc cggggaccct gtgacatggt gcctgagagg caggcataga ggcttctccg      2640
ccagcctcct ctggacggca ggctcactgc caggccagcc tccgagaggg agagagagag      2700
agagaggaca gcttgagccg ggcccctggg cttggcctgc tgtgattcca ctacacctgg      2760
ctgaggttcc tctgcctgcc ccgccccag tccccacccc tgcccccagc ccgggggtga       2820
gtccattctc ccaggtacca gctgcgcttg cttttctgta ttttatttag acaagagatg      2880
ggaatgaggt gggaggtgga agaagggaga agaaaggtga gtttgagctg ccttccctag      2940
ctttagaccc tgggtgggct ctgtgcagtc actggaggtt gaagccaagt gggggtgctgg     3000 gaggagggag agggaggtca ctggaaaggg gagagcctgc tggcacccac cgtggaggag      3060
gaaggcaaga gggggtggag gggtgtggca gtggttttgg caaacgctaa agagcccttg      3120 cctcccatt tccatctgc accccttctc tcctccccaa atcaatacac tagttgtttc       3180
t                                                                       3181
```

<210> SEQ ID NO 4
<211> LENGTH: 664
<212> TYPE: PRT
<213> ORGANISM: Homo sapiens

<400> SEQUENCE: 4

```
Met Glu Thr Pro Ser Gln Arg Arg Ala Thr Arg Ser Gly Ala Gln Ala
1               5                   10                  15

Ser Ser Thr Pro Leu Ser Pro Thr Arg Ile Thr Arg Leu Gln Glu Lys
            20                  25                  30

Glu Asp Leu Gln Glu Leu Asn Asp Arg Leu Ala Val Tyr Ile Asp Arg
        35                  40                  45

Val Arg Ser Leu Glu Thr Glu Asn Ala Gly Leu Arg Leu Arg Ile Thr
    50                  55                  60

Glu Ser Glu Glu Val Val Ser Arg Glu Val Ser Gly Ile Lys Ala Ala
65                  70                  75                  80

Tyr Glu Ala Glu Leu Gly Asp Ala Arg Lys Thr Leu Asp Ser Val Ala
                85                  90                  95

Lys Glu Arg Ala Arg Leu Gln Leu Glu Leu Ser Lys Val Arg Glu Glu
            100                 105                 110

Phe Lys Glu Leu Lys Ala Arg Asn Thr Lys Lys Glu Gly Asp Leu Ile
        115                 120                 125

Ala Ala Gln Ala Arg Leu Lys Asp Leu Glu Ala Leu Leu Asn Ser Lys
    130                 135                 140

Glu Ala Ala Leu Ser Thr Ala Leu Ser Glu Lys Arg Thr Leu Glu Gly
145                 150                 155                 160
```

```
Glu Leu His Asp Leu Arg Gly Gln Val Ala Lys Leu Glu Ala Ala Leu
                165                 170                 175
Gly Glu Ala Lys Lys Gln Leu Gln Asp Glu Met Leu Arg Arg Val Asp
            180                 185                 190
Ala Glu Asn Arg Leu Gln Thr Met Lys Glu Glu Leu Asp Phe Gln Lys
        195                 200                 205
Asn Ile Tyr Ser Glu Glu Leu Arg Glu Thr Lys Arg Arg His Glu Thr
    210                 215                 220
Arg Leu Val Glu Ile Asp Asn Gly Lys Gln Arg Glu Phe Glu Ser Arg
225                 230                 235                 240
Leu Ala Asp Ala Leu Gln Glu Leu Arg Ala Gln His Glu Asp Gln Val
                245                 250                 255
Glu Gln Tyr Lys Lys Glu Leu Glu Lys Thr Tyr Ser Ala Lys Leu Asp
            260                 265                 270
Asn Ala Arg Gln Ser Ala Glu Arg Asn Ser Asn Leu Val Gly Ala Ala
        275                 280                 285
His Glu Glu Leu Gln Gln Ser Arg Ile Arg Ile Asp Ser Leu Ser Ala
    290                 295                 300
Gln Leu Ser Gln Leu Gln Lys Gln Leu Ala Ala Lys Glu Ala Lys Leu
305                 310                 315                 320
Arg Asp Leu Glu Asp Ser Leu Ala Arg Glu Arg Asp Thr Ser Arg Arg
                325                 330                 335
Leu Leu Ala Glu Lys Glu Arg Glu Met Ala Glu Met Arg Ala Arg Met
            340                 345                 350
Gln Gln Gln Leu Asp Glu Tyr Gln Glu Leu Leu Asp Ile Lys Leu Ala
        355                 360                 365
Leu Asp Met Glu Ile His Ala Tyr Arg Lys Leu Leu Glu Gly Glu Glu
    370                 375                 380
Glu Arg Leu Arg Leu Ser Pro Ser Pro Thr Ser Gln Arg Ser Arg Gly
385                 390                 395                 400
Arg Ala Ser Ser His Ser Ser Gln Thr Gln Gly Gly Gly Ser Val Thr
                405                 410                 415
Lys Lys Arg Lys Leu Glu Ser Thr Glu Ser Arg Ser Ser Phe Ser Gln
            420                 425                 430
His Ala Arg Thr Ser Gly Arg Val Ala Val Glu Glu Val Asp Glu Glu
        435                 440                 445
Gly Lys Phe Val Arg Leu Arg Asn Lys Ser Asn Glu Asp Gln Ser Met
    450                 455                 460
Gly Asn Trp Gln Ile Lys Arg Gln Asn Gly Asp Asp Pro Leu Leu Thr
465                 470                 475                 480
Tyr Arg Phe Pro Pro Lys Phe Thr Leu Lys Ala Gly Gln Val Val Thr
                485                 490                 495
Ile Trp Ala Ala Gly Ala Gly Ala Thr His Ser Pro Thr Asp Leu
            500                 505                 510
Val Trp Lys Ala Gln Asn Thr Trp Gly Cys Gly Asn Ser Leu Arg Thr
        515                 520                 525
Ala Leu Ile Asn Ser Thr Gly Glu Glu Val Ala Met Arg Lys Leu Val
    530                 535                 540
Arg Ser Val Thr Val Val Glu Asp Asp Glu Asp Glu Asp Gly Asp Asp
545                 550                 555                 560
Leu Leu His His His His His Gly Ser His Cys Ser Ser Ser Gly Asp Pro
                565                 570                 575
```

```
Ala Glu Tyr Asn Leu Arg Ser Arg Thr Val Leu Cys Gly Thr Cys Gly
            580                 585                 590

Gln Pro Ala Asp Lys Ala Ser Ala Ser Gly Ser Gly Ala Gln Val Gly
            595                 600                 605

Gly Pro Ile Ser Ser Gly Ser Ser Ala Ser Ser Val Thr Val Thr Arg
            610                 615                 620

Ser Tyr Arg Ser Val Gly Gly Ser Gly Gly Gly Ser Phe Gly Asp Asn
625                 630                 635                 640

Leu Val Thr Arg Ser Tyr Leu Leu Gly Asn Ser Ser Pro Arg Thr Gln
                645                 650                 655

Ser Pro Gln Asn Cys Ser Ile Met
            660

<210> SEQ ID NO 5
<211> LENGTH: 1938
<212> TYPE: DNA
<213> ORGANISM: Homo sapiens

<400> SEQUENCE: 5
atggagaccc cgtcccagcg gcgcgccacc cgcagcgggg cgcaggccag ctccactccg      60
ctgtcgccca cccgcatcac ccggctgcag agaaggagg acctgcagga gctcaatgat     120
cgcttggcgg tctacatcga ccgtgtgcgc tcgctggaaa cggagaacgc agggctgcgc     180
cttcgcatca ccgagtctga agaggtggtc agccgcgagg tgtccggcat caaggccgcc     240
tacgaggcca agctcgggga tgcccgcaag acccttgact cagtagccaa ggagcgcgcc     300
cgcctgcagc tggagctgag caaagtgcgt gaggagttta aggagctgaa agcgcgcaat     360
accaagaagg agggtgacct gatagctgct caggctcggc tgaaggacct ggaggctctg     420
ctgaactcca aggaggccgc actgagcact gctctcagtg agaagcgcac gctggagggc     480
gagctgcatg atctgcgggg ccaggtggcc aagcttgagg cagccctagg tgaggccaag     540
aagcaacttc aggatgagat gctgcggcgg gtggatgctg agaacaggct gcagaccatg     600
aaggaggaac tggacttcca gaagaacatc tacagtgagg agctgcgtga gaccaagcgc     660
cgtcatgaga cccgactggt ggagattgac aatgggaagc agcgtgagtt tgagagccgg     720
ctggcggatg cgctgcagga actgcgggcc cagcatgagg accaggtgga gcagtataag     780
aaggagctgg agaagactta ttctgccaag ctggacaatg ccaggcagtc tgctgagagg     840
aacagcaacc tggtggggc tgcccacgag gagctgcagc agtcgcgcat ccgcatcgac     900
agcctctctg cccagctcag ccagctccag aagcagctgg cagccaagga ggcgaagctt     960
cgagacctgg aggactcact ggcccgtgag cgggacacca gccggcggct gctggcggaa    1020
aaggagcggg agatggccga gatgcgggca aggatgcagc agcagctgga cgagtaccag    1080
gagcttctgg acatcaagct ggccctggac atggagatcc acgcctaccg caagctcttg    1140
gagggcgagg aggagaggct acgcctgtcc ccagccctaa cctcgcagcg cagccgtggc    1200
cgtgcttcct ctcactcatc ccagacacag ggtgggggca gcgtcaccaa aaagcgcaaa    1260
ctggagtcca ctgagagccg cagcagcttc tcacagcacg cacgcactag cgggcgcgtg    1320
gccgtggagg aggtggatga ggagggcaag tttgtccggc tgcgcaacaa gtccaatgag    1380
gaccagtcca tggcaattg gcagatcaag cgccagaatg agatgatccc ttgctgact    1440 taccggttcc caccaaagtt cacccctgaag gctgggcagg tggtgacgat ctgggctgca    1500
ggagctgggg ccacccacag cccccctacc gacctggtgt ggaaggcaca gaacacctgg    1560
ggctgcggga acagcctgcg tacggctctc atcaactcca ctggggaaga agtggccatg    1620
```

```
cgcaagctgg tgcgctcagt gactgtggtt gaggacgacg aggatgagga tggagatgac    1680
ctgctccatc accaccacgg ctcccactgc agcagctcgg gggaccccgc tgagtacaac    1740
ctgcgctcgc gcaccgtgct gtgcgggacc tgcgggcagc tgccgacaa  ggcatctgcc    1800 agcggctcag gagcccaggt gggcggaccc atctcctctg gctcttctgc ctccagtgtc    1860
acggtcactc gcagctaccg cagtgtgggg ggcagtgggg gtggcagctt cggggacaat    1920
ctggtcaccc gctcctac                                                  1938
```

<210> SEQ ID NO 6
<211> LENGTH: 646
<212> TYPE: PRT
<213> ORGANISM: Homo sapiens

<400> SEQUENCE: 6

```
Met Glu Thr Pro Ser Gln Arg Arg Ala Thr Arg Ser Gly Ala Gln Ala
1               5                   10                  15

Ser Ser Thr Pro Leu Ser Pro Thr Arg Ile Thr Arg Leu Gln Glu Lys
                20                  25                  30

Glu Asp Leu Gln Glu Leu Asn Asp Arg Leu Ala Val Tyr Ile Asp Arg
            35                  40                  45

Val Arg Ser Leu Glu Thr Glu Asn Ala Gly Leu Arg Leu Arg Ile Thr
50                  55                  60

Glu Ser Glu Glu Val Val Ser Arg Glu Val Ser Gly Ile Lys Ala Ala
65                  70                  75                  80

Tyr Glu Ala Glu Leu Gly Asp Ala Arg Lys Thr Leu Asp Ser Val Ala
                85                  90                  95

Lys Glu Arg Ala Arg Leu Gln Leu Glu Leu Ser Lys Val Arg Glu Glu
            100                 105                 110

Phe Lys Glu Leu Lys Ala Arg Asn Thr Lys Lys Glu Gly Asp Leu Ile
        115                 120                 125

Ala Ala Gln Ala Arg Leu Lys Asp Leu Glu Ala Leu Leu Asn Ser Lys
130                 135                 140

Glu Ala Ala Leu Ser Thr Ala Leu Ser Glu Lys Arg Thr Leu Glu Gly
145                 150                 155                 160

Glu Leu His Asp Leu Arg Gly Gln Val Ala Lys Leu Glu Ala Ala Leu
                165                 170                 175

Gly Glu Ala Lys Lys Gln Leu Gln Asp Glu Met Leu Arg Arg Val Asp
            180                 185                 190

Ala Glu Asn Arg Leu Gln Thr Met Lys Glu Glu Leu Asp Phe Gln Lys
        195                 200                 205

Asn Ile Tyr Ser Glu Glu Leu Arg Glu Thr Lys Arg Arg His Glu Thr
    210                 215                 220

Arg Leu Val Glu Ile Asp Asn Gly Lys Gln Arg Glu Phe Glu Ser Arg
225                 230                 235                 240

Leu Ala Asp Ala Leu Gln Glu Leu Arg Ala Gln His Glu Asp Gln Val
                245                 250                 255

Glu Gln Tyr Lys Lys Glu Leu Glu Lys Thr Tyr Ser Ala Lys Leu Asp
            260                 265                 270

Asn Ala Arg Gln Ser Ala Glu Arg Asn Ser Asn Leu Val Gly Ala Ala
        275                 280                 285

His Glu Glu Leu Gln Gln Ser Arg Ile Arg Ile Asp Ser Leu Ser Ala
    290                 295                 300

Gln Leu Ser Gln Leu Gln Lys Gln Leu Ala Ala Lys Glu Ala Lys Leu
```

```
305                 310                 315                 320
Arg Asp Leu Glu Asp Ser Leu Ala Arg Glu Arg Asp Thr Ser Arg Arg
                325                 330                 335

Leu Leu Ala Glu Lys Glu Arg Glu Met Ala Glu Met Arg Ala Arg Met
            340                 345                 350

Gln Gln Gln Leu Asp Glu Tyr Gln Leu Leu Asp Ile Lys Leu Ala
        355                 360                 365

Leu Asp Met Glu Ile His Ala Tyr Arg Lys Leu Leu Glu Gly Glu
    370                 375                 380

Glu Arg Leu Arg Leu Ser Pro Ser Pro Thr Ser Gln Arg Ser Arg Gly
385                 390                 395                 400

Arg Ala Ser Ser His Ser Ser Gln Thr Gln Gly Gly Ser Val Thr
                405                 410                 415

Lys Lys Arg Lys Leu Glu Ser Thr Glu Ser Arg Ser Ser Phe Ser Gln
                420                 425                 430

His Ala Arg Thr Ser Gly Arg Val Ala Val Glu Val Asp Glu Glu
            435                 440                 445

Gly Lys Phe Val Arg Leu Arg Asn Lys Ser Asn Glu Asp Gln Ser Met
450                 455                 460

Gly Asn Trp Gln Ile Lys Arg Gln Asn Gly Asp Asp Pro Leu Leu Thr
465                 470                 475                 480

Tyr Arg Phe Pro Pro Lys Phe Thr Leu Lys Ala Gly Gln Val Val Thr
                485                 490                 495

Ile Trp Ala Ala Gly Ala Gly Ala Thr His Ser Pro Thr Asp Leu
            500                 505                 510

Val Trp Lys Ala Gln Asn Thr Trp Gly Cys Gly Asn Ser Leu Arg Thr
            515                 520                 525

Ala Leu Ile Asn Ser Thr Gly Glu Glu Val Ala Met Arg Lys Leu Val
            530                 535                 540

Arg Ser Val Thr Val Val Glu Asp Asp Glu Asp Gly Asp Asp
545                 550                 555                 560

Leu Leu His His His Gly Ser His Cys Ser Ser Ser Gly Asp Pro
                565                 570                 575

Ala Glu Tyr Asn Leu Arg Ser Arg Thr Val Leu Cys Gly Thr Cys Gly
            580                 585                 590

Gln Pro Ala Asp Lys Ala Ser Ala Ser Gly Ser Gly Ala Gln Val Gly
            595                 600                 605

Gly Pro Ile Ser Ser Gly Ser Ser Ala Ser Ser Val Thr Val Thr Arg
        610                 615                 620

Ser Tyr Arg Ser Val Gly Gly Ser Gly Gly Ser Phe Gly Asp Asn
625                 630                 635                 640

Leu Val Thr Arg Ser Tyr
                645

<210> SEQ ID NO 7
<211> LENGTH: 2032
<212> TYPE: DNA
<213> ORGANISM: Homo sapiens

<400> SEQUENCE: 7
actcagtgtt cgcgggagcg ccgcacctac accagccaac ccagatcccg aggtccgaca    60
gcgcccggcc cagatcccca cgcctgccag gagcaagccg agagccagcc ggccggcgca   120
ctccgactcc gagcagtctc tgtccttcga cccgagcccc gcgcccttc cgggacccct    180
```

| | |
|---|---|
| gccccgcggg cagcgctgcc aacctgccgg ccatggagac cccgtcccag cggcgcgcca | 240 |
| cccgcagcgg ggcgcaggcc agctccactc cgctgtcgcc cacccgcatc acccggctgc | 300 |
| aggagaagga ggacctgcag gagctcaatg atcgcttggc ggtctacatc gaccgtgtgc | 360 |
| gctcgctgga aacggagaac gcagggctgc gccttcgcat caccgagtct gaagaggtgg | 420 |
| tcagccgcga ggtgtccggc atcaaggccc cctacgaggc cgagctcggg gatgcccgca | 480 |
| agacccttga ctcagtagcc aaggagcgcg cccgcctgca gctggagctg agcaaagtgc | 540 |
| gtgaggagtt taaggagctg aaagcgcgca ataccaagaa ggagggtgac ctgatagctg | 600 |
| ctcaggctcg gctgaaggac ctggaggctc tgctgaactc caaggaggcc gcactgagca | 660 |
| ctgctctcag tgagaagcgc acgctggagg gcgagctgca tgatctgcgg ggccaggtgg | 720 |
| ccaagcttga ggcagcccta ggtgaggcca gaagcaact tcaggatgag atgctgcggc | 780 |
| gggtggatgc tgagaacagg ctgcagacca tgaaggagga actggacttc cagaagaaca | 840 |
| tctacagtga ggagctgcgt gagaccaagc gccgtcatga cccgactg gtggagattg | 900 |
| acaatgggaa gcagcgtgag tttgagagcc ggctggcgga tgcgctgcag gaactgcggg | 960 |
| cccagcatga ggaccaggtg gagcagtata agaaggagct ggagaagact tattctgcca | 1020 |
| agctggacaa tgccaggcag tctgctgaga ggaacagcaa cctggtgggg gctgcccacg | 1080 |
| aggagctgca gcagtcgcgc atccgcatcg acagcctctc tgcccagctc agccagctcc | 1140 |
| agaagcagct ggcagccaag gaggcgaagc ttcgagacct ggaggactca ctggcccgtg | 1200 |
| agcgggacac cagccggcgg ctgctggcgg aaaaggagcg ggagatggcc gagatgcggg | 1260 |
| caaggatgca gcagcagctg gacgagtacc aggagcttct ggacatcaag ctggccctgg | 1320 |
| acatggagat ccacgcctac cgcaagctct tggagggcga ggaggagagg ctacgcctgt | 1380 |
| cccccagccc tacctcgcag cgcagccgtg gccgtgcttc ctctcactca tcccagacac | 1440 |
| agggtggggg cagcgtcacc aaaaagcgca aactggagtc cactgagagc cgcagcagct | 1500 |
| tctcacagca cgcacgcact agcgggcgcg tggccgtgga ggaggtggat gaggagggca | 1560 |
| agtttgtccg gctgcgcaac aagtccaatg aggaccagtc catgggcaat tggcagatca | 1620 |
| agcgccagaa tggagatgat cccttgctga cttaccggtt cccaccaaag ttcaccctga | 1680 |
| aggctgggca ggtggtgacg atctgggctg caggagctgg ggccacccac agccccccta | 1740 |
| ccgacctggt gtggaaggca cagaacacct ggggctgcgg gaacagcctg cgtacggctc | 1800 |
| tcatcaactc cactggggaa gaagtggcca tgcgcaagct ggtgcgctca gtgactgtgg | 1860 |
| ttgaggacga cgaggatgag gatggagatg acctgctcca tcaccaccac gtgagtggta | 1920 |
| gccgccgctg aggccgagcc tgcactgggg ccacccagcc aggcctgggg gcagcctctc | 1980 |
| cccagcctcc ccgtgccaaa aatcttttca ttaaagaatg ttttggaact tt | 2032 |

<210> SEQ ID NO 8
<211> LENGTH: 2354
<212> TYPE: DNA
<213> ORGANISM: Mus musculus

<400> SEQUENCE: 8

| | |
|---|---|
| ccacgcctgc caggagcgag cttcgccggc tcgctgtccc cctgagcagc ctctgtcctt | 60 |
| ctgtccaagt cccgcgccct tctcgggacc cctgcccagc gggcagcact gtcaccctgc | 120 |
| cggccatgga gaccccgtca cagcggcgcg ccacccgcag tggggcgcag gccagctcta | 180 |
| ccccactgtc gcccactcgg atcccggc tgcaggagaa ggaggacctg caggagctca | 240 |
| atgaccgcct ggccgtgtac atcgatcgcg tgcgttccct ggagaccgag aacgcggggc | 300 |

```
tgcgccttcg catcactgag tctgaagagg tggtcagccg agaggtgtcc ggcatcaagg    360
cggcctacga ggccgagctg ggggatgccc gcaagaccct tgattctgtg ccaaggagc    420 gcgcccgcct ccagctagag ctgagcaaag tgcgtgagga gttcaaggag ctgaaggctc    480
gcaacaccaa gaaggagggg gacttgttgg ctgcgcaggc ccggctcaag gacctcgagg    540
ctcttctcaa ctccaaggaa gctgccctga gcactgctct cagtgagaag cgcacattgg    600
agggcgagct ccatgacctg cgggggcagg tagccaagct tgaggcggcc ctgggagagg    660
ctaagaagca gcttcaggat gagatgctga ggcgagtgga tgctgagaac aggctacaga    720
cgctgaagga ggagcttgac ttccagaaga acatttacag cgaggaactg cgtgagacca    780
agcgccggca tgagacgcgg cttgtggaga tcgataacgg gaagcagcga gagtttgaga    840
gccggctggc agatgccctg caggagctgc gggctcagca tgaggaccag gtggaacagt    900
ataagaagga gctagaaaag acatactccg ccaagctgga taatgccagg cagtctgctg    960
agaggaacag caacctcgtg ggggctgccc atgaggaact gcagcagtct cgaatccgca   1020
ttgacagcct ctcggcccag ctcagccagc tccaaaagca gttggcagcc aaggaggcaa   1080
agctgcgtga cctggaggac tcgctggccc gtgagcgcga taccagccgg cgcctgctgg   1140
ctgagaaaga gcgagagatg gcggagatgc gggcgaggat gcagcagcag ctggacgagt   1200
accaggagct gctggacatc aagctggccc tggacatgga gatccatgcc tatcgaaagc   1260
tgctggaggg cgaggaggag aggctgcgcc tgtcccccag ccctacctcg cagcgcagcc   1320
gtggccgcgc ctcctcccac tcatcccagt ctcagggtgg aggcagcgtc accaaaaagc   1380
gcaagctgga gtcttccgag agccggagca gcttctcgca gcatgctcgc actagcgggc   1440
gtgtggcggt agaggaagtc gatgaagagg gaaagttcgt gcggctgcgc aacaagtcca   1500
acgaggacca gtccatgggc aactggcaga tcaggcgtca gaatggtgac gatcctttga   1560
tgacctatcg cttcccaccg aagttccacc taaaggctgg gcaggtggtg acgatctggg   1620
cttcaggagc tggggccacc catagccccc ctactgactt ggtgtggaag gcgcagaaca   1680 cctgggctg tgggagcagc cttcgcaccg ctctcatcaa ctccactgga gaagaagtgg   1740
ccatgcgcaa gctggtgcgc tcactgacca tggttgagga caatgaggat gacgacgagg   1800
atggagaaga gctcctccat caccaccgtg gttcccactg cagcggctcg ggggaccccg   1860
ctgagtacaa cctgcgctca cgcaccgtgc tgtgcgggac gtgtgggcag cctgctgaca   1920
aggctgccgg tggagcggga gcccaggtgg gcggatccat ctcctctggc tcttctgcct   1980
ccagtgtcac agtcactcga agcttccgca gtgtgggggg cagtgggggt ggcagcttcg   2040
gggacaacct agtcacccgc tcctacctcc tgggcaactc cagtcccggg agccagagct   2100
cccagaactg cagcatcatg taatctggga cctgccaggc agggctgggg gcagaggcca   2160
cctgctcccc cctcaccaca tgccacctcc tgtctgctcc ttaggagagc aggcctgaag   2220
ccaaagaaaa atttatcccc tgcctttggt tttttttttt ttcttctat ttttttttc    2280 tttttctaag agaagttatt ttctacagtg gttttatact gaaggaaaaa ctcaagcaaa   2340
aaaaaaaaaa aaaa                                                    2354
```

<210> SEQ ID NO 9
<211> LENGTH: 665
<212> TYPE: PRT
<213> ORGANISM: Mus musculus

<400> SEQUENCE: 9

-continued

```
Met Glu Thr Pro Ser Gln Arg Arg Ala Thr Arg Ser Gly Ala Gln Ala
1               5                   10                  15

Ser Ser Thr Pro Leu Ser Pro Thr Arg Ile Thr Arg Leu Gln Glu Lys
                20                  25                  30

Glu Asp Leu Gln Glu Leu Asn Asp Arg Leu Ala Val Tyr Ile Asp Arg
            35                  40                  45

Val Arg Ser Leu Glu Thr Glu Asn Ala Gly Leu Arg Leu Arg Ile Thr
    50                  55                  60

Glu Ser Glu Glu Val Val Ser Arg Glu Val Ser Gly Ile Lys Ala Ala
65                  70                  75                  80

Tyr Glu Ala Glu Leu Gly Asp Ala Arg Lys Thr Leu Asp Ser Val Ala
                85                  90                  95

Lys Glu Arg Ala Arg Leu Gln Leu Glu Leu Ser Lys Val Arg Glu Glu
                100                 105                 110

Phe Lys Glu Leu Lys Ala Arg Asn Thr Lys Lys Glu Gly Asp Leu Leu
            115                 120                 125

Ala Ala Gln Ala Arg Leu Lys Asp Leu Glu Ala Leu Leu Asn Ser Lys
    130                 135                 140

Glu Ala Ala Leu Ser Thr Ala Leu Ser Glu Lys Arg Thr Leu Glu Gly
145                 150                 155                 160

Glu Leu His Asp Leu Arg Gly Gln Val Ala Lys Leu Glu Ala Ala Leu
                165                 170                 175

Gly Glu Ala Lys Lys Gln Leu Gln Asp Glu Met Leu Arg Arg Val Asp
                180                 185                 190

Ala Glu Asn Arg Leu Gln Thr Leu Lys Glu Glu Leu Asp Phe Gln Lys
            195                 200                 205

Asn Ile Tyr Ser Glu Glu Leu Arg Glu Thr Lys Arg Arg His Glu Thr
    210                 215                 220

Arg Leu Val Glu Ile Asp Asn Gly Lys Gln Arg Glu Phe Glu Ser Arg
225                 230                 235                 240

Leu Ala Asp Ala Leu Gln Glu Leu Arg Ala Gln His Glu Asp Gln Val
                245                 250                 255

Glu Gln Tyr Lys Lys Glu Leu Glu Lys Thr Tyr Ser Ala Lys Leu Asp
                260                 265                 270

Asn Ala Arg Gln Ser Ala Glu Arg Asn Ser Asn Leu Val Gly Ala Ala
            275                 280                 285

His Glu Glu Leu Gln Gln Ser Arg Ile Arg Ile Asp Ser Leu Ser Ala
    290                 295                 300

Gln Leu Ser Gln Leu Gln Lys Gln Leu Ala Ala Lys Glu Ala Lys Leu
305                 310                 315                 320

Arg Asp Leu Glu Asp Ser Leu Ala Arg Glu Arg Asp Thr Ser Arg Arg
                325                 330                 335

Leu Leu Ala Glu Lys Glu Arg Glu Met Ala Glu Met Arg Ala Arg Met
                340                 345                 350

Gln Gln Gln Leu Asp Glu Tyr Gln Glu Leu Leu Asp Ile Lys Leu Ala
            355                 360                 365

Leu Asp Met Glu Ile His Ala Tyr Arg Lys Leu Leu Glu Gly Glu Glu
    370                 375                 380

Glu Arg Leu Arg Leu Ser Pro Ser Pro Thr Ser Gln Arg Ser Arg Gly
385                 390                 395                 400

Arg Ala Ser Ser His Ser Ser Gln Ser Gln Gly Gly Gly Ser Val Thr
                405                 410                 415

Lys Lys Arg Lys Leu Glu Ser Ser Glu Ser Arg Ser Ser Phe Ser Gln
```

```
                420             425             430
His Ala Arg Thr Ser Gly Arg Val Ala Val Glu Glu Val Asp Glu Glu
            435                 440                 445

Gly Lys Phe Val Arg Leu Arg Asn Lys Ser Asn Glu Asp Gln Ser Met
450                 455                 460

Gly Asn Trp Gln Ile Arg Arg Gln Asn Gly Asp Asp Pro Leu Met Thr
465                 470                 475                 480

Tyr Arg Phe Pro Pro Lys Phe Thr Leu Lys Ala Gly Gln Val Val Thr
                485                 490                 495

Ile Trp Ala Ser Gly Ala Gly Ala Thr His Ser Pro Pro Thr Asp Leu
            500                 505                 510

Val Trp Lys Ala Gln Asn Thr Trp Gly Cys Gly Ser Ser Leu Arg Thr
            515                 520                 525

Ala Leu Ile Asn Ser Thr Gly Glu Glu Val Ala Met Arg Lys Leu Val
            530                 535                 540

Arg Ser Leu Thr Met Val Glu Asp Asn Glu Asp Asp Glu Asp Gly
545                 550                 555                 560

Glu Glu Leu Leu His His His Arg Gly Ser His Cys Ser Gly Ser Gly
                565                 570                 575

Asp Pro Ala Glu Tyr Asn Leu Arg Ser Arg Thr Val Leu Cys Gly Thr
            580                 585                 590

Cys Gly Gln Pro Ala Asp Lys Ala Ala Gly Ala Gly Ala Gln Val
            595                 600                 605

Gly Gly Ser Ile Ser Ser Gly Ser Ser Ala Ser Ser Val Thr Val Thr
            610                 615                 620

Arg Ser Phe Arg Ser Val Gly Gly Ser Gly Gly Ser Phe Gly Asp
625                 630                 635                 640

Asn Leu Val Thr Arg Ser Tyr Leu Leu Gly Asn Ser Ser Pro Arg Ser
                645                 650                 655

Gln Ser Ser Gln Asn Cys Ser Ile Met
            660                 665

<210> SEQ ID NO 10
<211> LENGTH: 2388
<212> TYPE: DNA
<213> ORGANISM: Gallus gallus

<400> SEQUENCE: 10 cccccaccg ccccccaccg cccccaccc gcggtccccc tcggagctcc gccgcgcccc        60
tccgtgcgcc gtccgccgtc cgccgtccgc cgccccccga cggctcttct ccgcccgccc       120
ggcgcccccg cagcgttccc cgcccgccgc ccgccgtccc ggggtcgcac cgccgccccc       180
cgcccagccg ccatgtccac cccgtcccag cggaggagcg gccgcggcgg cggcccttcg       240
gggacccctc tgtccccgac gcgcatcacc cgactgcagg agaaggagga cctgcaggag       300
ctcaacgacc gcctggccgt ctacatcgac aaagtgcgct ctctggagct cgagaacgcc       360
gggctgcgcc tgcgcatcac cgagtccgag gaggtggtga gccgggaggt gtcgggcatt       420
aaggccgcct acgaggccga gttggcggac gcgaggaaga cgttggattc ggtggcgaag       480
gagcgggcgc gcctgcagct cgagctgagc aaagtgcgcg aggagcacaa ggagctgaag       540
gccaggaatg ccaagaagga ggcggaccte ctggcggccc aggcgcgcct taaggacctc       600
gaggctctgc tcaactccaa ggaggccgcg ctgtccacgg cgctgggcga agaggaaac        660 ctggagaacg aagtgcggga cctgagggcg caggtggcca gttggagggg cgcgctgagc       720
```

-continued

```
gaggccaaga agcagctgca ggatgagatg ctgcgccgcg tggacgccga gaaccgcctg      780
cagaccctga aggaggagtt ggagttccag aagaacattt acagcgagga gctgcgggag      840
accaaacggc ggcacgagac gcgcctggtg gagatcgaca acgggcggca gcaggaattc      900
gagagcaaat tggccgaggc gctgcaggac ctgcggcggc agcacgagga tcagatccgg      960
cactaccgcg acgagctgga aaagacctac ggggccaaac tggagaacgc gaagcagtct     1020
gcggagcgga acagcagcat ggcggggggcg gcgcacgagg agctgcagca gacgcacatc     1080
cgcatcgaca gcctcagcgc agagctcagt cagctgcaga gcagctggc ggccaaagag      1140 gcgaagctgc gggaggtgga ggaggcgctg agccgggagc gggaggggg gcggcggctg       1200 ctggccgaga aggagcgcga gatggcggag atgcgcgcgc ggatgcagca gcagttggat     1260
gagtaccagg agctgctgga catcaaactg gcgctggaca tggagatcaa cgcctaccgc     1320
aaactgctgg agggcgagga ggagcggctc cgtctgtctc cgagcccctc ctcccagcgc     1380
ggcgcgcgga gctccgggct gcagcactca ggcgcgggca gcgccaagaa gcggcgcctg     1440
gaggacgggg agggccggga gggccgggag ggccgcacga gcttctcgca ccacgccagg     1500
accagcggga gggtcggcgt cgaggaggtg gacctggagg gcgcttcgt ccgcctccgc      1560 aacaaatcca atgaggacca ggccctgggg aactggcagg tgaagcggca gaacggggac     1620
gacccccccc tgacgtaccg cttcccccg aagttcactc tgaaggcggg tcaggcggtc      1680
acgatctggg cctcgggggc cggcgcgacc cacagccccc ccagcgatgt ggtgtggaag     1740
gcgcagagct cgtggggcag cggggacagt ctgcgcaccg ccctcatcaa ctccaacgga     1800
gaggaggtgg ccatgcggaa gttggtgcgc accgtcatca tcaacgacga cgacgaggat     1860
gaggaggacg acgaagtcag catccatcac cgccaccacc actcgggctg cagcggctcc     1920
gcagacccgg cggagtacaa cctgcgctcc cgcacggtgc tgtgcgggac gtgcgggcag     1980
cccgcagaca aggcagcgc cgccgccgcc tcctccgcct cctccgcctc caccgtcacc      2040
gtcagccgcg gctaccgcag ctccggcggc ggcatcgggg agggactgct cggccgctcc     2100
tacgtgctgg gcggagccgg gccgcggcgg caggctccgg ccccgcaggg ctgcagcatt     2160
atgtaatgcg gaccccccg ggctgctccg ccccctcccc ccccgggcgg cccccccctc     2220
attttgggct catttccccc ccaaagcagc gcaaaccaaa gatggctttt tttgttctct     2280
tttctatggc cgcgttttgt acggagctcc caggggggt ttccctctt tttgtgaagg      2340 gagacggaga acctttattt ctacgccccc cccccataa aaaaaaaa              2388
```

<210> SEQ ID NO 11
<211> LENGTH: 657
<212> TYPE: PRT
<213> ORGANISM: Gallus gallus

<400> SEQUENCE: 11

```
Met Ser Thr Pro Ser Gln Arg Arg Ser Gly Arg Gly Gly Pro Ser
1               5                  10                  15

Gly Thr Pro Leu Ser Pro Thr Arg Ile Thr Arg Leu Gln Glu Lys Glu
            20                  25                  30

Asp Leu Gln Glu Leu Asn Asp Arg Leu Ala Val Tyr Ile Asp Lys Val
        35                  40                  45

Arg Ser Leu Glu Leu Glu Asn Ala Gly Leu Arg Leu Arg Ile Thr Glu
    50                  55                  60

Ser Glu Glu Val Val Ser Arg Glu Val Ser Gly Ile Lys Ala Ala Tyr
65                  70                  75                  80
```

-continued

```
Glu Ala Glu Leu Ala Asp Ala Arg Lys Thr Leu Asp Ser Val Ala Lys
                 85                  90                  95
Glu Arg Ala Arg Leu Gln Leu Glu Leu Ser Lys Val Arg Glu Glu His
            100                 105                 110
Lys Glu Leu Lys Ala Arg Asn Ala Lys Glu Ala Asp Leu Leu Ala
        115                 120                 125
Ala Gln Ala Arg Leu Lys Asp Leu Glu Ala Leu Leu Asn Ser Lys Glu
    130                 135                 140
Ala Ala Leu Ser Thr Ala Leu Gly Glu Lys Arg Asn Leu Glu Asn Glu
145                 150                 155                 160
Val Arg Asp Leu Arg Ala Gln Val Ala Lys Leu Glu Gly Ala Leu Ser
                165                 170                 175
Glu Ala Lys Lys Gln Leu Gln Asp Glu Met Leu Arg Arg Val Asp Ala
            180                 185                 190
Glu Asn Arg Leu Gln Thr Leu Lys Glu Glu Leu Glu Phe Gln Lys Asn
        195                 200                 205
Ile Tyr Ser Glu Glu Leu Arg Glu Thr Lys Arg Arg His Glu Thr Arg
    210                 215                 220
Leu Val Glu Ile Asp Asn Gly Arg Gln Gln Phe Glu Ser Lys Leu
225                 230                 235                 240
Ala Glu Ala Leu Gln Asp Leu Arg Arg Gln His Glu Asp Gln Ile Arg
                245                 250                 255
His Tyr Arg Asp Glu Leu Glu Lys Thr Tyr Gly Ala Lys Leu Glu Asn
            260                 265                 270
Ala Lys Gln Ser Ala Glu Arg Asn Ser Ser Met Ala Gly Ala Ala His
        275                 280                 285
Glu Glu Leu Gln Gln Thr His Ile Arg Ile Asp Ser Leu Ser Ala Glu
    290                 295                 300
Leu Ser Gln Leu Gln Lys Gln Leu Ala Ala Lys Glu Ala Lys Leu Arg
305                 310                 315                 320
Glu Val Glu Glu Ala Leu Ser Arg Glu Arg Glu Gly Gly Arg Arg Leu
                325                 330                 335
Leu Ala Glu Lys Glu Arg Glu Met Ala Glu Met Arg Ala Arg Met Gln
            340                 345                 350
Gln Gln Leu Asp Glu Tyr Gln Glu Leu Leu Asp Ile Lys Leu Ala Leu
        355                 360                 365
Asp Met Glu Ile Asn Ala Tyr Arg Lys Leu Leu Glu Gly Glu Glu Glu
    370                 375                 380
Arg Leu Arg Leu Ser Pro Ser Pro Ser Ser Gln Arg Gly Ala Arg Ser
385                 390                 395                 400
Ser Gly Leu Gln His Ser Gly Ala Gly Ser Ala Lys Lys Arg Arg Leu
                405                 410                 415
Glu Asp Gly Glu Gly Arg Glu Gly Arg Glu Gly Arg Thr Ser Phe Ser
            420                 425                 430
His His Ala Arg Thr Ser Gly Arg Val Gly Val Glu Val Asp Leu
        435                 440                 445
Glu Gly Arg Phe Val Arg Leu Arg Asn Lys Ser Asn Glu Asp Gln Ala
    450                 455                 460
Leu Gly Asn Trp Gln Val Lys Arg Gln Asn Gly Asp Asp Pro Leu
465                 470                 475                 480
Thr Tyr Arg Phe Pro Pro Lys Phe Thr Leu Lys Ala Gly Gln Ala Val
                485                 490                 495
Thr Ile Trp Ala Ser Gly Ala Gly Ala Thr His Ser Pro Pro Ser Asp
```

```
            500             505             510
   Val Val Trp Lys Ala Gln Ser Ser Trp Gly Ser Gly Asp Ser Leu Arg
               515                 520                 525

Thr Ala Leu Ile Asn Ser Asn Gly Glu Glu Val Ala Met Arg Lys Leu
               530                 535                 540

Val Arg Thr Val Ile Ile Asn Asp Asp Glu Asp Glu Glu Asp Asp
   545                 550                 555                 560

Glu Val Ser Ile His His Arg His His Ser Gly Cys Ser Gly Ser
                       565                 570                 575

Ala Asp Pro Ala Glu Tyr Asn Leu Arg Ser Arg Thr Val Leu Cys Gly
               580                 585                 590

Thr Cys Gly Gln Pro Ala Asp Lys Gly Ser Ala Ala Ala Ser Ser
               595                 600                 605

Ala Ser Ser Ala Ser Thr Val Thr Val Ser Arg Gly Tyr Arg Ser Ser
               610                 615                 620

Gly Gly Gly Ile Gly Glu Gly Leu Leu Gly Arg Ser Tyr Val Leu Gly
   625                 630                 635                 640

Gly Ala Gly Pro Arg Arg Gln Ala Pro Ala Pro Gln Gly Cys Ser Ile
               645                 650                 655

Met
```

<210> SEQ ID NO 12
<211> LENGTH: 2111
<212> TYPE: DNA
<213> ORGANISM: Xenopus laevis

<400> SEQUENCE: 12

```
ccaagctatg gagaccccag gtcagaagcg ggcgacccgc agcacccaca ccccactctc    60
ccccacccgt atcacccgcc tgcaggagaa ggaagatctg caggggctca atgaccgatt   120
ggccgtctac atcgacaagg tgcgttccct ggagctggaa acgcccggc tgcgtctgcg    180 aatcaccgag tctgaagacg tcatcagccg cgaggtcacg gcatcaagt cagcgtatga   240 gacggagctg gcggacgcac ggaaaactct ggactcggtg gccaaggaga gggctcgtct   300
gcagctggag ctgagcaaga tccgcgagga gcacaaggag ctgaaagcga ggaatgccaa   360
gaaagagagc gatctattga cagcgcaggc cagactgaag gatttggagg ccctgttgaa   420
ctctaaagat gccgccctca ccacagcgct gggagagaag aggaatctgg agaatgagat   480
cagggaactt aaggctcaca ttgcaaagtt ggaggccagc ctcgccgaca caaagaaaca   540
actgcaggac gagatgctcc gtcgtgtgga tactgagaac cgtaaccaga cgctgaagga   600
ggaacttgag ttccaaaaga gcatttacaa cgaggagatg cgggagacta acgccgcca   660 tgagacccga ctggtggagg tcgacaacgg gcgccagagg gagtttgagt ctaaattggc   720
tgatgccctt catgagttgc gtgcccaaca tgaggggcag ataggcctgt acaaggaaga   780
gctggggaag acttacaatg ccaagctgga gaatgccaag cagtcggcgg agaggaacag   840
cagtctggtg ggagaagctc aggagagat tcagcagagc aggatccgca tcgacagtct   900
ctcggcccag ctcagccaac tgcagaaaca gctggcggcc agagaggcca acttcggga    960 tctggaggac gcctatgcgc gtgaacggga ctccagccgc cggctcctgg cagacaagga  1020
ccgggagatg gcggaaatga gggcccgcat gcaacaacag ctggacgagt accaggagct  1080
gctggacatt aaactggctc tggacatgga gatcaacgcc taccgcaagt tactggaggg  1140
agaggaggag aggctgcgtc tctccccag tcccaacacc cagaagaggt cggcccggac  1200
```

-continued

```
catcgcctct cactcggggg cccacatctc ctcctcggcc tccaagagac gtcgcctgga  1260 agaagggaa tcgcggagca gcagcttcac ccaacacgcc cgcaccaccg ggaaagtgtc   1320
agtggaagag gtggatcccg agggaaata tgtccgactg aggaacaaga gtaatgagga   1380
ccaatcgctg gggaactggc agatcaagcg tcagatcggg gacgagaccc ccattgtgta  1440
caagttccct cccagactta cactaaaggc cggacaaacc gtaacgattt gggcatcagg   1500
agctggagcc acaaatagtc cccccagtga tttagtgtgg aaggcccaga gctcttgggg   1560
aacaggcgac agtattcgca cagctctgct cacatcaagc aatgaggaag ttgctatgag   1620
gaaactggtg cgaactgtgg tcatcaatga tgaagatgat gaagataatg atgatatgga   1680
acatcaccac caccatcatc atcatcatca tgatgggcag aactctagtg gagaccctgg   1740
ggagtacaac ctgcgctctc gcactatcgt ttgcaccagc tgtgggcgcc cagctgagaa   1800
gagtgtcctg gcctcccagg gttctgggtt ggtcactgga tcatcaggtt cttcttcctc   1860
cagcgtcacc cttactcgga cctaccgtag cacaggggga accagcgggg gcagtggcct   1920 cgggagagt ccggtcacca ggaacttcat tgttggaaat ggccaacgtg cccaggtcgc    1980
cccgcagaac tgcagtataa tgtaaccgga tgccaccact gttcttatca ccaagtgccc   2040
aagctaaaga gaatttttg tttttttaat gtatttatt ttttttttat actgcaagaa    2100
ttttataaag g                                                       2111
```

<210> SEQ ID NO 13
<211> LENGTH: 665
<212> TYPE: PRT
<213> ORGANISM: Xenopus laevis

<400> SEQUENCE: 13

```
Met Glu Thr Pro Gly Gln Lys Arg Ala Thr Arg Ser Thr His Thr Pro
 1               5                  10                  15

Leu Ser Pro Thr Arg Ile Thr Arg Leu Gln Glu Lys Glu Asp Leu Gln
            20                  25                  30

Gly Leu Asn Asp Arg Leu Ala Val Tyr Ile Asp Lys Val Arg Ser Leu
        35                  40                  45

Glu Leu Glu Asn Ala Arg Leu Arg Leu Arg Ile Thr Glu Ser Glu Asp
    50                  55                  60

Val Ile Ser Arg Glu Val Thr Gly Ile Lys Ser Ala Tyr Glu Thr Glu
65                  70                  75                  80

Leu Ala Asp Ala Arg Lys Thr Leu Asp Ser Val Ala Lys Glu Arg Ala
                85                  90                  95

Arg Leu Gln Leu Glu Leu Ser Lys Ile Arg Glu Glu His Lys Glu Leu
            100                 105                 110

Lys Ala Arg Asn Ala Lys Lys Glu Ser Asp Leu Leu Thr Ala Gln Ala
        115                 120                 125

Arg Leu Lys Asp Leu Glu Ala Leu Leu Asn Ser Lys Asp Ala Ala Leu
    130                 135                 140

Thr Thr Ala Leu Gly Glu Lys Arg Asn Leu Glu Asn Glu Ile Arg Glu
145                 150                 155                 160

Leu Lys Ala His Ile Ala Lys Leu Glu Ala Ser Leu Ala Asp Thr Lys
                165                 170                 175

Lys Gln Leu Gln Asp Glu Met Leu Arg Arg Val Asp Thr Glu Asn Arg
            180                 185                 190

Asn Gln Thr Leu Lys Glu Glu Leu Glu Phe Gln Lys Ser Ile Tyr Asn
        195                 200                 205
```

-continued

```
Glu Glu Met Arg Glu Thr Lys Arg Arg His Glu Thr Arg Leu Val Glu
    210                 215                 220
Val Asp Asn Gly Arg Gln Arg Glu Phe Glu Ser Lys Leu Ala Asp Ala
225                 230                 235                 240
Leu His Glu Leu Arg Ala Gln His Glu Gly Gln Ile Gly Leu Tyr Lys
                245                 250                 255
Glu Glu Leu Gly Lys Thr Tyr Asn Ala Lys Leu Glu Asn Ala Lys Gln
            260                 265                 270
Ser Ala Glu Arg Asn Ser Ser Leu Val Gly Glu Ala Gln Glu Glu Ile
        275                 280                 285
Gln Gln Ser Arg Ile Arg Ile Asp Ser Leu Ser Ala Gln Leu Ser Gln
    290                 295                 300
Leu Gln Lys Gln Leu Ala Ala Arg Glu Ala Lys Leu Arg Asp Leu Glu
305                 310                 315                 320
Asp Ala Tyr Ala Arg Glu Arg Asp Ser Arg Arg Leu Leu Ala Asp
                325                 330                 335
Lys Asp Arg Glu Met Ala Glu Met Arg Ala Arg Met Gln Gln Gln Leu
                340                 345                 350
Asp Glu Tyr Gln Glu Leu Leu Asp Ile Lys Leu Ala Leu Asp Met Glu
                355                 360                 365
Ile Asn Ala Tyr Arg Lys Leu Leu Glu Gly Glu Glu Arg Leu Arg
370                 375                 380
Leu Ser Pro Ser Pro Asn Thr Gln Lys Arg Ser Ala Arg Thr Ile Ala
385                 390                 395                 400
Ser His Ser Gly Ala His Ile Ser Ser Ala Ser Lys Arg Arg Arg
                405                 410                 415
Leu Glu Glu Gly Glu Ser Arg Ser Ser Phe Thr Gln His Ala Arg
            420                 425                 430
Thr Thr Gly Lys Val Ser Val Glu Glu Val Asp Pro Glu Gly Lys Tyr
                435                 440                 445
Val Arg Leu Arg Asn Lys Ser Asn Glu Asp Gln Ser Leu Gly Asn Trp
    450                 455                 460
Gln Ile Lys Arg Gln Ile Gly Asp Glu Thr Pro Ile Val Tyr Lys Phe
465                 470                 475                 480
Pro Pro Arg Leu Thr Leu Lys Ala Gly Gln Thr Val Thr Ile Trp Ala
                485                 490                 495
Ser Gly Ala Gly Ala Thr Asn Ser Pro Pro Ser Asp Leu Val Trp Lys
            500                 505                 510
Ala Gln Ser Ser Trp Gly Thr Gly Asp Ser Ile Arg Thr Ala Leu Leu
        515                 520                 525
Thr Ser Ser Asn Glu Glu Val Ala Met Arg Lys Leu Val Arg Thr Val
    530                 535                 540
Val Ile Asn Asp Glu Asp Asp Glu Asp Asn Asp Asp Met Glu His His
545                 550                 555                 560
His His His His His His His Asp Gly Gln Asn Ser Ser Gly Asp
                565                 570                 575
Pro Gly Glu Tyr Asn Leu Arg Ser Arg Thr Ile Val Cys Thr Ser Cys
            580                 585                 590
Gly Arg Pro Ala Glu Lys Ser Val Leu Ala Ser Gln Gly Ser Gly Leu
        595                 600                 605
Val Thr Gly Ser Ser Gly Ser Ser Ser Ser Val Thr Leu Thr Arg
    610                 615                 620
Thr Tyr Arg Ser Thr Gly Gly Thr Ser Gly Gly Ser Gly Leu Gly Glu
```

|  |  |  |  |
|---|---|---|---|
| 625 | 630 | 635 | 640 |

Ser Pro Val Thr Arg Asn Phe Ile Val Gly Asn Gly Gln Arg Ala Gln
                     645                       650                     655

Val Ala Pro Gln Asn Cys Ser Ile Met
          660                     665

<210> SEQ ID NO 14
<211> LENGTH: 2078
<212> TYPE: DNA
<213> ORGANISM: Danio rerio

<400> SEQUENCE: 14

| | |
|---|---|
| atggagactc caggtcagaa acgaagcagc cgcggtgggg tgaccaatgt cctgtcccct | 60 |
| acccgcatct ctcgattgca ggaaaaggag gacttgagca acctgaatga ccgtctggcg | 120 |
| gtctacatcg ataaggttcg ctctctggag gtggagaacg caggtctgcg tatgcgcatc | 180 |
| actgaatccg agacggagat cagccggag ctgagtggca tgaaagcggc gtacgaggct | 240 |
| gaactcgcag atgccaggaa acactggac tcggtggcca agaacgagc ccgactgcaa | 300 |
| ctggagctca gcaaagtgcg tgaggactac aaggagctga aggccaggaa cggtaagaaa | 360 |
| gaagcagatc tggaatctgc tctggccagg ctgaaggatc tggagtctct actgaactcc | 420 |
| aaggacgcgt ctctctccac agctctgggg gagaagagaa cactggaggt ggaagtcaga | 480 |
| gatttgaaag cccagctggc caagttggag ggcagtctaa cgatgcaaa gaagcagctg | 540 |
| caggatgaaa tgctgcgacg tgtggatgcc gaaaaccgaa tccagacact gaagaggag | 600 |
| ctggagttcc agaagaacat ctactctgag gagctccgtg agtctaagcg cagatatgag | 660 |
| tcacgtgtgg tggagattga cagcggccgc cagcaggatt atgagagtaa actggccgac | 720 |
| gctttaactg acctccgcaa ccaacatgaa gagcagcttc gcatctacaa ggaagaaatc | 780 |
| gagaagacct acaactccaa gctggaaaat gctcgctctt ccgctgaaag gaacagtcat | 840 |
| ctggttggag ccgcccatga ggaactgcag caaacacgtg ttaggatgga gggtgtgagt | 900 |
| tcacagctca gtcagctgca gaaacagttg gctgctcgag aggcgaagat ccgcgagctg | 960 |
| gaagaggccc tgtccagaga gagggatatt ttgcgccgtc gtctggagga caaggagaag | 1020 |
| gagatggctg agatgagaca gcgcatgcag caacagctgg acgagtacca ggagctgctg | 1080 |
| gacatcaaac tcgctctgga catggagatc agtgcctaca ggaagcttct ggagggagag | 1140 |
| gaggaaagac ttcgtctgtc tccgagtcct cctcctgctc gtgggggtgac ggtgaccccgc | 1200 |
| tcctctggtt caggctctca cactcgtgtg gttcagagca gcaccagtcg cacatcctcc | 1260 |
| ggcagcgcca agaaacggcg cttgaatgat aacgacagtg atgcctccag tgtggttgga | 1320 |
| ggaacagtga cccgcacacg gatcttccag caagcctcag ccagcggccg cgtcaccgtt | 1380 |
| gacgaagtcg acctggaagg aaaatttgtg cggcttaata acaagtctga ccaggatcag | 1440 |
| tctctggggtc actggcaggt gaagaggcag attggttctg gcactccat cgtctacaag | 1500 |
| tttccacccca aatttaacct gaaggcaggg cagactgtca cgatctgggc tgcaggagcc | 1560 |
| ggaggcaccc acagtcctcc cagtgacctg gtgtggaaga cccagaactc atggggcagc | 1620 |
| ggtgatttgt tccagaccac cctcatcagc tccagcggag aggaaatggc gatgagaaaa | 1680 |
| gtcacacgta ctctgttcca ggatgaggaa gatgatgaga tggcggctca cagcacatgc | 1740 |
| ggagacagcg agtataacct gcgcagccgt actgtgctgt gcggctcgtg tggtcagccg | 1800 |
| tccgacagga acagcagctg tgtttctgcc agctcaggaa gtccagcgc atctcgctcc | 1860 |
| ttcagcagtg gaggaggagg aggactcact gaagcttttg tgtcgccctc tcactttatt | 1920 |

-continued

```
gtgagcaacg acaaacccag acaggctgga cccaaagtgg acaactgctc tattatgtag    1980
aggagctgaa agcaaaccct gaccatctgt gctttcacag aaaccaggcg gaactgatcc    2040
caaaactagt ttcttttcag ttttttatg tcttatca                            2078
```

<210> SEQ ID NO 15
<211> LENGTH: 659
<212> TYPE: PRT
<213> ORGANISM: Danio rerio

<400> SEQUENCE: 15

```
Met Glu Thr Pro Gly Gln Lys Arg Ser Ser Arg Gly Gly Val Thr Asn
1               5                   10                  15

Val Leu Ser Pro Thr Arg Ile Ser Arg Leu Gln Glu Lys Glu Asp Leu
            20                  25                  30

Ser Asn Leu Asn Asp Arg Leu Ala Val Tyr Ile Asp Lys Val Arg Ser
        35                  40                  45

Leu Glu Val Glu Asn Ala Gly Leu Arg Met Arg Ile Thr Glu Ser Glu
    50                  55                  60

Thr Glu Ile Ser Arg Glu Leu Ser Gly Met Lys Ala Ala Tyr Glu Ala
65                  70                  75                  80

Glu Leu Ala Asp Ala Arg Lys Thr Leu Asp Ser Val Ala Lys Glu Arg
                85                  90                  95

Ala Arg Leu Gln Leu Glu Leu Ser Lys Val Arg Glu Asp Tyr Lys Glu
            100                 105                 110

Leu Lys Ala Arg Asn Gly Lys Lys Glu Ala Asp Leu Glu Ser Ala Leu
        115                 120                 125

Ala Arg Leu Lys Asp Leu Glu Ser Leu Leu Asn Ser Lys Asp Ala Ser
    130                 135                 140

Leu Ser Thr Ala Leu Gly Glu Lys Arg Thr Leu Glu Val Glu Val Arg
145                 150                 155                 160

Asp Leu Lys Ala Gln Leu Ala Lys Leu Glu Gly Ser Leu Asn Asp Ala
                165                 170                 175

Lys Lys Gln Leu Gln Asp Glu Met Leu Arg Arg Val Asp Ala Glu Asn
            180                 185                 190

Arg Ile Gln Thr Leu Lys Glu Glu Leu Glu Phe Gln Lys Asn Ile Tyr
        195                 200                 205

Ser Glu Glu Leu Arg Glu Ser Lys Arg Arg Tyr Glu Ser Arg Val Val
    210                 215                 220

Glu Ile Asp Ser Gly Arg Gln Gln Asp Tyr Glu Ser Lys Leu Ala Asp
225                 230                 235                 240

Ala Leu Thr Asp Leu Arg Asn Gln His Glu Glu Gln Leu Arg Ile Tyr
                245                 250                 255

Lys Glu Glu Ile Glu Lys Thr Tyr Asn Ser Lys Leu Glu Asn Ala Arg
            260                 265                 270

Ser Ser Ala Glu Arg Asn Ser His Leu Val Gly Ala Ala His Glu Glu
        275                 280                 285

Leu Gln Gln Thr Arg Val Arg Met Glu Gly Val Ser Ser Gln Leu Ser
    290                 295                 300

Gln Leu Gln Lys Gln Leu Ala Ala Arg Glu Ala Lys Ile Arg Glu Leu
305                 310                 315                 320

Glu Glu Ala Leu Ser Arg Glu Arg Asp Ile Leu Arg Arg Leu Glu
                325                 330                 335

Asp Lys Glu Lys Glu Met Ala Glu Met Arg Gln Arg Met Gln Gln Gln
```

```
                    340                 345                 350
Leu Asp Glu Tyr Gln Glu Leu Leu Asp Ile Lys Leu Ala Leu Asp Met
                355                 360                 365
Glu Ile Ser Ala Tyr Arg Lys Leu Leu Glu Gly Glu Glu Arg Leu
            370                 375                 380
Arg Leu Ser Pro Ser Pro Pro Ala Arg Gly Val Thr Val Thr Arg
385                 390                 395                 400
Ser Ser Gly Ser Gly Ser His Thr Arg Val Val Gln Ser Ser Thr Ser
                405                 410                 415
Arg Thr Ser Ser Gly Ser Ala Lys Lys Arg Arg Leu Asn Asp Asn Asp
                420                 425                 430
Ser Asp Ala Ser Ser Val Val Gly Gly Thr Val Thr Arg Thr Arg Ile
                435                 440                 445
Phe Gln Gln Ala Ser Ala Ser Gly Arg Val Thr Val Asp Glu Val Asp
                450                 455                 460
Leu Glu Gly Lys Phe Val Arg Leu Asn Asn Lys Ser Asp Gln Asp Gln
465                 470                 475                 480
Ser Leu Gly His Trp Gln Val Lys Arg Gln Ile Gly Ser Gly Thr Pro
                485                 490                 495
Ile Val Tyr Lys Phe Pro Pro Lys Phe Asn Leu Lys Ala Gly Gln Thr
                500                 505                 510
Val Thr Ile Trp Ala Ala Gly Ala Gly Thr His Ser Pro Pro Ser
                515                 520                 525
Asp Leu Val Trp Lys Thr Gln Asn Ser Trp Ser Gly Asp Leu Phe
                530                 535                 540
Gln Thr Thr Leu Ile Ser Ser Gly Glu Glu Met Ala Met Arg Lys
545                 550                 555                 560
Val Thr Arg Thr Leu Phe Gln Asp Glu Glu Asp Glu Met Ala Ala
                565                 570                 575
His Ser Thr Cys Gly Asp Ser Glu Tyr Asn Leu Arg Ser Arg Thr Val
                580                 585                 590
Leu Cys Gly Ser Cys Gly Gln Pro Ser Asp Arg Asn Ser Ser Cys Val
                595                 600                 605
Ser Ala Ser Ser Gly Val Ser Ser Ala Ser Arg Ser Phe Ser Ser Gly
                610                 615                 620
Gly Gly Gly Gly Leu Thr Glu Ala Phe Val Ser Pro Ser His Phe Ile
625                 630                 635                 640
Val Ser Asn Asp Lys Pro Arg Gln Ala Gly Pro Lys Val Asp Asn Cys
                645                 650                 655
Ser Ile Met

<210> SEQ ID NO 16
<211> LENGTH: 15
<212> TYPE: PRT
<213> ORGANISM: Mus musculus

<400> SEQUENCE: 16

Leu Leu Gly Asn Ser Ser Pro Arg Ser Gln Ser Ser Gln Asn Cys
1               5                   10                  15

<210> SEQ ID NO 17
<211> LENGTH: 17
<212> TYPE: PRT
<213> ORGANISM: Gallus gallus

<400> SEQUENCE: 17
```

```
Val Leu Gly Gly Ala Gly Pro Arg Arg Gln Ala Pro Ala Pro Gln Gly
1               5                   10                  15

Cys

<210> SEQ ID NO 18
<211> LENGTH: 15
<212> TYPE: PRT
<213> ORGANISM: Xenopus laevis

<400> SEQUENCE: 18

Ile Val Gly Asn Gly Gln Arg Ala Gln Val Ala Pro Gln Asn Cys
1               5                   10                  15

<210> SEQ ID NO 19
<211> LENGTH: 20
<212> TYPE: PRT
<213> ORGANISM: Danio rerio

<400> SEQUENCE: 19

Ile Val Ser Asn Asp Lys Pro Arg Gln Ala Gly Pro Lys Val Asp Asn
1               5                   10                  15

Cys Ser Ile Met
            20

<210> SEQ ID NO 20
<211> LENGTH: 18
<212> TYPE: PRT
<213> ORGANISM: Homo sapiens

<400> SEQUENCE: 20

Leu Leu Gly Asn Ser Ser Pro Arg Thr Gln Ser Pro Gln Asn Cys Ser
1               5                   10                  15

Ile Met

<210> SEQ ID NO 21
<211> LENGTH: 18
<212> TYPE: PRT
<213> ORGANISM: Mus musculus

<400> SEQUENCE: 21

Leu Leu Gly Asn Ser Ser Pro Arg Ser Gln Ser Ser Gln Asn Cys Ser
1               5                   10                  15

Ile Met

<210> SEQ ID NO 22
<211> LENGTH: 20
<212> TYPE: PRT
<213> ORGANISM: Gallus gallus

<400> SEQUENCE: 22

Val Leu Gly Gly Ala Gly Pro Arg Arg Gln Ala Pro Ala Pro Gln Gly
1               5                   10                  15

Cys Ser Ile Met
            20

<210> SEQ ID NO 23
<211> LENGTH: 18
<212> TYPE: PRT
<213> ORGANISM: Xenopus laevis

<400> SEQUENCE: 23
```

-continued

```
Ile Val Gly Asn Gly Gln Arg Ala Gln Val Ala Pro Gln Asn Cys Ser
1               5                   10                  15

Ile Met

<210> SEQ ID NO 24
<211> LENGTH: 20
<212> TYPE: PRT
<213> ORGANISM: Danio rerio

<400> SEQUENCE: 24

Ile Val Ser Asn Asp Lys Pro Arg Gln Ala Gly Pro Lys Val Asp Asn
1               5                   10                  15

Cys Ser Ile Met
            20
```